United States Patent
Kramps et al.

(10) Patent No.: US 9,226,959 B2
(45) Date of Patent: Jan. 5, 2016

(54) NUCLEIC ACIDS COMPRISING FORMULA $(N_uG_lX_mG_nN_v)_a$ AND DERIVATIVES THEREOF AS IMMUNOSTIMULATING AGENT/ADJUVANT

(75) Inventors: Thomas Kramps, Tübingen (DE); Söhnke Voss, Tübingen (DE); Jochen Probst, Wolfschlugen (DE); Ingmar Hoerr, Tübingen (DE)

(73) Assignee: CureVac AG, Tübingen (DE)

( * ) Notice: Subject to any disclaimer, the term of this patent is extended or adjusted under 35 U.S.C. 154(b) by 947 days.

(21) Appl. No.: 12/672,442

(22) PCT Filed: Jan. 28, 2009

(86) PCT No.: PCT/EP2009/000546
§ 371 (c)(1),
(2), (4) Date: Oct. 14, 2011

(87) PCT Pub. No.: WO2009/095226
PCT Pub. Date: Aug. 6, 2009

(65) Prior Publication Data
US 2012/0021043 A1    Jan. 26, 2012

(30) Foreign Application Priority Data

Jan. 31, 2008 (EP) .................................. 08001827

(51) Int. Cl.
| | | |
|---|---|---|
| C07H 21/02 | (2006.01) | |
| A61K 39/00 | (2006.01) | |
| A61K 39/39 | (2006.01) | |
| A61P 37/04 | (2006.01) | |
| C07H 21/00 | (2006.01) | |
| C12N 15/117 | (2010.01) | |

(52) U.S. Cl.
CPC ................ *A61K 39/39* (2013.01); *C07H 21/00* (2013.01); *A61K 2039/55561* (2013.01); *C12N 15/117* (2013.01); *C12N 2310/17* (2013.01)

(58) Field of Classification Search
CPC ............. C12N 15/117; C12N 2310/17; C12N 2310/33; A61K 2039/55561
See application file for complete search history.

(56) References Cited

U.S. PATENT DOCUMENTS

| | | | |
|---|---|---|---|
| 3,906,092 A | 9/1975 | Hilleman et al. | |
| 4,373,071 A | 2/1983 | Itakura | |
| 4,401,796 A | 8/1983 | Itakura | |
| 4,415,732 A | 11/1983 | Caruthers et al. | |
| 4,578,399 A | 3/1986 | Schorlemmer et al. | |
| 5,516,652 A | 5/1996 | Abramovitz et al. | |
| 5,663,153 A | 9/1997 | Hutcherson et al. | |
| 5,663,163 A | 9/1997 | Takaya et al. | |
| 5,844,075 A | 12/1998 | Kawakami et al. | |
| 5,965,720 A | 10/1999 | Gryaznov et al. | |
| 6,096,307 A | 8/2000 | Braswell et al. | |
| 6,218,371 B1 | 4/2001 | Krieg et al. | |
| 6,239,116 B1 | 5/2001 | Krieg et al. | |
| 6,322,967 B1 | 11/2001 | Parkin | |
| 6,406,705 B1 | 6/2002 | Davis et al. | |
| 6,498,148 B1 | 12/2002 | Raz | |
| 6,514,948 B1 | 2/2003 | Raz et al. | |
| 6,552,006 B2 | 4/2003 | Raz et al. | |
| 6,589,940 B1 | 7/2003 | Raz et al. | |
| 6,610,661 B1 | 8/2003 | Carson et al. | |
| 6,689,757 B1 | 2/2004 | Craig | |
| 6,716,434 B1 | 4/2004 | Ansley et al. | |
| 7,001,890 B1 | 2/2006 | Wagner et al. | |
| 7,208,478 B2 | 4/2007 | Carson et al. | |
| 7,407,944 B2 | 8/2008 | Agrawal et al. | |
| 7,470,674 B2 | 12/2008 | Agrawal et al. | |
| 7,517,862 B2 | 4/2009 | Agrawal et al. | |

(Continued)

FOREIGN PATENT DOCUMENTS

| | | |
|---|---|---|
| AU | 776268 | 12/2000 |
| EP | 0347501 | 12/1989 |
| EP | 0772619 | 5/1997 |
| EP | 0839912 | 5/1998 |
| EP | 1083232 | 3/2001 |
| EP | 1167379 | 1/2002 |
| EP | 1374894 | 1/2004 |
| EP | 1393745 | 3/2004 |
| WO | WO91/05560 | 5/1991 |
| WO | WO94/17093 | 8/1994 |

(Continued)

OTHER PUBLICATIONS

Guo et al, Protein tolerance to random amino acid change, PNAS, 2004, vol. 101 (25), pp. 9205-9210.*

(Continued)

*Primary Examiner* — Maria Marvich
(74) *Attorney, Agent, or Firm* — Parker Highlander PLLC

(57) ABSTRACT

The present invention relates to nucleic acids of the general formula (I): $(N_uG_lX_mG_nN_v)_a$ and derivatives thereof as an immunostimulating agent/adjuvant and to compositions containing same, optionally comprising an additional adjuvant. The present invention furthermore relates to a pharmaceutical composition or to a vaccine, each containing nucleic acids of formula (I) above and/or derivatives thereof as an immunostimulating agent, and optionally at least one additional pharmaceutically active component, e.g. an antigenic agent. The present invention relates likewise to the use of the pharmaceutical composition or of the vaccine for the treatment of cancer diseases, infectious diseases, allergies and autoimmune diseases etc. Likewise, the present invention includes the use of nucleic acids of the general formula (I): $(N_uG_lX_mG_nN_v)_a$ and/or derivatives thereof for the preparation of a pharmaceutical composition for the treatment of such diseases.

34 Claims, 2 Drawing Sheets

(56) References Cited

U.S. PATENT DOCUMENTS

Figure 1:
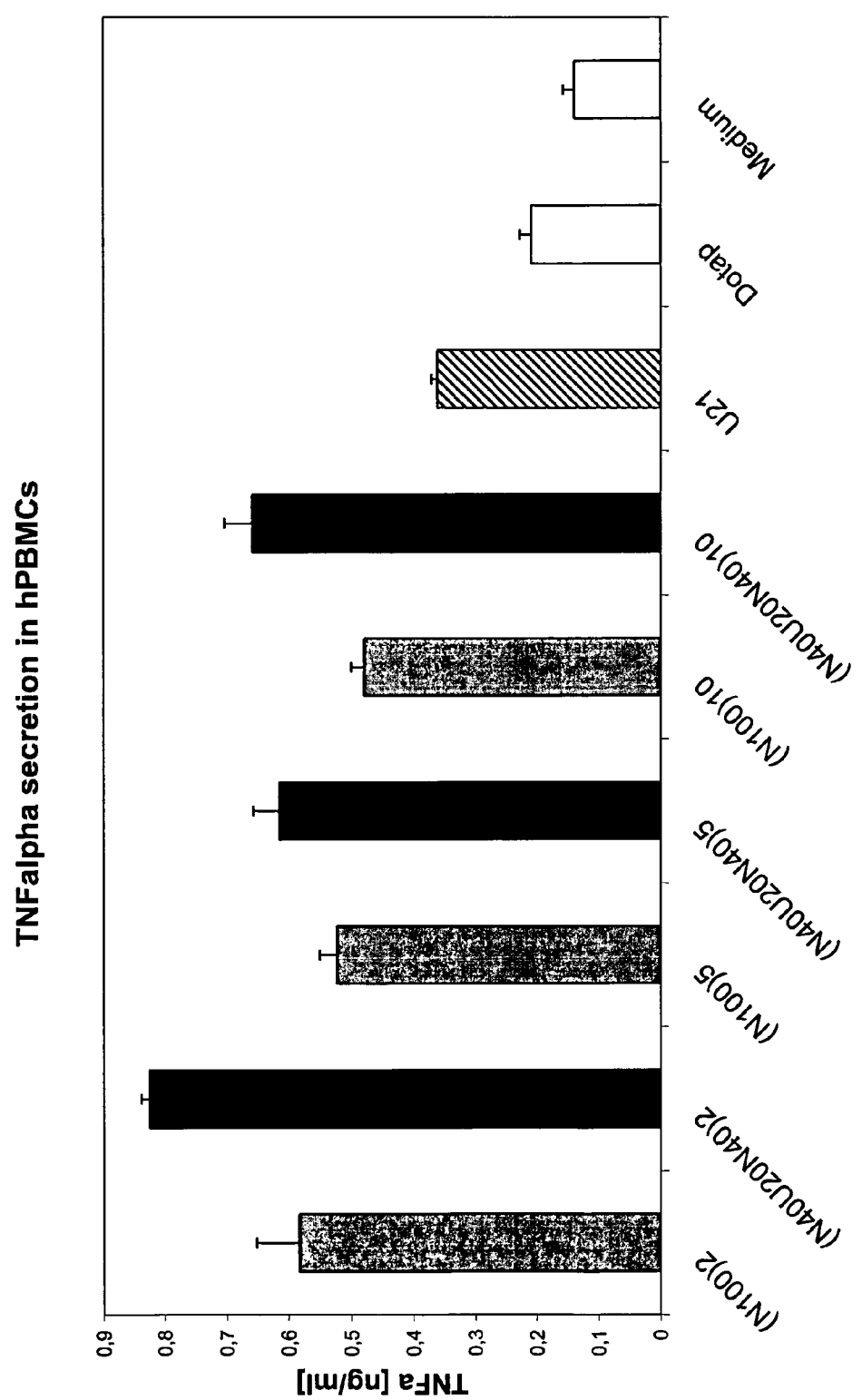

| | | |
|---|---|---|
| 2003/0225016 A1 | 12/2003 | Fearon et al. |
| 2003/0232074 A1 | 12/2003 | Lipford et al. |
| 2004/0006010 A1 | 1/2004 | Carson et al. |
| 2004/0006034 A1 | 1/2004 | Raz et al. |
| 2004/0047869 A1 | 3/2004 | Garcon et al. |
| 2004/0052763 A1 | 3/2004 | Mond et al. |
| 2005/0032730 A1 | 2/2005 | Von Der Mulbe et al. |
| 2005/0037494 A1 | 2/2005 | Hecker et al. |
| 2005/0059624 A1 | 3/2005 | Hoerr et al. |
| 2005/0130918 A1 | 6/2005 | Agrawal et al. |
| 2005/0250723 A1 | 11/2005 | Hoerr et al. |
| 2006/0172966 A1 | 8/2006 | Lipford et al. |
| 2007/0280929 A1 | 12/2007 | Hoerr et al. |
| 2008/0025944 A1 | 1/2008 | Hoerr et al. |
| 2009/0324584 A1 | 12/2009 | Hoerr et al. |
| 2010/0144846 A1* | 6/2010 | Jurk et al. .................. 514/44 R |

FOREIGN PATENT DOCUMENTS

| | | |
|---|---|---|
| WO | WO94/17792 | 8/1994 |
| WO | WO99/53961 | 10/1999 |
| WO | WO 00/73466 | 12/2000 |
| WO | WO00/75304 | 12/2000 |
| WO | WO01/04135 | 1/2001 |
| WO | WO01/75164 | 10/2001 |
| WO | WO01/93902 | 12/2001 |
| WO | WO01/97843 | 12/2001 |
| WO | WO02/00594 | 1/2002 |
| WO | WO02/00694 | 1/2002 |
| WO | WO02/078614 | 10/2002 |
| WO | WO02/098443 | 12/2002 |
| WO | WO03/028656 | 4/2003 |
| WO | WO03/057822 | 7/2003 |
| WO | WO 03/059381 | 7/2003 |
| WO | WO03/066649 | 8/2003 |
| WO | WO 03/074551 | 9/2003 |
| WO | WO03/086280 | 10/2003 |
| WO | WO2004/004743 | 1/2004 |
| WO | WO2004/058159 | 7/2004 |
| WO | WO2004/064782 | 8/2004 |
| WO | WO2004/092329 | 10/2004 |
| WO | WO 2005/000887 | 1/2005 |
| WO | WO2005/001022 | 1/2005 |
| WO | WO2005/030259 | 4/2005 |
| WO | WO 2005/030800 | 4/2005 |
| WO | WO-2005097993 A2 | 10/2005 |
| WO | WO 2006/002538 | 1/2006 |
| WO | WO2006/029223 | 3/2006 |
| WO | WO2006/116458 | 11/2006 |
| WO | WO2007/031322 | 3/2007 |
| WO | WO 2007/031877 | 3/2007 |
| WO | WO2007/042554 | 4/2007 |
| WO | WO 2007/062107 | 5/2007 |
| WO | WO-2007051303 A1 | 5/2007 |
| WO | WO-2007124755 A1 | 11/2007 |
| WO | WO-2008014979 A2 | 2/2008 |
| WO | WO2009/030481 | 3/2009 |
| WO | WO2009/053700 | 4/2009 |
| WO | WO2009/086640 | 7/2009 |
| WO | WO2010/037408 | 4/2010 |
| WO | WO 2010/037539 | 4/2010 |

OTHER PUBLICATIONS

Lesk et al, Prediction of Protein Function from Protein Sequence and Structure, p. 27 and 28, downloaded Sep. 16, 2007.*
Adams AD et al., Preparation and hybridization properties of oligonucleotides containing 1-alpha-D-arabinofuranosylthymine, Nucleic Acids Res. Jul. 11, 1991; 19(13):3647-51.
Bettinger T. et al., Peptide-mediated RNA delivery: a novel approach for enhanced transfection of primary and Post-mitotic cells, Nucleic Acids Research, 2001, vol. 29, No. 18, 3882-3891.
Fotin-Mleczek, Mariola et al., Messenger RNA-based vaccines with dual activity induce balanced TLR-7 dependent adaptive immune responses and provide antitumor activity, Journal of Immunotherapy, Raven Press, NY, US, vo.34, No. 1, Jan. 1, 2011, pp. 1-15.
Genbank Accession No. JK489756.1 GI: , 346421249, publically available Sep. 2011.
Georgieva et al., Comparative study on the changes in photosynthetic activity of the homoiochlorophyllous desiccation-tolerant Haberlea rhodopensis and desiccation-sensitive spinach leaves during desiccation and rehydration, Photosynthesis Research, vol. 85, pp. 191-203, Aug. 2005.
Romagne F., Current and future drugs targeting one class of innate immunity receptors: the Toll-like receptors, Drug Discov Today. Jan. 2007; 12(1-2):80-7. Epub Nov. 28, 2006.
Scheel et al., 2004; Immunostimulating capacities of stabilized RNA molecules; Eur. J. Immunol., vol. 24, pp. 537-547.
Stephens et al., Sequence analysis of the major outer membrane protein gene from Chlamydia trachomatis serovar L2, Journal of Bacteriology, vol. 168, No. 3, pp. 1277-1282, Dec. 1986.
Tse K et al., Update on toll-like receptor-directed therapies for human disease, Ann Rheum De. Nov. 2007; 66 Suppl 3: iii77-80. Review.
Zimmerman S et al., Immunostimulatory DNA as adjuvant: efficacy of phosphodiester CpG oligonucleotides is enhanced by 3' sequence modifications, Vaccine. Feb. 14, 2003; 21(9-10):990-5. (anly abstract).
Agrawal, 1996; Antisense oligonucleotides: towards clinical trials; Trends in Bietechnology; vol. 10; pp. 376-387.
Ara et al., 2001; Zymosan enhances the immune response to DNA vaccine for human immunodeficiency virus type-1 through the activation of complement system; Immunology; vol. 103, pp. 98-105.
Bayard et al.; 1985; Antiviral activity in L1210 cells of liposome-encapsulated (2'- 5')oligo(adenylate)analogues; Eur. J. Biochem., vol. 151, No. 2, pp. 319-326.
Bocchia et al., 2000; Antitumor vaccination: where we stand; Heamatologica, vol. 85, No. 11, pp. 1172-1206.
Buteau et al., 2002; Challenges in the Development of Effective Peptide Vaccines for Cancer; Mayo Clin Proc, vol. 77, pp. 339-349.
Caplus accession No. 190686-49-8; Brugia malayi strain TRS Labs conle RRAMCA1537 EST; Chemical Abstracts Services; Database Caplus.
Diebold et al., 2004; Innate Antiviral Responses by Means of TLR7-Mediated Recognition of Single Stranded RNA; Science; vol. 303; pp. 1529-1531.
Feroze-Merzoug et al., 2001; Molecular profiling in prostate cancer, Cancer Metastasis Reviews, vol. 20, pp. 165-171.
Fire et al., 1998; Potent and specific genetic interference by double-stranded RNA in Caenorhabditis elegans; nature; vol. 391; pp. 806-811.
Galbraith et al., 1994; Complement Activation and Hemodynamic Changes Following Intravenous Administration of Phosphorothioate Oligonucleotides in the Monkey; Antisense Research and Development; vol. 4, pp. 201-206.
Gao et al., 2007; Nonviral gene delivery: what we know and what is next; The AAPS Journal, vol. 9, No. 1, pp. E92-104, XP02609380.
Gryaznov, 1999; Oligonucleotide N3∝-->P5' phosphoramidates as potential therapeutic agents; Biochimica et Biophysica Acta; vol. 1489, pp. 131-140.
Hardy et al., 2009; Synergistic effects on gene delivery—co-formulation of small disulfide-linked dendritic polycations with Lipofectamine 2000; Organic & Biomolecular Chemistry, vol. 7, No. 4, pp. 789-793, XP002609381.
Hausch et al.; 1998; A novel carboxy-functionalized photocleavable dinucleotide analog for the selection for RNA catalysts; Tetrahedron Letters, vol. 39, No. 34, pp. 6157-6158.
Heindenreich et al., 1993; Chemically modified RNA: approaches and applications; FASEB Journal; vol. 7 No. 1, pp. 90-96.
Herbert et al., The Dictionary of Immunology, Academic Press, 4$^{th}$ edition, 1995.
Herbert et al.; 2005; Lipid modification of GRN163, an N3'-->P5' thio-phosphoramidate oligonucleotide, enhances the potency of telomerase ingibition; Oncogene; vol. 24; pp. 5262-5268.
Heymann, 1990; The immune complex: possible ways of regulating the antibody response; Immunology Today; vol. 11, No. 9, pp. 310-313.

(56) References Cited

OTHER PUBLICATIONS

Hoerr et al., 2000; In vivo application of RNA leads to induction of specific cytotoxic T lymphocytes and antibodies; Eur. J. Immunol., vol. 30, No. 1, pp. 1-7.

Janssen et al., 2003; Role of Toll-Like Receptors in Pathogen Recognition; Clinical microbiology Reviews, vol. 16, No. 4; pp. 637-646.

Kim et al., 2009; VeGF siRNA delivery system using arginine-grafted bioreducible poly(disulfide amine); Molecular Pharmaceutics, vol. 6, No. 3, pp. 718-726, XP002609382.

Kwiatkowski et al., 1984; The 9-(4-Octadecyloxyphenylxanthen)-9-yl-Group. A new Acid-labile Hydroxyl Protective Group and $1^{st}$ Application in the Preparative Reserve-phase Chromatographic Separation of Oligoibonucleotides; Acta Chemica Scandinavica; B38(8); pp. 657-671.

Lo et al., 2008; An endosomolytic Tat peptide produced by incorporation of histidine and cysteine residues as a nonviral vector for DNA transfection; Biomatierials, vol. 29, No. 15, pp. 24408-24414, XP022526913.

Lochmann et al.; 2004; Drug delivery of oligonucleotides by peptides; European Journal of Pharmaceutics and Biopharmaceutics; vol. 58, No. 2, pp. 237-251.

Mateo et al., 1999; An HLA-A2 Polyepitope Vaccine for Melanoma Immunotherapy; J Immunol, vol. 163, pp. 4058-4063.

Matray et al., 1999; Synthesis and properties of RNA analogs—oligoribonucleotide N3'-->P5' phosphoramidates; Nucleic Acids Research; vol. 27, No. 20, pp. 3976-3985.

McKenzie et al., 2000; A potent new class of reductively activated peptide gene delivery agents; Journal of Biological Chemistry, vol. 275, No. 14, pp. 9970-9977, XP002238140.

McKenzie et al., 2000; Low molecular weight disulfide cross-linking peptides as nonviral gene delivery carriers; Bioconjugate Chemistry, vol. 11, No. 6. pp. 901-909, XP002609379.

Milich et al., 1997; The Hepatitis B Virus Core and e Antigens Elicit Different Th Cell Subsets: Antigen Structure Can Affect TH Cell Phenotype; Journal of Virology, vol. 71, No. 3, pp. 2192-2201.

Minks et al., 1979; Structural requirements of Double-stranded RNA for the Activation of 2',5'-Oligo(A) Polymerase and Protein Kinase of Interferon-treated HeLa Cells; The Journal of Biological Chemistry; vol. 254, No. 20; pp. 10180-10183.

Miyata et al., 2004; Block Catiomer Polyplexes with Regulated Densities of charge and Disulfide Cross-Linking Directed to Enhance Gene Expression; Journal of the American Chemical Society, vol. 126, No. 8, pp. 2355-2361, XP002993261.

Nicholson et al., 1988; Accurate in vitro cleavage by Rnase III of phosphothioate-substituted RNA processing signals in bacteriophage T7 early mRNA; Nucleic Acids Res., vol. 16, No. 4, pp. 1577-1591.

Ramazeilles et al., 1994; Antisense phosphorothioate oligonucleotides: Selective killing of the intracellular parasite Leishmania amazonesis; Proc. Natl. Acad. Sci., vol. 91, pp. 7859-7863.

Read et al.; 2003; Vectors based on reducible polycations facilitate intracellular release of nucleic acids; Journal of Gene Medicine, vol. 5 No. 3, pp. 232-245, XP002481542.

Read et al.; 2005; A versatile reducible polycationic-based system for efficient delivery of a broad range of nucleic acids; nucleic acids research, vol. 33 No. 9, pp. 1-16; XP002447464.

Riedl et al., 2002; Priming Th1 Immunity to Voral Core Particles is Facilitated by Trace Amounts of RNA Bound to $1^{st}$ Arginine-Rich Domain; The Journal of Immunology, vol. 168, pp. 4951-4959.

Saenz-Badillos, 2001; RNA as a tumor vaccine: a review of the literature; Exp. Dermatol.; vol. 10, No. 3, pp. 143-154.

Scheel et al., 2003; mRNA as immunostimulatory molecule; Krebsimmuntherapie—Annual Meeting 2003; Abstract (online publication, http://www. Kimt.de/archive/abstracts/htm) Session 5 Abstract 10.

Scheel et al., 2005; Toll-like receptor dependent activation of several human blood cell types by protamine-condensed mRNA, Eur J Immunol, vol. 35, No. 5, pp. 1557-1566.

Scheel et al., 2006; Therapeutic anti-tumor immunity triggered by injections of immunostimulating single-stranded RNA; Eur J Immunol, vol. 36, No. 10, pp. 2807-2816.

Schirrmacher et al., 2000; Intra-pinna anti-tumor vaccination with self-replicating infectious RNA or with DANN encoding a model tumor antigen and a cytokine; Gene Therapy, vol. 7 No. 13, pp. 1137-1147.

Shea et al., 1990, Synthesis, hybridization properties and antiviral activity of lipid-oligodeoxynucleotide conjugates; Nucleic Acids Research; vol. 18, No. 13, pp. 3777-3783.

Takae et al., 2008; PEG-detachable polyplex micelles based on disulfide-linked block catiomers as bioresponsive nonviral gene vectors; Journal of the American Chemical Society, nol. 130, No. 18, pp. 6011-6009, XP002609383.

Teplova et al., 1999; Crystal structure and improved antisense properties of 23'-O-(2-methoxyethyl)-RNA; Nature Structural Biology; vol. 6, No. 6, pp. 535-539.

Tokunaga et al., 2004; Effect of oligopeptides on gene expression: comparison of DNA/peptide and DNA/peptide/liposome complexes; International Journal of Pharmaceutics, vol. 269, No. 1, pp. 71-80, XP002609384.

Trinchieri et al., 2007; Cooperation of Toll-like receptor signals in innate immune defense; Nature Reviews Immunology; vol. 7, Mar. 2007; pp. 179-190.

Zhou et al., 1999; RNA Melanoma Vaccine: Induction of Antitumor Immunity by Human Glycoprotein 100 mRNA Immunization; Human Gene Therapy; vol. 10; pp. 2719-2724.

Machine-generated English translation of EP1564291 (Document B3), May 25, 2012.

"Cell-penetrating peptide," Wikipedia, located at http://en.wikipedia.org/wiki/cell-penetrating_peptide, downloaded on Dec. 11, 2012.

"DOC/Alum Complex," Violin: Vaccine investigation and online information network, located at http://www.violinet.org/vaxjo/vaxjo_detail.php?c_vaxjo_id=49, downloaded on Aug. 28, 2012.

"QS21," Wikipedia, located at http://en.wikipedia.org/wiki/QS21, downloaded on Dec. 11, 2012.

"Ribi vaccine adjuvant," Violin: Vaccine investigation and online information network, located at http://www.violinet.org/vaxjo/vaxjo_detail.php?c_vaxjo_id=21, downloaded on Dec. 17, 2012.

"SPT (Antigen Formulation)," Violin: Vaccine investigation and online information network, located at http://www.violinet.org/vaxjo/vaxjo_detail.php?c_vaxjo_id=72, downloaded on Aug. 21, 2012.

"Virus-like particle," Wikipedia, located at http://en.wikipedia.org/wiki/virus-like_particle, downloaded on Sep. 3, 2012.

Berzofsky et al., "Progress on new vaccine strategies against chronic viral infections," *J Clin Invest.*, 114(4):450-462, 2004.

Cooper et al., "CPG 7909 adjuvant improves hepatitis B virus vaccine seroprotection in antiretroviral-treated HIV-infected adults," *AIDS*, 19:1473-1479, 2005.

Dmitriev, "Bactenecin 7 peptide fragment as a tool for intracellular delivery of a phosphorescent oxygen sensor," *FEBS Journal*, 277:4651-4661, 2010.

Fox, "Squalene emulsions for parenteral vaccine and drug delivery," Molecules, 14:3286-3312, 2009.

Huang et al., "Recent development of therapeutics for chronic HCV infection," *Antiviral Res.*, 71(2-3):351-362, 2006.

Huget et al., "Adjuvant and suppressor activity of the polycation protamine hydrochloride in the primary immune response of mice," *Z Immunitatsforsch Immunobiol.*, 152(3):190-199, 1976.

Kilk, "Cell-penetrating peptides and bioactive cargoes. Strategies and mechanisms," Department of Neurochemistry and Neurotoxicology Arrhenius Laboratories of Natural Sciences Stockholm University, 2004.

Koziel et al., "Hepatitis C virus (HCV)-specific cytotoxic T lymphocytes recognize epitopes in the core and envelope proteins of HCV," *J Virol.*, 67(12):7522-7532, 1993.

Racanelli et al., "Presentation of HCV antigens to naive CD8+T cells: why the where, when, what and how are important for virus control and infection outcome," *Clin Immunol.*, 124(1):5-12, 2007.

Rittner et al., "New basic membrane-destabilizing peptides for plasmid-based gene delivery in Vitro and in Vivo," *Molecular Therapy*, 15(2):104-114, 2002.

(56) References Cited

OTHER PUBLICATIONS

Rollier et al., "Control of heterologous hepatitis C virus infection in chimpanzees is associated with the quality of vaccine-induced peripheral T-helper immune response," *J Virol.*, 78(1):187-196, 2004.
Shiffman et al., "Protein dissociation from DNA in model systems and chromatin," *Nucleic Acids Res.*, 5(9):3409-3426, 1978.
Shirai et al., "An epitope in hepatitis C virus core region recognized by cytotoxic T cells in mice and humans," *J Virol.*, 68(5):3334-3342, 1994.
Sun et al., "Advances in saponin-based adjuvants," *Vaccine*, 27:1787-1796, 2009.
Tan et al., "Strategies for hepatitis C therapeutic intervention: now and next," *Curr Opin Pharmacal.*, 4(5):465-470, 2004.
Wyman et al., "Design, Synthesis, and Characterization of a Cationic Peptide That Binds to Nucleic Acids and Permeabilizes Bilayers," *Biochemistry*, 36:3008-3017, 1997.
Zohra et al., "Effective delivery with enhanced translational activity synergistically accelerates mRNA-based transfection," *Biochem Biophys Res Commun.*, 358(1):373-378, 2007.
Heil, Florian, et al., "Species-Specific Recognition of Single-Stranded RNA via Toll-like Receptor 7 and 8", Science, vol. 303, (2004), pp. 1526-1529.
Parkinson, John, et al., "A Transcriptomic Analysis of the Phylum Nematoda", Nature Genetics, vol. 36, No. 12, (2004), pp. 1259-1267.
Blaxter, Mark, et al., "Pathogen Genomes and Human Health: the *Brugia malayi* Genome Project: Expressed Sequence Tags and Gene Discovery", Transactions of the Royal Society of Tropical Medicine and Hygeine, vol. 96, (2002), pp. 7-17.
Musculus Genomic Clone, EBI Database, XP-002526637, Accession No. CZ193289, Feb. 11, 2005.
Arabidopsis thaliana cDNS Clone, XP-002526637, Accession No. BP836659, Jan. 22, 2005.
Dog Eye Lens, XP-002526638, Accession No. DN868844, Apr. 25, 2005.
"Brugia malayi Strain TRS Labs Clone RRAMCA1537", & Database Caplus, Accession No. 190686-49-8 abstract.
Alexopoulou et al., "Recognition of double-stranded RNA and activation of NF-kB y toll-like receptor 3", *Nature*, 413:732-738, 2001.
Grzelinski et al., "RNA interference-mediated gene silencing of pleiotrophin through polyethylenimine-complexed small interfering RNAs in vivo exerts antitumoral effects in glioblastoma xenogafts", *Human Gene Therapy*, 17:751-766, 2006.
Hornung et al., "Sequence-specific potent induction of IFN-alpha by short interfering RNA in plasmacytoid dendritic cells through TLR7", *Nature Medicine*, 11(3):263-270, 2005.
Judge et al., "Design of noninflammatory synthetic siRNA mediating potent gene silencing in vivo", *Molecular Therapy*, 13(3):494-505, 2006.
Ma et al., "Cationic lipids enhance siRNA-mediated interferon response in mice", *Biochemical and Biophysical Research Communications*, 330(3):755-759, 2005.

\* cited by examiner

NUCLEIC ACIDS COMPRISING FORMULA $(N_uG_lX_mG_nN_v)_a$ AND DERIVATIVES THEREOF AS IMMUNOSTIMULATING AGENT/ADJUVANT

RELATED APPLICATIONS

This application is a national stage application (under 35 U.S.C. §371) of PCT/EP2009/000546, filed Jan. 28, 2009, which claims benefit of European application 08001827.8, filed Jan. 31, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_22122_00032_US. The size of the text file is 40 KB, and the text file was created on Feb. 3, 2010.

The present invention relates to nucleic acids of the general formula (I): $(N_uG_lX_mG_nN_v)_a$ and derivatives thereof as an immunostimulating agent/adjuvant and to compositions containing same, optionally comprising an additional adjuvant. The present invention furthermore relates to a pharmaceutical composition or to a vaccine, each containing nucleic acids of formula (I) above and/or derivatives thereof as an immunostimulating agent, and optionally at least one additional pharmaceutically active component, e.g. an antigenic agent. The present invention relates likewise to the use of the pharmaceutical composition or of the vaccine for the treatment of cancer diseases, infectious diseases, allergies and autoimmune diseases etc. Likewise, the present invention includes the use of nucleic acids of the general formula (I): $(N_uG_lX_mG_nN_v)_a$ and/or derivatives thereof for the preparation of a pharmaceutical composition for the treatment of such diseases.

In both conventional and genetic vaccination, the problem frequently occurs that only a small and therefore frequently inadequate immune response is brought about in the organism to be treated or inoculated. For this reason, so-called adjuvants are frequently added to vaccines or pharmaceutically active components, that is to say substances or compositions that are able to increase and/or influence in a targeted manner an immune response, for example to an antigen. For example, it is known that the effectiveness of some injectable medicinal active ingredients can be improved significantly by combining the active ingredient with an adjuvant which is capable of influencing the release of the active ingredient into the host cell system and optionally its uptake into the host cells. In this manner it is possible to achieve an effect that is comparable to the periodic administration of many small doses at regular intervals. The term "adjuvant" conventionally refers in this context to a compound or composition that serves as a carrier or auxiliary substance for immunogens and/or other pharmaceutically active compounds. Typically, the term "adjuvant" is to be interpreted in a broad sense and refers to a broad spectrum of substances or stratagerms, that are able to increase the immunogenicity of antigens incorporated into or coadministered with an adjuvant in question. Adjuvants furthermore may be divided, without being limited thereto, into immune potentiators, antigenic delivery systems or even combinations thereof.

A number of compounds and compositions have been proposed as adjuvants in the art, for example Freund's adjuvant, metal oxides (aluminium hydroxide, etc.), alum, inorganic chelates or salts thereof, various paraffin-like oils, synthetic resins, alginates, mucoids, polysaccharide compounds, caseinates, as well as compounds isolated from blood and/or blood clots, such as, for example, fibrin derivatives, etc. However, such adjuvants in most cases produce undesirable side-effects, for example skin irritation and inflammation at the site of administration. Even toxic side-effects, in particular tissue necroses, are also observed in some cases. Unfortunately, in most cases these known adjuvants bring about only inadequate stimulation of the cellular immune response, because only B-cells are activated.

Compounds isolated from animals, such as, for example, gelatin, are generally not suitable as adjuvants for the purpose of immunostimulation. Although such compounds usually do not exhibit a negative effect on the host organism or the host cells in question, they typically migrate too rapidly from the injection site into the host organism or into the host cells, so that the properties generally desired for an adjuvant, such as, for example, delayed release of an active ingredient optionally injected together with the adjuvant, etc., are seldom achieved. Such rapid distribution can, in some cases, be counteracted with tannins or other (inorganic) compounds. The metabolism of such additional compounds and their whereabouts in the body has not been fully explained, however. In this case too, therefore, it is reasonable to assume that these compounds accumulate in the debris and thus considerably interfere with the filtration mechanisms, for example the kidney, liver and/or spleen cells. Also, the property of gelatin of swelling when administered parenterally can lead to unpleasant side-effects under in vivo conditions, such as, for example, swelling, in particular at the site of administration, and to a feeling of illness.

In the case of compounds isolated from blood and/or blood clots, such as, for example, fibrin derivatives, etc., immunostimulating effects have typically been demonstrated. However, most of these compounds, when administered as adjuvants, are not suitable for that purpose because of their side-effects on the immune system (which occur in parallel with the required immunogenic properties). For example, many of these compounds are categorised as allergenic and in some circumstances lead to an excess reaction of the immune system which far exceeds the desired degree. These compounds are therefore likewise unsuitable as adjuvants for immunostimulation for the mentioned reasons.

Accordingly, it is a first object of the present invention to provide immunostimulating agents, which act as adjuvants and stimulate the innate immune system, preferably if administered in combination with other biologically active compounds, in particular if administered together with immune-modulating compounds, more preferably in combination with compounds, which specifically stimulate the adaptive immune system, such as antigens.

In this context, it is known that (unspecific) immunostimulating effects can also be produced by directly using nucleic acids to trigger an unspecific (i.e. innate) immune response, e.g. with bacterial CpG-DNA sequences, which not only serve for genetic information. For example, DNA is known to play a central role in the production of unspecific immune responses. Bacterial DNA, for example, is known to act as "danger" signal to alert immune cells, such as macrophages and dendritic cells and to promote protective Th1 polarized T cell immune responses. An immunostimulating action appears to result from the presence of unmethylated CG (nucleic acid) motifs, and such CpG-DNA has therefore been proposed as an immunostimulating agent as such (see e.g. U.S. Pat. No. 5,663,153). CpG-DNA directly causes activation of members of the innate immune system yielding in up-regulation of co-stimulatory molecules and pro-inflammatory cytokines. This immunostimulating property of DNA can also be achieved by DNA oligonucleotides which are stabilized by phosphorothioate modification (see e.g. U.S. Pat. No. 6,239,116). Such immunostimulating DNA may also be combined with further immunostimulating compounds. E.g., U.S. Pat. No. 6,406,705 discloses immunostimulating compositions which contain a synergistic combination of a CpG oligodeoxyribonucleotide and a non-nucleic acid compound to exert a stimulating effect on the innate immune system.

However, the use of DNA to exert an unspecific immune response can be less advantageous from several points of view. DNA is decomposed only relatively slowly in vivo so that, when immunostimulating (foreign) DNA is used, the formation of anti-DNA antibodies may occur, which has been confirmed in an animal model in mouse (Gilkeson et al. J. Clin. Invest. 1995, 95: 1398-1402). Persistence of (foreign) DNA in the organism can thus lead to over-activation of the immune system, which is known in mice to result in splenomegaly (Montheith et al., Anticancer Drug Res. 1997, 12(5): 421-432). Furthermore, (foreign) DNA can interact with the host genome and cause mutations, in particular by integration into the host genome. For example, insertion of the introduced (foreign) DNA into an intact gene can occur, which represents a mutation which can impede or even eliminate completely the function of the endogenous gene. As a result of such integration events enzyme systems that are vital to the cell can be destroyed. However, there is also a risk that the cell so changed will be transformed into a degenerate state. Such transformation may occur e.g. if, by the integration of the (foreign) DNA, a gene that is critical for the regulation of cell growth is changed. Therefore, in processes known hitherto, a possible risk of cancer formation cannot be ruled out when using (foreign) DNA as immunostimulating agent.

It is therefore generally more advantageous to use specific RNA molecules as a compound to elicit an (unspecific) response of the innate immune system. In this context, the innate immune system as part of the immune system is the dominant system of host defense in most organisms and comprises barriers such as humoral and chemical barriers including, e.g., inflammation, the complement system and cellular barriers. Additionally, the innate immune system is based on a small number of receptors, called pattern recognition receptors or pathogen associated molecular pattern receptors (PAMP-receptors), such as members of the Toll-like receptor (TLR) family (see e.g. Trinchieri and Sher, Nature reviews, Immunology, Volume 7, March 2007). Such TLRs are transmembrane proteins which recognize ligands of the extracellular milieu or of the lumen of endosomes. Following ligand-binding they transduce the signal via cytoplasmic adaptor proteins which leads to triggering of a host-defense response and entailing production of antimicrobial peptides, proinflammatory chemokines and cytokines, antiviral cytokines, etc. (see e.g. Meylan, E., J. Tschopp, et al., (2006). "Intracellular pattern recognition receptors in the host response." Nature 442(7098): 39-44).

To date, at least 10 members of Toll-like receptors (TLRs) have been identified in human and 13 in mice, which are in part identified with respect to their mode of action. In humans, those Toll-like receptors (TLRs) include TLR1-TLR2 (known ligand: Triacyl lipopeptide), TLR1-TLR6 (known ligand: Diacyl lipopeptide), TLR2 (known ligand: Peptidoglycan), TLR3 (known ligand: dsRNA), TLR4 (known ligand: LPS (lipopolysachharide) of Gram-negative bacteria)), TLR5 (known ligand: bacterial flagellin(s)), TLR7/8 (known ligands: imidazoquinolines, guanosine (guanine) analogs and ssRNA), TLR9 (known ligands: CpG DNA of bacteria, viruses and protozoans and malaria pigment hemozoin (product of digestion of haemoglobin)) and TLR10. After recognition of microbial pathogens, these TLRs typically trigger intracellular signalling pathways that result in induction of inflammatory cytokines (e.g. TNF-alpha, IL-6, IL-1-beta and IL-12), type I interferon (IFN-beta and multiple IFN-alpha) and chemokines (Kawai, T. and S. Akira (2006). "TLR signaling." Cell Death Differ 13(5): 816-25).

In this context, RNAs are advantageous for several reasons. E.g., as known today and mentioned above, ssRNA is capable of binding to TLR-7/-8 receptors and dsRNA is capable of binding to TLR receptors and thereby exerting an immunostimulating effect. Furthermore, RNA as immunostimulating agent typically has a substantially shorter half-life in vivo than DNA, thereby avoiding the above mentioned drawbacks of DNA. Nevertheless, the use of those specific RNA molecules known as immunostimulating agents in the art also has some limitations. For example, the specific RNA sequences disclosed hitherto in the art exhibit only limited immunostimulating capacities in vivo. This may require an increased amount of RNA for immunostimulation, which, regardless of the increased costs owing to the increased amounts of RNA to be administered, involves the risk of the mostly undesirable side-effects described generally hereinbefore, for example irritation and inflammation at the site of administration, even if this may be the case for a limited time window. Also, toxic side-effects cannot be ruled out when large amounts of the immunostimulating agent are administered.

A further limitation is the low induction of type I interferons (e.g. IFNalpha and IFNbeta) by known immunostimulating RNA molecules which are important inducers of antiviral and antiproliferative activities and cytolytic activity in lymphocytes, natural killer cells and macrophages.

Known immunostimulating dsRNA molecules are for instance poly A:U and poly I:C. The disadvantage of these immunostimulating dsRNA molecules, however, is their undefined length, which may lead to non-predictable molecular structures and thereby to aggregates. Such aggregates may further lead to undesired side effects such as occlusion of blood vessels or undue immunostimulation at the site of injection. Additionally, such non-predictable molecular structures represent a problem in daily laboratory and production routines as no adequate quality control may be carried out due to variable product parameters. Here, a defined nucleic acid molecule exhibiting a defined length and structure and being suitable as an adjuvant is preferred for pharmaceutical applications.

Despite the success of RNA demonstrated hitherto, there is therefore a continued need for, and considerable interest in, improved immunostimulating agents which may exert by their own an immune response of the patient's innate immune system. Accordingly, it is a second object of the invention to provide immunostimulating agents which exert an unspecific immune response by activating the patient's innate immune system.

Both objects of the present invention are solved by the provision of nucleic acid molecules of the following generic formula (I). These inventive nucleic acid molecules activate the innate immune system, thus eliciting an unspecific immune response. As adjuvants (e.g. as component of a vaccine), they may additionally support the immunostimulating activity of a second compound specifically activating the adaptive immune system.

The present invention provides a nucleic acid (molecule) of formula (I):

$$(N_uG_lX_mG_nN_v)_a,$$

wherein:
G is guanosine (guanine), uridine (uracil) or an analogue of guanosine (guanine) or uridine (uracil), preferably guanosine (guanine) or an analogue thereof;
X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, G is guanosine (guanine) or an analogue thereof,
    when l>1, at least 50% of these nucleotides (nucleosides) are guanosine (guanine) or an analogue thereof;
m is an integer and is at least 3;
  wherein when m=3, X is uridine (uracil) or an analogue thereof, and
    when m>3, at least 3 successive uridines (uracils) or analogues of uridine (uracil) occur;
n is an integer from 1 to 40,
  wherein when n=1, G is guanosine (guanine) or an analogue thereof,
    when n>1, at least 50% of these nucleotides (nucleosides) are guanosine (guanine) or an analogue thereof;
u,v may be independently from each other an integer from 0 to 50,
  preferably wherein when u=0, v≥1, or
    when v=0, u≥1;
wherein the nucleic acid molecule of formula (I) according to the invention has a length of at least 50 nucleotides, preferably of at least 100 nucleotides, more preferably of at least 150 nucleotides, even more preferably of at least 200 nucleotides and most preferably of at least 250 nucleotides.

The molecule $(N_uG_lX_mG_nN_v)_a$ of formula (I) according to the invention is typically a nucleic acid, which may be in the form of any DNA or RNA, preferably, without being limited thereto, a circular or linear DNA or RNA, a single- or a double-stranded DNA or RNA (which may also be regarded as an DNA or RNA due to non-covalent association of two single-stranded DNAs or RNAs) or a partially double-stranded DNA or RNA (which is typically formed by a longer and at least one shorter single-stranded DNA or RNA molecule or by at least two single-stranded DNA or RNA-molecules, which are about equal in length, wherein one or more single-stranded DNA or RNA molecules are in part complementary to one or more other single-stranded DNA or RNA molecules and thus form a double-stranded RNA in this region), e.g. a (partially) single-stranded DNA or RNA, mixed with regions of a (partially) double-stranded DNA or RNA. Preferably, the nucleic acid molecule of formula (I) according to the invention may be in the form of a single- or a double-stranded DNA or RNA, more preferably a partially double-stranded DNA or RNA. It is also preferred that the nucleic acid molecule of formula (I) according to the invention is in the form of a mixture of a single-stranded nucleic and double stranded DNA or RNA.

It is particularly advantageous, if the inventive nucleic acid $(N_uG_lX_mG_nN_v)_a$ of formula (I) according to the invention is a partially double-stranded nucleic acid molecule, since such a (partially double-stranded) inventive nucleic acid molecule according to formula (I) (or of formula (Ia), (II) (IIIa), (IIIb), (IIIa) and/or (IIIb) as defined below), can positively stimulate the innate immune response in a patient to be treated by addressing the PAMP-(pathogen associated molecular pattern) receptors for single-stranded RNA (TLR-7 and TLR-8) as well as the PAMP-receptors for double-stranded RNA (TLR-3, RIG-1 and MDA-5). Receptors TLR-3, TLR-7 and TLR-8 are located in the endosome and are activated by RNA taken up by the endosome. In contrast, RIG-I and MDA-5 are cytoplasmic receptors, which are activated by RNA, which was directly taken up into the cytoplasm or which has been released from the endosomes (endosomal release or endosomal escape). Accordingly, any partially double-stranded inventive nucleic acid $(N_uG_lX_mG_nN_v)_a$ of formula (I) (or (a partially double-stranded) inventive nucleic acid molecule according to formula (I) (and (Ia), (II) (IIIa), (IIIb), (IIIa) and (IIIb) as defined below)) is capable of activating different signal cascades of immunostimulation and thus leads to an innate immune response or enhances such a response significantly.

The structure $(N_uG_lX_mG_nN_v)_a$ of formula (I) according to the present invention comprises the element $G_lX_mG_n$ as a core structure and additionally the bordering elements $N_u$ and/or $N_v$, wherein the whole element $N_uG_lX_mG_nN_v$ may occur repeatedly, i.e. at least once, as determined by the integer a. In this context, the inventors surprisingly found, that a molecule according to formula (I) according to the invention, i.e. having the structure $(N_uG_lX_mG_nN_v)_a$ as defined above, leads to an increased innate immune response in a patient, which is particularly indicated by an increase of IFNalpha release, when compared to administration of the core structure $G_lX_mG_n$ as such. Furthermore, a molecule comprising the above core structure $G_lX_mG_n$ can be amplified in bacterial organisms with a significantly better yield, when it is bordered by a repetitive element $N_u$ and/or $N_v$ as defined in formula (I). This molecule design is particularly advantageous when preparing a molecule according structure $(N_uG_lX_mG_nN_v)_a$ of formula (I) as defined above by using in vitro transcription methods instead of solid phase synthesis methods as known in the art, which are typically limited to a specific size of nucleic acids.

The core structure $G_lX_mG_n$ of formula (I) according to the invention is defined more closely in the following:

G in the nucleic acid molecule of formula (I) according to the invention is a nucleotide or deoxynucleotide or comprises a nucleoside, wherein the nucleotide (nucleoside) is guanosine (guanine) or uridine (uracil) or an analogue thereof, more preferably guanosine (guanine) or an analogue thereof. In this connection, guanosine (guanine) or uridine (uracil) nucleotide (nucleoside) analogues are defined as non-natively occurring variants of the naturally occurring nucleotides (nucleoside) guanosine (guanine) and uridine (uracil). Accordingly, guanosine (guanine) or uridine (uracil) analogues are typically chemically derivatized nucleotides (nucleoside) with non-natively occurring functional groups or components, which are preferably added to, modified or deleted from the naturally occurring guanosine (guanine) or uridine (uracil) nucleotide or which substitute the naturally occurring functional groups or components of a naturally occurring guanosine (guanine) or uridine (uracil) nucleotide. Accordingly, each functional group or component of the naturally occurring guanosine (guanine) or uridine (uracil) nucleotide may be modified or deleted therefrom, namely the base component, the sugar (ribose) component, any naturally occurring functional side group and/or the phosphate component forming the oligonucleotide's backbone. The phosphate moieties may be substituted by e.g. phosphoramidates, phosphorothioates, peptide nucleotides, methylphosphonates etc., however, naturally occurring phosphodiester backbones still being preferred in the context of the present invention. Additionally, the sugar (ribose) component is selected from a desoxyribose, particularly the nucleic acid is an RNA as defined above, wherein the sugar (ribose) component is selected from a desoxyribose.

Accordingly, analogues of guanosine (guanine) or uridine (uracil) include, without implying any limitation, any naturally occurring or non-naturally occurring guanosine (guanine) or uridine (uracil) that has been altered chemically, for example by acetylation, methylation, hydroxylation, etc., including, for example, 1-methyl-guanosine (guanine), 2-methyl-guanosine (guanine), 2,2-dimethyl-guanosine (guanine), 7-methyl-guanosine (guanine), dihydro-uridine (uracil), 4-thio-uridine (uracil), 5-carboxymethylaminomethyl-2-thio-uridine (uracil), 5-(carboxy-hydroxylmethyl)-uridine (uracil), 5-fluoro-uridine (uracil), 5-bromo-uridine (uracil), 5-carboxymethylaminomethyl-uridine (uracil), 5-methyl-2-thio-uridine (uracil), N-uridine (uracil)-5-oxyacetic acid methyl ester, 5-methylanninomethyl-uridine (uracil), 5-methoxyaminomethyl-2-thio-uridine (uracil), 5'-methoxycarbonylmethyl-uridine (uracil), 5-methoxy-uridine (uracil), uridine (uracil)-5-oxyacetic acid methyl ester, uridine (uracil)-5-oxyacetic acid (v). The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642, the disclosures of which are incorporated by reference herein in their entirety. In the case of an analogue as described above, preference is given according to the invention especially to those analogues that increase the immunogenity of the nucleic acid molecule of formula (I) according to the invention and/or do not interfere with a further modification that has been introduced. At least one guanosine (guanine) or uridine (uracil) or an analogue thereof can occur in the core structure elements $G_l$ and/or $G_n$, optionally at least 10%, 20%, 30%, 40%, 50%, 60%, 70%, 80% 90% or even 100% of the nucleotides of the core structure elements $G_l$ and/or $G_n$ are a naturally occurring guanosine (guanine), a naturally occurring uridine (uracil), and/or an analogue thereof and/or exhibit properties of an analogue thereof as defined herein. Preferably, the core structure element $G_l$ and/or $G_n$ contains at least one analogue of a naturally occurring guanosine (guanine) and/or a naturally occurring uridine (uracil) at all. Most preferably, all nucleotides (nucleosides) of these core structure elements $G_l$ and/or $G_n$ are analogues, which may—most preferably—be identical analogues for the same type of nucleotides (nucleosides) (e.g. all guanosine (guanine) nucleotides are provided as 1-methyl-guanosine (guanine)) or they may be distinct (e.g. at least two different guanosin analogues substitute the naturally occurring guanosin nucleotide).

The number of nucleotides (nucleosides) of core structure element G ($G_l$ and/or $G_n$) in the nucleic acid molecule of formula (I) according to the invention is determined by l and n. l and n, independently of one another, are each an integer from 1 to 100, 1 to 90, 1 to 80, 1 to 70, 1 to 60, preferably 1 to 50, yet more preferably 1 to 40, and even more preferably 1 to 30, wherein the lower limit of these ranges may be 1, but alternatively also 2, 3, 4, 5, 6, 7, 8, 9, 10, 11, 12, 13, 14, 15, 16, 17, 18, 19, 20, 21, 22, 23, 24, 25, 26, 27, 28, 29, 30, or even more. Preferably, for each integer, when l and/or n=1, G is guanosine (guanine) or an analogue thereof, and when l or n>1, at least 50%, more preferably at least 50%, 60%, 70%, 80%, 90% or even 100% of the nucleotides (nucleosides) of core structure element G ($G_l$ and/or $G_n$) are guanosine (guanine) or an analogue thereof. For example, without implying any limitation, when l or n=4, $G_l$ and/or $G_n$ can be, for example, a GUGU, GGUU, UGUG, UUGG, GUUG, GGGU, GGUG, GUGG, UGGG or GGGG, etc.; when l or n=5, $G_l$ and/or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide (nucleoside) of core structure elements $G_l$ and/or $G_n$ directly adjacent to $X_m$ in the nucleic acid molecule of formula (I) according to the invention is preferably not an uridine (uracil) or an analogue thereof. More preferably nucleotides (nucleosides) of core structure elements $G_l$ and/or $G_n$ directly adjacent to $X_m$ in the nucleic acid molecule of formula (I) according to the invention are at least one guanosine (guanine) or an analogue thereof, more preferably a stretch of at least 2, 3, 4, 5, 6, 7, 8, 9, 10, 11, 12, 13, 14, 15, 16, 17, 18, 19 or even 20 or more guanosines (guanines) or an analogue thereof. Additionally, a nucleotide of core structure elements $G_l$ and/or $G_n$ directly adjacent to N, e.g. $N_u$, and/or $N_v$ (or $N_{w1}$, or $N_{w2}$ as defined below) in the nucleic acid molecule of formula (I) according to the invention is preferably not an uridine (uracil) or an analogue thereof. More preferably, nucleotides (nucleosides) of core structure elements $G_l$ and/or $G_n$ directly adjacent to N, e.g. $N_u$, and/or $N_v$ (or $N_{w1}$ or $N_{w2}$ as defined below) in the nucleic acid molecule of formula (I) according to the invention are at least one guanosine (guanine) or an analogue thereof, more preferably a stretch of at least 2, 3, 4, 5, 6, 7, 8, 9, 10, 11, 12, 13, 14, 15, 16, 17, 18, 19 or even 20 or more guanosines (guanines) or an analogue thereof.

The term "identity" in the present application means that the sequences are compared in relation to a reference sequence and the percentage identity is determined by comparing them. For example, in order to determine the percentage identity of two nucleic acid sequences, the sequences can first be arranged relative to one another (alignment) in order to permit subsequent comparison of the sequences. To this end, for example, gaps can be introduced into the sequence of the first nucleic acid sequence and the nucleotides can be compared with the corresponding position of the second nucleic acid sequence. When a position in the first nucleic acid sequence is occupied with the same nucleotide as in a position in the second sequence, then the two sequences are identical at that position. The percentage identity between two sequences is a function of the number of identical positions divided by the sequences. If, for example, a specific sequence identity is assumed for a particular nucleic acid in comparison with a reference nucleic acid having a defined length, then this percentage identity is indicated relatively in relation to the reference nucleic acid. Therefore, starting, for example, from a nucleic acid sequence that has 50% sequence identity with a reference nucleic acid sequence having a length of 100 nucleotides, that nucleic acid sequence can represent a nucleic acid sequence having a length of 50 nucleotides that is wholly identical with a section of the reference nucleic acid sequence having a length of 50 nucleotides. It can, however, also represent a nucleic acid sequence having a length of 100 nucleotides that has 50% identity, that is to say in this case 50% identical nucleic acids, with the reference nucleic acid sequence over its entire length. Alternatively, that nucleic acid sequence can be a nucleic acid sequence having a length of 200 nucleotides that, in a section of the nucleic acid sequence having a length of 100 nucleotides, is wholly identical with the reference nucleic acid sequence having a length of 100 nucleotides. Other nucleic acid sequences naturally fulfil these criteria equally.

The determination of the percentage identity of two sequences can be carried out by means of a mathematical algorithm. A preferred but non-limiting example of a mathematical algorithm which can be used for comparing two sequences is the algorithm of Karlin et al. (1993), PNAS USA, 90:5873-5877. Such an algorithm is integrated into the NBLAST program, with which sequences having a desired identity with the sequences of the present invention can be identified. In order to obtain a gapped alignment as described above, the "Gapped BLAST" program can be used, as described in Altschul et al., (1997), Nucleic Acids Res, 25:3389-3402. When using BLAST and Gapped BLAST programs, the default parameters of the particular program (e.g. NBLAST) can be used. The sequences can further be aligned using version 9 of GAP (global alignment program) from "Genetic Computing Group", using the default (BLOSUM62) matrix (values −4 to +11) with a gap open penalty of −12 (for the first zero of a gap) and a gap extension penalty of −4 (for each additional successive zero in the gap). After the alignment, the percentage identity is calculated by expressing the number of correspondences as a percentage of the nucleic acids in the claimed sequence. The described methods for determining the percentage identity of two nucleic acid sequences can also be applied correspondingly to amino acid sequences using the appropriate programs.

Likewise preferably, for formula (I), when l or n>1, at least 60%, 70%, 80%, 90% or even 100% of the nucleotides (nucleosides) of the core structure elements G, and/or G, are guanosine (guanine) or an analogue thereof, as defined above. The remaining nucleotides (nucleosides) to 100% in the core structure elements $G_l$ and/or $G_n$ (when guanosine (guanine) constitutes less than 100% of these nucleotides (nucleosides)) may then be uridine (uracil) or an analogue thereof, as defined hereinbefore.

X, particularly $X_m$, in the nucleic acid molecule of formula (I) according to the invention is also a core structure element and is a nucleotide or deoxynucleotide or comprises a nucleoside, wherein the nucleotide (nucleoside) is typically selected from guanosine (guanine), uridine (uracil), adenosine (adenine), thymidine (thymine), cytidine (cytosine) or an analogue thereof, preferably uridine (uracil) or an analogue thereof. In this connection, nucleotide (nucleoside) analogues are defined as non-natively occurring variants of naturally occurring nucleotides (nucleosides). Accordingly, analogues are chemically derivatized nucleotides (nucleosides) with non-natively occurring functional groups, which are preferably added to or deleted from the naturally occurring nucleotide (nucleoside) or which substitute the naturally occurring functional groups of a nucleotide (nucleoside). Accordingly, each component of the naturally occurring nucleotide may be modified, namely the base component, the sugar (ribose or desoxyribose) component and/or the phosphate component forming the oligonucleotide's backbone. The phosphate moieties may be substituted by e.g. phosphoramidates, phosphorothioates, peptide nucleotides, methylphosphonates etc., wherein, however, the naturally occurring phosphodiester backbone is still preferred. Preferably, at least 10%, more preferably at least 20%, more preferably at least 30%, more preferably at least 50%, more preferably at least 70% and even more preferably at least 90% of all "X" nucleotides may exhibit properties of an analogue as defined herein, if the inventive nucleic acid contains at least one analogue at all. The analogues substituting a specific nucleotide type within the core structure element "$X_m$" may be identical, e.g. all cytidine (cytosine) nucleotides (nucleosides) occurring in the core structure element "$X_m$" are formed by a specific cytidine (cytosine) analogue, e.g. 2-thio-cytidine (cytosine), or they may be distinct for a specific nucleotide (nucleosides), e.g. at least two distinct cytidine (cytosine) analogues are contained within the core structure element "$X_m$".

Analogues of guanosine (guanine), uridine (uracil), adenosine (adenine), thymidine (thymine), cytidine (cytosine) include, without implying any limitation, any naturally occurring or non-naturally occurring guanosine (guanine), uridine (uracil), adenosine (adenine), thymidine (thymine) or cytidine (cytosine) that has been altered chemically, for example by acetylation, methylation, hydroxylation, etc., including 1-methyl-adenosine (adenine), 2-methyl-adenosine (adenine), 2-methylthio-N-6-isopentenyl-adenosine (adenine), N6-methyl-adenosine (adenine), N6-isopentenyl-adenosine (adenine), 2-thio-cytidine (cytosine), 3-methyl-cytidine (cytosine), 4-acetyl-cytidine (cytosine), 2,6-diaminopurine, 1-methyl-guanosine (guanine), 2-methyl-guanosine (guanine), 2,2-dimethyl-guanosine (guanine), 7-methyl-guanosine (guanine), inosine, 1-methyl-inosine, dihydro-uridine (uracil), 4-thio-uridine (uracil), 5-carboxymethylaminomethyl-2-thio-uridine (uracil), 5-(carboxyhydroxylmethyl)-uridine (uracil), 5-fluoro-uridine (uracil), 5-bromo-uridine (uracil), 5-carboxymethylaminomethyl-uridine (uracil), 5-methyl-2-thio-uridine (uracil), N-uridine (uracil)-5-oxyacetic acid methyl ester, 5-methylaminomethyl-uridine (uracil), 5-methoxyaminomethyl-2-thio-uridine (uracil), 5'-methoxycarbonylmethyl-uridine (uracil), 5-methoxy-uridine (uracil), uridine (uracil)-5-oxyacetic acid methyl ester, uridine (uracil)-5-oxyacetic acid (v), queosine, beta-D-mannosyl-queosine, wybutoxosine, and inosine. The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. No. 5,262,530 and U.S. Pat. No. 5,700,642. In the case of an analogue as described above, particular preference is given according to the invention to those analogues of nucleotides (nucleosides) that increase the immunogenicity of the nucleic acid molecule of formula (I) according to the invention and/or do not interfere with a further modification that has been introduced.

The number of core structure element X in the nucleic acid molecule of formula (I) according to the invention is determined by m. m is an integer and is typically at least 3, 4, 5, 6, 7, 8, 9, 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200, or even more, wherein when m=3, X is uridine (uracil) or an analogue thereof, and when m>3, at least 3 or more directly successive uridines (uracils) or an analogue thereof occur in the element X of formula (I) above. Such a sequence of at least 3 or more directly successive uridines (uracils) is referred to in connection with this application as a "monotonic uridine (uracil) sequence". A monotonic uridine (uracil) sequence typically has a length of at least 3, 4, 5, 6, 7, 8, 9 or 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200 uridines (uracils) or optionally analogues of uridine (uracil) as defined above. Such a monotonic uridine (uracil) sequence occurs at least once in the core structure element X of the nucleic acid molecule of formula (I) according to the invention. It is therefore possible, for example, for 1, 2, 3, 4, 5 or more monotonic uridine (uracil) sequences having at least 3 or more uridines (uracils) or analogues thereof to occur, which monotonic uridine (uracil) sequences can be interrupted in the core structure element X by at least one guanosine (guanine), adenosine (adenine), thymidine (thymine), cytidine (cytosine) or an analogue thereof, preferably 2, 3, 4, 5 or more. For example, when m=3, $X_m$ is a UUU. When m=4, $X_m$, can be, for example, without implying any limitation, a UUUA, UUUG, UUUC, UUUU, AUUU, GUUU or CUUU, etc. When n=10, $X_m$ can be, for example, without implying any limitation, a UUUAAUUUUC (SEQ ID NO: 120), UUUUGUUUUA (SEQ ID NO: 121), UUUGUUUGUU (SEQ ID NO: 122), UUGUUUUGUU (SEQ ID NO: 123), UUUUUUUUUU (SEQ ID NO: 124), etc. The nucleotides of $X_m$ adjacent to $G_l$ or $G_n$ of the nucleic acid molecule of formula (I) according to the invention preferably comprise uridine (uracil) or analogues thereof. When m>3, typically at least 50%, preferably at least 60%, 70%, 80%, 90% or even 100%, of the nucleotides of $X_m$ are uridine (uracil) or an analogue thereof, as defined above. The remaining nucleotides of $X_m$ to 100% (where there is less than 100% uridine (uracil) in the sequence $X_m$ are then guanosine (guanine), uridine (uracil), adenosine (adenine), thymidine (thymine), cytidine (cytosine) or an analogue thereof, as defined above.

The inventive nucleic acid according formula (I) above also contains bordering element N. The bordering element N is typically a nucleic acid sequence having a length of about 4 to 50, preferably of about 4 to 40, more preferably of about 4 to 30 nucleotides (nucleosides), even more preferably of about 4 to 20 nucleotides (nucleosides), wherein the lower limit of these ranges alternatively also may be 5, 6, 7, 8, 9, 10, or more. Preferably, the nucleotides (nucleosides) of each N are independently selected from guanosine (guanine), uridine (uracil), adenosine (adenine), thymidine (thymine), cytidine (cytosine) and/or an analogue thereof. In other words, bordering element N in the nucleic acid molecule of formula (I) according to the present invention may be a sequence, which may be composed of any (random) sequence, available in the art, each N independently selected from guanosine (guanine), uridine (uracil), adenosine (adenine), thymidine (thymine), cytidine (cytosine) and/or an analogue of these nucleotides, or from a homopolymer of these nucleotides (nucleosides), in each case provided, that such a sequence has a length of about 4 to 50, preferably of about 4 to 40, more preferably of about 4 to 30 nucleotides (nucleosides) and even more preferably of about 4 to 30 or 4 to 20 nucleotides (nucleosides) according to the above definition.

According to a specific embodiment, N may be a nucleic acid sequence within the above definitions, wherein the sequence typically comprises not more than 2 identical nucleotides (nucleosides) as defined above in a directly neighboring position, i.e. the sequence typically comprises no stretches of more than two identical nucleotides (nucleosides) selected from adenosine (adenine), cytidine (cytosine), uridine (uracil) and/or guanosine (guanine), and/or an analogue thereof (i.e. a stretch of "aa", "cc", "uu", "gg" and/or an analogue thereof), more preferably no such stretch, i.e. no identical nucleotides (nucleosides) as defined above in a directly neighboring position. Additionally or alternatively, N may be a nucleic acid sequence within the above definitions, wherein the sequence typically comprises a content of adenosine (adenine) or an analogue thereof preferably of about 0 to 50%, 5 to 45%, or to 40%, more preferably of about 15 to 35%, even more preferably of about 20 to 30%, and most preferably of about 25%; a content of uridine (uracil) or an analogue thereof preferably of about 0 to 50%, 5 to 45%, or 10 to 40%, more preferably of about 15 to 35%, even more preferably of about 20 to 30%, and most preferably of about 25%; a content of cytidine (cytosine) or an analogue thereof preferably of about 0 to 50%, 5 to 45%, or 10 to 40%, more preferably of about 15 to 35%, even more preferably of about 20 to 30%, and most preferably of about 25%; a content of guanosine (guanine) or an analogue thereof preferably of about 0 to 50%, 5 to 45%, or 10 to 40%, more preferably of about 15 to 35%, even more preferably of about 20 to 30%, and most preferably of about 25%. Most preferably, N may be a nucleic acid sequence within the above definitions, wherein the sequence typically comprises a content of each adenosine (adenine), guanosine (guanine), cytidine (cytosine) and uridine (uracil) of about 25%. Examples of such sequences of N include e.g. agcu, aguc, augc, acgu, gcua, gcau, gacu, guca, cuag, caug, cagu, cgau, uagc, uacg, ucga, ucag, agcugcua, gcaucaug, caguucga, etc., The number of bordering element N in the nucleic acid molecule of formula (I) according to the invention, i.e. its repetition, is determined by integers u and/or v. Thus, N in the nucleic acid molecule of formula (I) according to the invention may occur as a (repetitive) bordering element $N_u$ and/or $N_v$, wherein u and/or v may be, independently from each other, an integer from 0 or 1 to 100, more preferably from 0 or 1 to 50, even more preferably from 0 or 1 to 40, and most preferably from 0 or 1 to 30, e.g. 0 or 1 to 5, 10, 20, 25, or 30; or from 5 to 10, 10 to 15, 15 to 20, 20 to 25 or 25 to 30. More preferably, at least one (repetitive) bordering element $N_u$ and/or $N_v$, may be present in formula (I), i.e. either u or v are not 0, more preferably, both (repetitive) bordering elements $N_u$ and/or $N_v$ are present, even more preferably in the above definitions.

Additionally, the combination of core structure elements and bordering elements to the element $N_uG_lX_mG_nN_v$ may occur as repetitive elements according to the inventive molecule of formula (I), $(N_uG_lX_mG_nN_v)_a$, as defined above, wherein the number of repetitions of the combined element according to formula (I), $(N_uG_lX_mG_nN_v)_a$, is determined by the integer a. Preferably, a is an integer from about 1 to 100, 1 to 50, 1 to 20, more preferably an integer from about 1 to 15, most preferably an integer from about 1 to 10. In this context, the repetitive elements $N_uG_lX_mG_nN_v$ may be equal or different from each other.

According to a particularly preferred embodiment, the inventive nucleic acid molecule of formula (I) $(N_uG_lX_mG_nN_v)_a$, as defined above, comprises a core structure $G_lX_mG_n$, preferably selected from at least one of the following sequences of SEQ ID NOs: 1-80:

```
                                          (SEQ ID NO: 1)
GGUUUUUUUUUUUUUUGGG;

(SEQ ID NO: 2)
GGGGGUUUUUUUUUGGGGG;

(SEQ ID NO: 3)
GGGGGUUUUUUUUUUUUUUUUUUUUUUUUUUGGGGG;

(SEQ ID NO: 4)
GUGUGUGUGUGUUUUUUUUUUUUUUGUGUGUGUGUGU;

(SEQ ID NO: 5)
GGUUGGUUGGUUUUUUUUUUUUUUGGUUGGUUGGUU;

(SEQ ID NO: 6)
GGGGGGGGUUUGGGGGGGG;

(SEQ ID NO: 7)
GGGGGGGGUUUUGGGGGGGG;

(SEQ ID NO: 8)
GGGGGGGUUUUUGGGGGGG;
```

-continued

GGGGGGGUUUUUUGGGGGG; (SEQ ID NO: 9)

GGGGGGUUUUUUGGGGGG; (SEQ ID NO: 10)

GGGGGGUUUUUUUGGGGG; (SEQ ID NO: 11)

GGGGGGUUUUUUUUGGGG; (SEQ ID NO: 12)

GGGGGUUUUUUUUUGGGG; (SEQ ID NO: 13)

GGGGGUUUUUUUUUUGGG; (SEQ ID NO: 14)

GGGGUUUUUUUUUUUGGG; (SEQ ID NO: 15)

GGGGUUUUUUUUUUUUGG; (SEQ ID NO: 16)

GGUUUUUUUUUUUUUUGG; (SEQ ID NO: 17)

GUUUUUUUUUUUUUUUG; (SEQ ID NO: 18)

GGGGGGGGGGUUUGGGGGGGG; (SEQ ID NO: 19)

GGGGGGGGGUUUUGGGGGGGG; (SEQ ID NO: 20)

GGGGGGGGUUUUUGGGGGGGG; (SEQ ID NO: 21)

GGGGGGGGUUUUUUGGGGGGG; (SEQ ID NO: 22)

GGGGGGGUUUUUUUGGGGGGG; (SEQ ID NO: 23)

GGGGGGGUUUUUUUUGGGGGG; (SEQ ID NO: 24)

GGGGGGGUUUUUUUUUGGGGG; (SEQ ID NO: 25)

GGGGGGUUUUUUUUUUGGGGG; (SEQ ID NO: 26)

GGGGGGUUUUUUUUUUUGGGG; (SEQ ID NO: 27)

GGGGGUUUUUUUUUUUUGGGG; (SEQ ID NO: 28)

GGGGGUUUUUUUUUUUUUGGG; (SEQ ID NO: 29)

GGGUUUUUUUUUUUUUUGGG; (SEQ ID NO: 30)

GGUUUUUUUUUUUUUUUUGG; (SEQ ID NO: 31)

GGGGGGGGGGGUUUGGGGGGGGG; (SEQ ID NO: 32)

GGGGGGGGGGGUUUGGGGGGGGG; (SEQ ID NO: 33)

GGGGGGGGGGUUUUGGGGGGGGG; (SEQ ID NO: 34)

GGGGGGGGGUUUUUUGGGGGGGGG; (SEQ ID NO: 35)

GGGGGGGGUUUUUUUGGGGGGG; (SEQ ID NO: 36)

GGGGGGGGUUUUUUUUGGGGGGG; (SEQ ID NO: 37)

GGGGGGGGUUUUUUUUUGGGGGG; (SEQ ID NO: 38)

GGGGGGGUUUUUUUUUUGGGGGG; (SEQ ID NO: 39)

GGGGGGGUUUUUUUUUUUGGGGG; (SEQ ID NO: 40)

GGGGGGUUUUUUUUUUUUGGGGG; (SEQ ID NO: 41)

GGGGGGUUUUUUUUUUUUUGGGG; (SEQ ID NO: 42)

GGGGUUUUUUUUUUUUUUGGGG; (SEQ ID NO: 43)

GGGUUUUUUUUUUUUUUUGGG; (SEQ ID NO: 44)

GUUUUUUUUUUUUUUUUUUUUUG; (SEQ ID NO: 45)

GGUUUUUUUUUUUUUUUUUUUGG; (SEQ ID NO: 46)

GGGUUUUUUUUUUUUUUUUUUUGGG; (SEQ ID NO: 47)

GGGGUUUUUUUUUUUUUUUUUUUGGG; (SEQ ID NO: 48)

GGGGGUUUUUUUUUUUUUUUUUUUGGGG; (SEQ ID NO: 49)

GGGGGGUUUUUUUUUUUUUUUUUUUUGGGGG; (SEQ ID NO: 50)

GGGGGGGUUUUUUUUUUUUUUUUUUUUGGGGGG; (SEQ ID NO: 51)

GGGGGGGGUUUUUUUUUUUUUUUUUUUUUGGGGGGG; (SEQ ID NO: 52)

GGGGGGGGGUUUUUUUUUUUUUUUUUUUUUGGGGGGGG; (SEQ ID NO: 53)

GGUUUGG; (SEQ ID NO: 54)

GGUUUUGG; (SEQ ID NO: 55)

GGUUUUUGG; (SEQ ID NO: 56)

GGUUUUUUGG; (SEQ ID NO: 57)

GGUUUUUUUGG; (SEQ ID NO: 58)

GGUUUUUUUUGG; (SEQ ID NO: 59)

GGUUUUUUUUUGG; (SEQ ID NO: 60)

GGUUUUUUUUUUGG; (SEQ ID NO: 61)

GGUUUUUUUUUUUGG; (SEQ ID NO: 62)

-continued

GGUUUUUUUUUUUGG; (SEQ ID NO: 63)

GGUUUUUUUUUUUUGG; (SEQ ID NO: 64)

GGUUUUUUUUUUUUUGG; (SEQ ID NO: 65)

GGUUUUUUUUUUUUUUGG; (SEQ ID NO: 66)

GGGUUUGGG; (SEQ ID NO: 67)

GGGUUUUGGG; (SEQ ID NO: 68)

GGGUUUUUGGG; (SEQ ID NO: 69)

GGGUUUUUUGGG; (SEQ ID NO: 70)

GGGUUUUUUUGGG; (SEQ ID NO: 71)

GGGUUUUUUUUGGG; (SEQ ID NO: 72)

GGGUUUUUUUUUGGG; (SEQ ID NO: 73)

GGGUUUUUUUUUUGGG; (SEQ ID NO: 74)

GGGUUUUUUUUUUUGGG; (SEQ ID NO: 75)

GGGUUUUUUUUUUUUGGG; (SEQ ID NO: 76)

GGGUUUUUUUUUUUUUGGG; (SEQ ID NO: 77)

GGGUUUUUUUUUUUUUUUGGGUUUUUUUUUUUUUUGGGUUUUUUUUUUUUUUGGG; (SEQ ID NO: 78)

GGGUUUUUUUUUUUUUUUGGGGGUUUUUUUUUUUUUUUGGG; (SEQ ID NO: 79)

GGGUUUGGGUUUGGGUUUGGGUUUGGGUUUGGGUUUGGGUUUGGGUUUGG G; (SEQ ID NO: 80)

According to another particularly preferred embodiment, the problem underlying the present invention may be solved by an alternative nucleic acid molecule according to formula (Ia)

$$(N_u C_l X_m C_n N_v)_a$$

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, C is cytidine (cytosine) or an analogue thereof,
    when l>1, at least 50% of these nucleotides (nucleosides) are cytidine (cytosine) or an analogue thereof;
m is an integer and is at least 3;
  wherein when m=3, X is uridine (uracil) or an analogue thereof,
    when m>3, at least 3 successive uridines (uracils) or analogues of uridine (uracil) occur;
n is an integer from 1 to 40,
  wherein when n=1, C is cytidine (cytosine) or an analogue thereof,
    when n>1, at least 50% of these nucleotides (nucleosides) are cytidine (cytosine) or an analogue thereof.
u, v may be independently from each other an integer from 0 to 50,
  preferably wherein when u=0, v≥1, or
    when v=0, u≥1;
wherein the nucleic acid molecule of formula (Ia) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (Ia), any of the definitions given above for elements N (i.e. $N_u$ and $N_v$) and X ($X_m$), particularly the core structure as defined above, as well as for integers a, l, m, n, u and v, similarly apply to elements of formula (Ia) correspondingly, wherein in formula (Ia) the core structure is defined by $C_l X_m C_n$. The definition of bordering elements $N_u$ and $N_v$ is identical to the definitions given above for $N_u$ and $N_v$.

More particularly, C in the nucleic acid molecule of formula (Ia) according to the invention is a nucleotide or deoxynucleotide or comprises a nucleoside, wherein the nucleotide (nucleoside) is typically cytidine (cytosine) or uridine (uracil) or an analogue thereof. In this connection, cytidine (cytosine) or uridine (uracil) nucleotide analogues are defined as non-natively occurring variants of naturally occurring cytidine (cytosine) or uridine (uracil) nucleotides. Accordingly, cytidine (cytosine) or uridine (uracil) analogues are chemically derivatized nucleotides (nucleosides) with non-natively occurring functional groups, which are preferably added to or deleted from the naturally occurring cytidine (cytosine) or uridine (uracil) nucleotide (nucleoside) or which substitute the naturally occurring functional groups of a cytidine (cytosine) or uridine (uracil) nucleotide (nucleoside). Accordingly, each component of the naturally occurring cytidine (cytosine) or uridine (uracil) nucleotide may be modified, namely the base component, the sugar (ribose) component and/or the phosphate component forming the oligonucleotide's backbone. The phosphate moieties may be substituted by e.g. phosphoramidates, phosphorothioates, peptide nucleotides, methylphosphonates etc., wherein the naturally occurring phosphodiester backbone is still preferred.

Accordingly, analogues of cytidine (cytosine) or uridine (uracil) include, without implying any limitation, any naturally occurring or non-naturally occurring cytidine (cytosine) or uridine (uracil) that has been altered chemically, for example by acetylation, methylation, hydroxylation, etc., including, for example, 2-thio-cytidine (cytosine), 3-methyl-cytidine (cytosine), 4-acetyl-cytidine (cytosine), dihydro-uridine (uracil), 4-thio-uridine (uracil), 5-carboxymethylaminomethyl-2-thio-uridine (uracil), 5-(carboxyhydroxylmethyl)-uridine (uracil), 5-fluoro-uridine (uracil), 5-bromo-uridine (uracil), 5-carboxymethylaminomethyl-uridine (uracil), 5-methyl-2-thio-uridine (uracil), N-uridine (uracil)-5-oxyacetic acid methyl ester, 5-methylaminomethyl-uridine (uracil), 5-methoxyaminomethyl-2-thio-uridine (uracil), 5'-methoxycarbonylmethyl-uridine (uracil), 5-methoxy-uridine (uracil), uridine (uracil)-5-oxyacetic acid methyl ester, uridine (uracil)-5-oxyacetic acid (v). The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. No. 5,262,530 and U.S. Pat. No. 5,700,642, the disclosures of which are incorporated by reference herein in their entirety. In the case of an nucleotide (nucleoside) analogue as described above, preference is given according to the invention especially to those analogues that increase the immunogenity of the nucleic acid molecule of formula (Ia) according to the invention and/or do not interfere with a further modification that has been introduced. At least one cytidine (cytosine) or uridine (uracil) or an analogue thereof can occur in the core structure elements $C_l$ and/or $C_n$, optionally at least 10%, 20%, 30%, 40%, 50%, 60%, 70%, 80% 90% or even 100% of the nucleotides (nucleosides) of the core structure elements $C_l$ and/or $C_n$ are a naturally occurring cytidine (cytosine), a naturally occurring uridine (uracil), and/or an analogue thereof and/or exhibit properties of an analogue thereof as defined herein. Preferably, the core structure element $C_l$ and/or $C_n$ contains at least one analogue of a naturally occurring cytidine (cytosine) and/or a naturally occurring uridine (uracil) at all. Most preferably, all nucleotides (nucleosides) of these core structure elements $C_l$ and/or $C_n$ are analogues, which may—most preferably—be identical analogues for the same type of nucleotides (nucleosides) (e.g. all cytidine (cytosine) nucleotides are provided as 2-thio-cytidine (cytosine)) or they may be distinct (e.g. at least two different cytidine (cytosine) analogues substitute the naturally occurring cytidine (cytosine) nucleotide).

The number of nucleotides (nucleosides) of core structure element C ($C_l$ and/or $C_n$) in the nucleic acid molecule of formula (Ia) according to the invention is determined by l and n. l and n, independently of one another, are each an integer from 1 to 90, 1 to 80, 1 to 70, 1 to 60, preferably 1 to 50, yet more preferably 1 to 40, and even more preferably 1 to 30, wherein the lower limit of these ranges may be 1, but alternatively also 2, 3, 4, 5, 6, 7, 8, 9, 10, 11, 12, 13, 14, 15, 16, 17, 18, 19, 20, 21, 22, 23, 24, 25, 26, 27, 28, 29, 30, or even more. Preferably, for each integer, when l and/or n=1, C is cytidine (cytosine) or an analogue thereof, and when l or n>1, at least 50%, more preferably at least 50%, 60%, 70%, 80%, 90% or even 100% of the nucleotides (nucleosides) of core structure element C ($C_l$ and/or $C_n$) are cytidine (cytosine) or an analogue thereof. For example, without implying any limitation, when l or n=4, $C_l$ and/or $C_n$ can be, for example, a CUCU, CCUU, UCUC, UUCC, CUUC, CCCU, CCUC, CUCC, UCCC or CCCC, etc.; when l or n=5, $C_l$ and/or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide (nucleoside) of core structure elements $C_l$ and/or $C_n$ directly adjacent to $X_m$, in the nucleic acid molecule of formula (Ia) according to the invention is preferably not an uridine (uracil) or an analogue thereof. More preferably nucleotides (nucleosides) of core structure elements $C_l$ and/or $C_n$ directly adjacent to $X_m$ in the nucleic acid molecule of formula (Ia) according to the invention are at least one cytidine (cytosine) or an analogue thereof, more preferably a stretch of at least 2, 3, 4, 5, 6, 7, 8, 9, 10, 11, 12, 13, 14, 15, 16, 17, 18, 19 or even 20 or more cytidines (cytosines) or an analogue thereof. Additionally, a nucleotide (nucleoside) of core structure elements $C_l$ and/or $C_n$ directly adjacent to N, e.g. $N_u$, and/or $N_v$ (or $N_{w1}$ or $N_{w2}$ as defined below) in the nucleic acid molecule of formula (Ia) according to the invention is preferably not an uridine (uracil) or an analogue thereof. More preferably, nucleotides (nucleosides) of core structure elements $C_l$ and/or $C_n$ directly adjacent to N, e.g. $N_u$, and/or $N_v$ (or $N_{w1}$ or $N_{w2}$ as defined below) in the nucleic acid molecule of formula (Ia) according to the invention are at least one cytidine (cytosine) or an analogue thereof, more preferably a stretch of at least 2, 3, 4, 5, 6, 7, 8, 9, 10, 11, 12, 13, 14, 15, 16, 17, 18, 19 or even 20 or more cytidines (cytosines) or an analogue thereof. Likewise preferably, for formula (Ia), when l or n>1, at least 60%, 70%, 80%, 90% or even 100% of the nucleotides of the core structure elements $C_l$ and/or $C_n$ are cytidine (cytosine) or an analogue thereof, as defined above. The remaining nucleotides (nucleosides) to 100% in the core structure elements $C_l$ and/or $C_n$ (when cytidine (cytosine) constitutes less than 100% of these nucleotides (nucleosides)) may then be uridine (uracil) or an analogue thereof, as defined hereinbefore.

X, particularly Xm, as a further core structure element in the inventive nucleic acid molecule according to formula (Ia), is preferably as defined above for formula (I). The number of core structure element X in the nucleic acid molecule of formula (Ia) according to the invention is determined by m. m is an integer and is typically at least 3, 4, 5, 6, 7, 8, 9, 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200, or even more, wherein when m=3, X is uridine (uracil) or an analogue thereof, and when m>3, at least 3 or more directly successive uridines (uracils) or an analogue thereof occur in the element X of formula (Ia) above. Such a sequence of at least 3 or more directly successive uridines (uracils) is referred to in connection with this application as a "monotonic uridine (uracil) sequence". A monotonic uridine (uracil) sequence typically has a length of at least 3, 4, 5, 6, 7, 8, 9 or 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200 uridines (uracils) or optionally analogues of uridine (uracil) as defined above. Such a monotonic uridine (uracil) sequence occurs at least once in the core structure element X of the nucleic acid molecule of formula (Ia) according to the invention. It is therefore possible, for example, for 1, 2, 3, 4, 5 or more monotonic uridine (uracil) sequences having at least 3 or more uridines (uracils) or analogues thereof to occur, which monotonic uridine (uracil) sequences can be interrupted in the core structure element X by at least one guanosine (guanine), adenosine (adenine), thymidine (thymine), cytidine (cytosine) or an analogue thereof, preferably 2, 3, 4, 5 or more. For example, when m=3, Xm is a UUU. When m=4, Xm can be, for example, without implying any limitation, a UUUA, UUUG, UUUC, UUUU, AUUU, GUUU or CUUU, etc. When n=10, Xm can be, for example, without implying any limitation, a UUUAAUUUUC (SEQ ID NO: 120), UUUUGUUUA (SEQ ID NO: 121), UUUGUUUGUU (SEQ ID NO: 122), UUGUUUUGUU (SEQ ID NO: 123), UUUUUUUUUU (SEQ ID NO: 124), etc. The nucleotides (nucleosides) of Xm adjacent to Cl or Cn of the nucleic acid molecule of formula (Ia) according to the invention preferably comprise uridine (uracil) or analogues thereof. When m>3, typically at least 50%, preferably at least 60%, 70%, 80%, 90% or even 100%, of the nucleotides of Xm are uridine (uracil) or an analogue thereof, as defined above. The remaining nucleotides (nucleosides) of Xm to 100% (where there is less than 100% uridine (uracil) in the sequence Xm) may then be guanosine (guanine), uridine (uracil), adenosine (adenine), thymidine (thymine), cytidine (cytosine) or an analogue thereof, as defined above.

Likewise, the inventive nucleic acid according formula (Ia) above contains a bordering element N, particularly $N_u$ and/or $N_v$, wherein the bordering element N, particularly $N_u$ and/or $N_v$, as well as integers x and y are as defined above.

The element $N_u C_l X_m C_n N_v$ may occur as a repetitive element according to the inventive nucleic acid molecule of formula (Ia) $(N_u C_l X_m C_n N_v)_a$, as defined above, wherein the number of repetitions of this element according to formula (Ia) $(N_u C_l X_m C_n N_v)_a$ is determined by the integer a. Preferably, a is an integer from about 1 to 100, 1 to 50, 1 to 20, more preferably an integer from about 1 to 15, most preferably an integer from about 1 to 10. In this context, the repetitive elements $N_u C_l X_m C_n N_v$ may be equal or different from each other. According to a particularly preferred embodiment, the inventive molecule of formula (Ia) $(N_u C_l X_m C_n N_v)_a$, as defined above, comprises a core structure $C_l X_m C_n$, preferably selected from at least one of the following sequences of SEQ ID NOs: 81-83:

```
                                            (SEQ ID NO: 81)
CCCUUUUUUUUUUUUUUUCCCUUUUUUUUUUUUUUUCCCUUUUUUUUUUU

UUUUCCC
                                            (SEQ ID NO: 82)
CCCUUUCCCUUUCCCUUUCCCUUUCCCUUUCCCUUUCCCUUUCCCUUUCC

C
                                            (SEQ ID NO: 83)
CCCUUUUUUUUUUUUUUUCCCCCCUUUUUUUUUUUUUUUCCC
```

The inventive nucleic acid molecule according to either formula (I) (or (Ia)), particularly each single repetitive element $N_u G_l X_m G_n N_v$ (or $N_u C_l X_m C_n N_v$) thereof, may be single-stranded, double-stranded or partially double-stranded, etc. as defined for formula (I) in general.

If the inventive nucleic acid molecule according to either formula (I) (or (Ia)) is a single-stranded nucleic acid molecule, the sequence is typically single-stranded over its entire length.

Likewise, if the inventive nucleic acid molecule according to either formula (I) (or (Ia)) is a double-stranded nucleic acid molecule, the sequence is typically double-stranded over its entire length.

If the inventive nucleic acid molecule according to either formula (I) (or (Ia)) is a partially double-stranded nucleic acid molecule, the nucleic acid sequence of a nucleic acid molecule of either formula (I) (or (Ia)) may be single-stranded in the region outside the core structure $G_l X_m G_n$ (or $C_l X_m C_n$), and double-stranded in the region of said core structure, the core structure $G_l X_m G_n$ (or $C_l X_m C_n$), preferably being selected from at least one of the above defined sequences of SEQ ID NOs: 1-83. Even more preferably, the core structure $G_l X_m G_n$ (or $C_l X_m C_n$) of (either) formula (I) (or (Ia)) may be double-stranded in such a region of the core structure, wherein a stretch of uridines (uracils) occurs, most preferably over the entire uridine (uracil) stretch or at least 60%, 70%, 80%, 90%, 95%, 98% or 99% thereof.

Alternatively or additionally, if the inventive nucleic acid molecule according to either formula (I) or (Ia) is a partially double-stranded nucleic acid molecule, other parts (than the core structure $G_l X_m G_n$) of the inventive nucleic acid molecule according to formula (I) or (Ia) as defined above may be double-stranded. E.g., the nucleic acid sequence of a nucleic acid molecule of either formula (I) or (Ia) may be double-stranded in the region outside the core structure $G_l X_m G$, (or $C_l X_m C_n$), e.g. in the bordering elements $N_u$ and/or $N_v$, and single-stranded in the region of said core structure, the core structure $G_l X_m G_n$ (or $C_l X_m C_n$), preferably selected from at least one of the above defined sequences of SEQ ID NOs: 1-83. E.g. at least one of the bordering elements $N_u$ and/or $N_v$ may be double-stranded, whereas the remaining elements of either formula (I) or (Ia), e.g. the core structure $G_l X_m G_n$ and/or other elements, may remain single-stranded.

Alternatively or additionally, the inventive nucleic acid molecule according to formula (I) may be selected from a mixture of a single-stranded nucleic acid molecule according to either formula (I) or (Ia) and a (partially) double-stranded nucleic acid molecule according to either formula (I) (or (Ia)), preferably in a ratio of about 1:10 to 10:1, more preferably in a ratio of 1:3 to 3:1.

According to a very particularly preferred embodiment, the inventive nucleic acid molecule according to formula (I) may be selected from e.g. any of the following sequences:

```
from SEQ ID NO: 84:
UAGCGAAGCU CUUGGACCUA GG UUUUU UUUUU UUUUU GGG

UGCGUUCCUA GAAGUACACG
or from

SEQ ID NO: 85:
UAGCGAAGCU CUUGGACCUA GG UUUUU UUUUU UUUUU GGG

UGCGUUCCUA GAAGUACACG

AUCGCUUCGA GAACCUGGAU CC AAAAA AAAAA AAAAA CCC

ACGCAAGGAU CUUCAUGUGC
or from

SEQ ID NO: 114
(R820: (N_{100})_2)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUC
or from

SEQ ID NO: 115
(R719: (N_{100})_5)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUUAACGAACGGCUCCUCCUCUUAGACUGCAGCGUAAGUGCGAAU

CUGGGGAUCAAAUUACUGACUGCCUGGAUUACCCUCGGACAUAUAACCUU
```

-continued

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAG
or from (R720: $(N_{100})_{10}$)
SEQ ID NO: 116
GGGAGAAAGCUCAAGCUUGGAGCAAUGCCCGCACAUUGAGGAAACCGAGU

UGCAUAUCUCAGAGUAUUGGCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUUAACGAACGGCUCCUCCUCUUAGACUGCAGCGUAAGUGCGGAAU

CUGGGGAUCAAAUUACUGACUGCCUGGAUUACCCUCGGACAUAUAACCUU

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAGAGC

UACGCAGGUUCGCAAUAAAAGCGUUGAUUAGUGUGCAUAGAACAGACCUC

UUAUUCGGUGAAACGCCAGAAUGCUAAAUUCCAAUAACUCUUCCCAAAAC

GCGUACGGCCGAAGACGCGCGCUUAUCUUGUGUACGUUCUCGCACAUGGA

AGAAUCAGCGGGCAUGGUGGUAGGGCAAUAGGGGAGCUGGGUAGCAGCGA

AAAAGGGCCCCUGCGCACGUAGCUUCGCUGUUCGUCUGAAACAACCCGGC

AUCCGUUGUAGCGAUCCCGUUAUCAGUGUUAUUCUUGUGCGCACUAAGAU

UCAUGGUGUAGUCGACAAUAACAGCGUCUUGGCAGAUUCUGGUCACGUGC

CCUAUGCCCGGGCUUGUGCCUCUCAGGUGCACAGCGAUACUUAAAGCCUU

CAAGGUACUCGACGUGGGUACCGAUUCGUGACACUUCCUAAGAUUAUUCC

ACUGUGUUAGCCCCGCACCGCCGACCUAAACUGGUCCAAUGUAUACGCAU

UCGCUGAGCGGAUCGAUAAUAAAAGCUUGAAUU
or from (R821: $(N_{40}U_{20}N_{40})_2$)
SEQ ID NO: 117
GGGAGAAAGCUCAAGCUUAUCCAAGUAGGCUGGUCACCUGUACAACGUAG

CCGGUAUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUAGUAAAUGCGUCUAC

UGAAUCCAGCGAUGAUGCUGGCCCAGAUC
or from (Seq. R722: $(N_{40}U_{20}N_{40})_5$)
SEQ ID NO: 118
GGGAGAAAGCUCAAGCUUAUCCAAGUAGGCUGGUCACCUGUACAACGUAG

CCGGUAUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUA
or from (R723: $(N_{40}U_{20}N_{40})_{10}$):
SEQ ID NO: 119
GGGAGAAAGCUCAAGCUUAUCCAAGUAGGCUGGUCACCUGUACAACGUAG

CCGGUAUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUAGAAC

GAACUGACCUGACGCCUGAACUUAUGAGCGUGCGUAUUUUUUUUUUUUU

UUUUUUUUUCCUCCCAACAAAUGUCGAUCAAUAGCUGGGCUGUUGGAGAC

GCGUCAGCAAAUGCCGUGGCUCCAUAGGACGUGUAGACUUCUAUUUUUUU

UUUUUUUUUUUUUUCCCGGGACCACAAAUAAUAUUCUUGCUUGGUUGGGC

GCAAGGGCCCCGUAUCAGGUCAUAAACGGGUACAUGUUGCACAGGCUCCU

UUUUUUUUUUUUUUUUUUUUCGCUGAGUUAUUCCGGUCUCAAAAGACG

GCAGACGUCAGUCGACAACACGGUCUAAAGCAGUGCUACAAUCUGCCGUG

UUCGUGUUUUUUUUUUUUUUUUUUUGUGAACCUACACGGCGUGCACUGU

AGUUCGCAAUUCAUAGGGUACCGGCUCAGAGUUAUGCCUUGGUUGAAAAC

UGCCCAGCAUACUUUUUUUUUUUUUUUUUUUCAUAUUCCCAUGCUAAGC

AAGGGAUGCCGCGAGUCAUGUUAAGCUUGAAUU

According to another very particularly preferred embodiment, the inventive nucleic acid molecule according to formula (Ia) may be selected from e.g. any of the following sequences:

(SEQ ID NO: 86)
UAGCGAAGCU CUUGGACCUA CC UUUUU UUUUU UUUUU CCC

UGCGUUCCUA GAAGUACACG
or (SEQ ID NO: 87)
UAGCGAAGCU CUUGGACCUA CC UUUUU UUUUU UUUUU CCC

UGCGUUCCUA GAAGUACACG

AUCGCUUCGA GAACCUGGAU GG AAAAA AAAAA AAAAA GGG

ACGCAAGGAU CUUCAUGUGC

According to one preferred embodiment, the inventive nucleic acid molecule according to formula (I) (or (Ia)) as defined above may be modified with a poly(X) sequence (modifying element). Such inventive nucleic acid molecules may comprise e.g. a nucleic acid molecule according to formula (II):

$$poly(X)_s(N_uG_lX_mG_nN_v)_a poly(X)_t,$$

wherein the nucleic acid molecule of formula (II) according to the invention likewise has a length of at least 50 nucleotides, preferably of at least 100 nucleotides, more preferably of at least 150 nucleotides, even more preferably of at least 200 nucleotides and most preferably of at least 250 nucleotides.

In a nucleic acid molecule according to inventive formula (II), the elements G, X and N, particularly, the core structure $G_lX_mG_n$, and the elements $N_u$ and $N_v$, as well as the integers a, l, m, n, u and v are as defined above for formula (I). In the context of the present invention, a modifying element poly(X), particularly $poly(X)_s$ and/or $poly(X)_t$, of an inventive nucleic acid molecule according to formula (II), is typically a single-stranded, a double-stranded or a partially double-stranded nucleic acid sequence, e.g a DNA or RNA sequence as defined above in general. Preferably, the modifying element poly(X), particularly $poly(X)_s$ and/or $poly(X)_t$, is a homopolymeric stretch of nucleic acids, wherein X may be any nucleotide or deoxynucleotide or comprises a nucleoside as defined above for X of an inventive nucleic acid molecule according to formula (I) or (Ia). Preferably, X may selected independently for each poly(X), particularly poly(X), and/or $poly(X)_t$, from a nucleotide or deoxynucleotide or comprises a nucleoside, wherein the nucleotide (nucleoside) is selected from guanosine (guanine), uridine (uracil), adenosine (adenine), thymidine (thymine), cytidine (cytosine), inosine or an analogue of these nucleotides, e.g. from a single-stranded stretch of cytidines (cytosines) (poly(C)), of guanosine (guanine)s (poly(G)), of adenosine (adenine)s (poly(A)), of uridines (uracils) (poly(U)), of inosines (poly(I)), etc. or from a homopolymeric double-stranded stretch of inosines and cytidines (cytoines) (poly(I:C)), of adenosine (adenine) and uridines (uracils) (poly(A:U)), etc., wherein the homopolymeric sequence, particularly poly(I:C) and/or poly(A:U), may be coupled to the sequence $(N_u\ G_lX_mG_nN_v)_a$ of the nucleic acid molecule according to formula (II) via any of its strands, e.g. either using the poly-C, the poly-I, the poly-A or the poly-U sequence. The length of modifying element poly(X), particularly $poly(X)_s$ and/or $poly(X)_t$, of the nucleic acid molecule of inventive formula (II) is determined by integers s and/or t, wherein s and/or t, independent from each other, may be an integer from about 5 to 100, preferably about 5 to 70, more preferably about 5 to 50, even more preferably about 5 to 30 and most preferably about 5 to 20.

According to a particularly preferred embodiment, a nucleic acid molecule according to formula (II) as defined above, may specifically comprise e.g. a nucleic acid molecule according to formula (IIa), $$poly(X)(N_uG_lX_mG_nN_v)_a,$$

or a nucleic acid molecule according to formula (IIIb), $$poly(X)(N_uG_lX_mG_nN_v)_a poly(X),$$

wherein any of these nucleic acid molecules of formulas (IIa) or (IIIb) according to the invention likewise has a length of at least 50 nucleotides, preferably of at least 100 nucleotides, more preferably of at least 150 nucleotides, even more preferably of at least 200 nucleotides and most preferably of at least 250 nucleotides. Similarly, all other definitions apply as set forth for formula (II) or (I) above. Likewise, said formulas (II), (IIa) and (IIIb) may be defined on basis of a formula according to formula (Ib), i.e. introducing the core structure $C_lX_mC_n$.

More preferably, poly(X) in an inventive nucleic acid molecule according to either formula (II), (IIa) and/or (IIIb) may be selected from a poly(X) as defined above, more preferably from poly(I:C) and/or from poly(A:U). These modifying elements poly(X), particularly poly(I:C) and/or poly(A:U), may be coupled to the sequence according to formula (II), (IIa) and/or (IIIb) via any of its strands, e.g. either using the poly-C, the poly-G, the poly-I, the poly-A or the poly-U sequence.

Similarly as defined above for formula (I) or (Ia), the inventive nucleic acid molecule according to either formula (II), (IIa) and/or (IIIb) may be a single-stranded, a double-stranded or a partially double-stranded nucleic acid molecule, as defined above.

If the inventive nucleic acid molecule according to either formula (II), (IIa) and/or (IIb) is a single-stranded nucleic acid molecule, the sequence is typically single-stranded over its entire length.

Likewise, if the inventive nucleic acid molecule according to either formula (II), (IIa) and/or (IIIb) is a double-stranded nucleic acid molecule, the sequence is typically double-stranded over its entire length.

If the inventive nucleic acid molecule according to either formula (II), (IIa) and/or (IIIb) is a partially double-stranded nucleic acid molecule, the nucleic acid sequence of a nucleic acid molecule of either formula (II), (IIa) and/or (IIIb) may be single-stranded in the region outside the core structure $G_lX_mG_n$, and double-stranded in the region of said core structure, the core structure $G_lX_mG_n$, preferably being selected from at least one of the above defined sequences of SEQ ID NOs: 1-80 or SEQ ID NOs: 81 to 83. Even more preferably, the core structure $G_lX_mG_n$ (or $C_lX_mC_n$) of either formula (I) (or (Ia)) may be double-stranded in such a region of the core structure, wherein a stretch of uridines (uracils) occurs, most preferably over the entire uridine (uracil) stretch or at least 60%, 70%, 80%, 90%, 95%, 98 or 99% thereof.

Alternatively or additionally, if the inventive nucleic acid molecule according to either formula (II), (IIa) and/or (IIIb) is a partially double-stranded nucleic acid molecule, other parts (than the core structure $G_lX_mG_n$) of the inventive nucleic acid molecule according to either formula (II), (IIa) and/or (IIIb) as defined above may be double-stranded. E.g., the nucleic acid sequence of a nucleic acid molecule of either formula (II), (IIa) and/or (IIIb) may be double-stranded in the region outside the core structure $G_lX_mG_n$, e.g. in the bordering elements $N_u$ and/or $N_v$, and/or in the modifying element poly(X), e.g. $poly(X)_s$ and or $poly(X)_t$ (such as e.g. a poly(I:C) or poly(A:U) sequence), and e.g. single-stranded in the region of said core structure, the core structure $G_lX_uG_n$, preferably being selected from at least one of the above defined sequences of SEQ ID NOs: 1-83. E.g. at least one of the bordering elements $N_u$ and/or $N_v$, and/or at least one of the modifying elements poly(X), e.g. $poly(X)_s$ and or poly(X), may be double-stranded, whereas the remaining elements of either formula (II), (IIa) and/or (IIIb), e.g. the core structure $G_lX_mG_n$ and/or other elements, may remain single-stranded.

Alternatively or additionally a mixture of a single-stranded nucleic acid molecule according to either formula (II), (IIa)) and/(IIIb) and a (partially) double-stranded nucleic acid molecule according to either formula (II), (IIa)) and/(IIIb), preferably in a ratio of about 1:10 to 10:1, more preferably in a ratio of 1:3 to 3:1.

According to a particularly preferred embodiment, the inventive nucleic acid molecule according to either formula (II), (IIa) and/or (IIIb) may be selected from e.g. any of the following sequences:

```
CCCCCCCCCC CCCCCCCCC GG UUUUU UUUUU UUUUU GGG                    (SEQ ID NO: 88)

CCCCCCCCCC CCCCCCCCC GG UUUUU UUUUU UUUUU GGG                    (SEQ ID NO: 89)
IIIIIIIIII IIIIIIIII

CCCCCCCCCC CCCCCCCCC GG UUUUU UUUUU UUUUU GGG                    (SEQ ID NO: 90)
           AAAAA AAAAA AAAAA (SEQ ID NO: 91)
CCCCCCCCCC CCCCCCCCC GG UUUUU UUUUU UUUUU GGG
GGGGGGGGGG GGGGGGGGGG CC AAAAA AAAAA AAAAA CCC (SEQ ID NO: 92)
CCCCCCCCCC CCCCCCCCC UAGCGAAGCU CUUGGACCUA GG
UUUUU UUUUU UUUUU GGG UGCGUUCCUA GAAGUACACG

CCCCCCCCCC CCCCCCCCC GG UUUUU UUUUU UUUUU GGG
UGCGUUCCUA GAAGUACACG
GGGGGGGGGG GGGGGGGGGG CC AAAAA AAAAA AAAAA CCC
ACGCAAGGAU CUUCAUGUGC (SEQ ID NO: 93)
UAGCGAAGCU CUUGGACCUA
AUCGCUUCGA GAACCUGGAU

CCCCCCCCCC CCCCCCCCC GG UUUUU UUUUU UUUUU GGG UGCGUUCCUA GAAGUACACG
                CC AAAAA AAAAA AAAAA CCC ACGCAAGGAU CUUCAUGUGC (SEQ ID NO: 94)
UAGCGAAGCU CUUGGACCUA
AUCGCUUCGA GAACCUGGAU
```

According to a further preferred embodiment, an inventive nucleic acid molecule according to formula (I) (or (Ia)) as defined above may be modified by inserting a stem or a stem loop, e.g. leading to a nucleic acid molecule according to formula (IIIa), (N$_u$ stem1 G$_l$X$_m$G$_n$ stem2 N$_v$)$_a$, or to a nucleic acid molecule according to formula (IIIb), (N$_u$G$_l$X$_m$G$_n$N$_v$)$_a$ stem1 N$_{w1}$ stem2 N$_{w2}$, wherein the nucleic acid molecule of either formula (IIIa) and/or (IIIb) according to the invention has a length of at least 100 nucleotides, more preferably of at least 150 nucleotides, even more preferably of at least 200 nucleotides and most preferably of at least 250 nucleotides. Likewise, said formulas (IIIa) and (IIIb) may be defined on basis of a formula according to formula (Ib), i.e. introducing the core structure C$_l$X$_m$C$_n$.

Particularly, the inventive nucleic acids of either formula (IIIa) and/or (IIIb) represent variants of formula (I) as defined above. In a nucleic acid according to any of formulas (IIIa) and/or (IIIb), the bordering elements N, i.e. N$_u$ and/or N$_v$, bordering the core structure G$_l$X$_m$G$_n$, are further augmented by at least one stem or stem loop structure, preferably consisting of single stem loop elements stem1 and stem2. In the inventive nucleic acids according to any of formulas (IIIa) and/or (IIIb) as defined above, the elements G, X and N, particularly, the core structure G$_l$X$_m$G$_n$, and the integers a, l, m, n, u and v are as defined above. More preferably integer a=1. Optionally u and/or v may be 0. Additionally, elements N$_{w1}$ and N$_{w2}$, adjacent to stem loop elements stem1 and stem2, represent further bordering elements, which are defined as described above for bordering elements N$_u$ and/or N$_v$. Particularly, bordering element N in general is as described above for N in formula (I) above, and integers w1 and w2 are independently selected from each other and are defined as above in formula (I) for integers u and/or v.

In this context, a stem or stem loop structure is an intramolecular base pairing that can occur in single-stranded DNA or, more commonly, in RNA. The structure is also known as a hairpin or hairpin loop. It occurs when two regions of the same molecule, e.g. stem loop elements stem1 and stem2, usually palindromic sequence elements in nucleic acid sequences, form base-pairs with each other, leading to (a double helix that ends in) an unpaired loop. The unpaired loop thereby typically represents a region of the nucleic acid, which shows no or nearly no homology with the sequence of either stem1 or stem2 and is thus not capable of base pairing with any of these stem loop elements. The resulting lollipop-shaped structure is a key building block of many RNA secondary structures. The formation of a stem-loop structure is thus dependent on the stability of the resulting helix and loop regions, wherein the first prerequisite is typically the presence of a sequence that can fold back on itself to form a paired double helix. The stability of paired stem loop elements is determined by the length, the number of mismatches or bulges it contains (a small number of mismatches is typically tolerable, especially in a long helix), and the base composition of the paired region. E.g., pairings between guanosine (guanine) and cytidine (cytosine) may be more preferred in such sequences, since they have three hydrogen bonds and are more stable compared to adenosine (adenine)-uridine (uracil) pairings, which have only two. In RNA, guanosine (guanine)-uridine (uracil) pairings featuring two hydrogen bonds may thus be favorable. The stability of the loop also influences the formation of the stem-loop structure. "Loops" (i.e. only the loop not containing stem loop elements stem1 and stem2) that are less than three bases long are sterically less preferable. However, stems, i.e. formations which show no (defined) loop but just an unpaired region between stem1 and stem2 may also be included. In the context of the present invention, optimal loop length tends to be about 4-100 bases long, more preferably 4 to 50 or even 4 to 30 or even 4 to 20 bases.

Hence, in the context of a nucleic acid molecule according to any of formulas (IIIa) and/or (IIIb), stem loop elements stem1 and stem2 typically represent parts of one stem or stem loop structure, wherein the stem or stem loop structure may be formed by stem loop elements stem1 and stem2, and a loop may be formed by a sequence, which is located between these stem loop elements. The stem or stem loop may have the form of a helix in the base-paired region. Each stem loop element stem1 and stem2, is preferably a nucleic acid as defined above, more preferably an RNA, and most preferably a single-stranded RNA, wherein any of nucleotides (nucleosides) or analogs as defined above for core structure element X may be used as a nucleotides (nucleosides) for either stem1 and/or stem2. Additionally, stem loop element stem1 represents a palindromic sequence of stem loop element stem2. Both sequences are therefore preferably capable of base pairing with each other and thus together form basis for a stem or stem loop.

Therefore, stem loop elements stem1 or stem2 may be selected pairwise from any nucleic acid sequence, provided that stem loop elements stem1 or stem2 are palindromic to each other, i.e. that one sequence is equal to the other (complementary) sequence read backwards or shows a homology to this sequence of at least 90%, more preferably of at least 95%, and most preferably of at least 99% to the other sequence, when read backwards. Such palindromic sequences stem1 and stem2 may be formed each by a nucleic acid sequence having a length of about 5 to 50, more preferably about 5 to 40 and most preferably about 5 to 30 nucleic acids, selected from adenosine (adenine), guanosine (guanine), cytidine (cytosine), uridine (uracil), thymidine (thymine), or an analogue thereof as defined herein.

Exemplary sequences for stem loop elements stem1 and stem2 may include e.g.:

```
a) for stem1:
   UAGCGAAGCUCUUGGACCUA      (SEQ ID NO: 95)

for stem2:
   UAGGUCCAAGAGCUUCGCUA      (SEQ ID NO: 96)

b) for stem1:
   UAGGUCCAAGAGCUUCGCUA      (SEQ ID NO: 96)

for stem2:
   UAGCGAAGCUCUUGGACCUA      (SEQ ID NO: 95)

c) for stem1:
   GCCGCGGGCCG               (SEQ ID NO: 97)

for stem2:
   CGGCCCGCGGC               (SEQ ID NO: 98)

d) for stem1:
   CGGCCCGCGGC               (SEQ ID NO: 98)

for stem2:
   GCCGCGGGCCG               (SEQ ID NO: 97)

e) for stem1:
   GACACGGUGC                (SEQ ID NO: 99)

for stem2:
   GCACCGUGCA                (SEQ ID NO: 100)

f) for stem1:
   GCACCGUGCA                (SEQ ID NO: 100)

for stem2:
   GACACGGUGC                (SEQ ID NO: 99)

g) for stem1:
   ACCUAGGU                  (SEQ ID NO: 101)

for stem2:
   ACCUAGGU                  (SEQ ID NO: 101)

h) for stem1:
   UGGAUCCA                  (SEQ ID NO: 102)

for stem2:
   UGGAUCCA                  (SEQ ID NO: 102)

i) for stem1:
   CCUGC                     (SEQ ID NO: 103)

for stem2:
   GCAGG                     (SEQ ID NO: 104)

j) for stem1:
   GCAGG                     (SEQ ID NO: 105)

for stem2:
   CCUGC                     (SEQ ID NO: 106)
``` etc.

According to one first alternative, the core structure $G_l X_m G_n$ may be located within the stem loop structure, i.e. the core structure $G_l X_m G_n$ may be located between stem loop elements stem1 and stem2, thereby preferably forming a loop. Such a nucleic acid molecule is resembled by formula (IIIa), having the composition $(N_u \text{ stem1 } G_l X_n G_n \text{ stem2 } N_v)_a$, as defined above. When u and/or v=0, and a=1 formula (IIIa) may lead to a specific nucleic acid molecule "stem1 $G_l X_m G_n$ stem2", which is also incorporated by the present invention.

According to another alternative, the core structure $G_l X_m G_n$ may be located outside the stem loop structure, wherein likewise stem loop elements stem1 and stem2 may be separated from each other by a sequence, preferably a bordering element N, e.g. $N_{w1}$ or $N_{w2}$, which then may form a loop structure upon base pairing of stem loop elements stem1 and stem2. Additionally, stem loop elements 1 and/or 1, adjacent to the core structure $G_l X_m G_n$ may be separated from the core structure $G_l X_m G_n$ by a further bordering element, e.g. $N_{w1}$ or $N_{w2}$. According to the present invention, such a nucleic acid is resembled by formula (IIIb), having the composition $(N_u G_l X_n G_n N_v)_a$ stem1 $N_{w1}$ stem2 $N_{w2}$, as defined above.

The inventive nucleic acid molecule according to either formula (IIIa) and/or (IIIb) may be single-stranded, or partially double-stranded.

If the inventive nucleic acid molecule according to either formula (IIIa) and/or (IIIb) is a single-stranded nucleic acid molecule, the sequence is typically single-stranded over its entire length.

If the inventive nucleic acid molecule according to either formula (IIIa) and/or (IIIb) is a partially double-stranded nucleic acid molecule, the nucleic acid molecule of either formula (IIIa) and/or (IIIb) preferably may be single-stranded in the region of the stem loop elements stem1 and stem2 and in the regions of the loop formed by either the core structure $G_lX_mG_n$ or by any other element, e.g. $N_{w1}$ or $N_{w2}$. Elements positioned outside the stem loop elements stem1 and stem2 and in the regions of the loop formed by either the core structure $G_lX_mG_n$ or by any other element, e.g. $N_{w1}$ or $N_{w2}$, may then be, independent from each other, single or double-stranded.

Alternatively or additionally a mixture of a single-standed or partially double-stranded nucleic acid molecule according to either formula (IIIa) or (IIIb) and a (partially) double-stranded nucleic acid molecule according to either formula (IIIa) or (IIIb), preferably in a ratio of about 1:10 to 10:1, more preferably in a ratio of 1:3 to 3:1.

According to a very particularly preferred embodiment, the inventive nucleic acid molecule according to either formula (IIIa) and/or (IIIb), respectively, may be selected from e.g. any of the following sequences:

```
                                             (SEQ ID NO: 107)
UAGCGAAGCU CUUGGACCUA GG UUUUU UUUUU UUUUU GGG

UAGGUCCAAG AGCUUCGCUA
                                             (SEQ ID NO: 108)
UAGCGAAGCU CUUGGACCUA GG UUUUU UUUUU UUUUU GGG

UGCGUUCCUA GAAGUACACG GCCGCGGGCCG UGCGUUCCUA

GAAGUACACG CGGCCCGCGGC UGCGUUCCUA GAAGUACACG
```

(stem1 and stem2 are underlined, the core structure $G_lX_mG_n$ is written in bold)

Nucleic acid molecules of either formula (I), (Ia), (II), (IIa), (IIIb), (IIIa) and/or (IIIb) according to the invention as defined above, may be prepared using any method known in the art, including synthetic methods such as e.g. solid phase synthesis, as well as in vitro methods such as in vitro transcription reactions. Preferably, an in vitro transcription is used for preparation of the inventive nucleic acid molecules. As surprisingly found by the inventors of the present invention, nucleic acid molecules of either formula (I), (Ia), (II), (IIa), (IIb), (IIIa) and/or (IIIb) according to the invention as defined above show an even better stimulation of the innate immune system, when prepared by an in vitro transcription due to its 5'-phosphate, when compared to nucleic acid molecules of either formula (I), (Ia), (II), (IIa), (IIIb), (IIIa) and/or (IIIb) according to the invention prepared by synthetic methods. Such a stimulation of the innate immune system is, without being bound thereto, contributed to the activation of the receptor RIG-1. Accordingly, nucleic acid molecules of either formula (I), (Ia), (II), (IIa), (IIIb), (IIIa) and/or (IIIb) according to the invention as defined above are particularly preferred, when prepared by an in vitro transcription reaction.

The nucleic acid molecule of either formula (I), (Ia), (II), (IIa), (IIIb), (IIIa) and/or (IIIb) according to the invention as defined above is typically provided as a "stabilized oligonucleotide", that is to say as an oligoribonucleotide or oligodeoxyribonucleotide that is resistant to in vivo degradation (e.g. by an exo- or endo-nuclease). Such stabilization can be effected, for example, by a modified phosphate backbone of the nucleic acid molecule of either formula (I), (Ia), (II), (IIa), (IIIb), (IIIa) and/or (IIIb) according to the invention as defined above. Nucleotides that are preferably used in this connection contain a phosphorothioate-modified phosphate backbone, preferably at least one of the phosphate oxygens contained in the phosphate backbone being replaced by a sulfur atom. Other stabilized oligonucleotides include, for example: non-ionic analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. However, the naturally occurring phosphodiester backbone is still preferred.

The nucleic acid molecule of either formula (I), (Ia), (II), (IIa), (IIIb), (IIIa) and/or (IIIb) according to the invention as defined above can likewise be stabilized. As mentioned above, any nucleic acid, for example DNA or RNA, can in principle be used for the nucleic acid molecule of either formula (I), (Ia), (II), (IIa), (IIIb), (IIIa) and/or (IIIb) according to the invention as defined above. From the point of view of safety, however, the use of RNA for such a nucleic acid molecule is preferred. In particular, RNA does not involve the risk of being stably integrated into the genome of the transfected cell. In addition, RNA is degraded substantially more easily in vivo. Likewise, no anti-RNA antibodies have hitherto been detected, presumably owing to the relatively short half-life of RNA in vivo as compared with DNA. In comparison with DNA, RNA is considerably less stable in solution, which is, inter alia, due substantially to RNA-degrading enzymes, so-called RNases (ribonucleases). Even the smallest ribonuclease contaminations are sufficient to degrade RNA completely in solution. Such RNase contaminations can generally be removed only by special treatment, in particular with diethyl pyrocarbonate (DEPC). Accordingly, the natural degradation of mRNA in the cytoplasm of cells is very finely regulated. A number of mechanisms are known in this connection in the prior art. Thus, the terminal structure is typically of critical importance for an mRNA in vivo. At the 5' end of naturally occurring mRNAs there is usually a so-called "cap structure" (a modified guanosine (guanine) nucleotide) and at the 3' end a sequence of up to 200 adenosine (adenine) nucleotides (the so-called poly-A tail).

The nucleic acid molecule of either formula (I), (Ia), (II), (IIa), (IIIb), (IIIa) and/or (IIIb) according to the invention as defined above, particularly if provided as an (m)RNA, can therefore be stabilized against degradation by RNases by the addition of a so-called "5' Cap" structure. Particular preference is given in this connection to a m7G(5')ppp (5'(A,G(5') ppp(5')A or G(5')ppp(5')G as the "5' Cap" structure. However, such a modification is introduced only if a modification, for example a lipid modification, has not already been introduced at the 5' end of the nucleic acid molecule of either formula (I), (Ia), (II), (IIa), (IIIb), (IIIa) and/or (IIIb) according to the invention as defined above or if the modification does not interfere with the immunogenic properties of the (unmodified or chemically modified) nucleic acid molecule of either formula (I), (Ia), (II), (IIa), (IIIb), (IIIa) and/or (IIIb) according to the invention as defined above.

Alternatively, the 3' end of the nucleic acid molecule of either formula (I), (Ia), (II), (IIa), (IIIb), (IIIa) and/or (IIIb) according to the invention as defined above, particularly if provided as an RNA, can be modified by a sequence of at least 50 adenosine ribonucleotides, preferably at least 70 adenosine ribonucleotides, more preferably at least 100 adenosine ribonucleotides, particularly preferably at least 200 adenosine (adenine) ribonucleotides (so-called "poly-A tail"). Particularly, the nucleic acid molecule of either formula (I), (Ia), (II), (IIa), (IIIb), (IIIa) and/or (IIIb) according to the invention as defined above may contain, especially if the RNA is in the form of an (m)RNA, a poly-A tail on the 3' terminus of typically about 10 to 200 adenosine nucleotides, preferably about 10 to 100 adenosine nucleotides, more preferably about 20 to 100 adenosine nucleotides or even more preferably about 40 to 80 adenosine nucleotides.

Furthermore, the 3' end of the nucleic acid molecule of either formula (I), (Ia), (II), (IIa), (IIIb), (IIIa) and/or (IIIb) according to the invention as defined above, particularly if provided as an RNA, can be modified by a sequence of at least 50 cytidine ribonucleotides, preferably at least 70 cytidine ribonucleotides, more preferably at least 100 cytidine ribonucleotides, particularly preferably at least 200 cytidine ribonucleotides (so-called "poly-C tail"). Particularly, the nucleic acid molecule of either formula (I), (Ia), (II), (IIa), (IIb), (IIIa) and/or (IIIb) according to the invention as defined above may contain, especially if the RNA is in the form of an (m)RNA, a poly-C tail on the 3' terminus of typically about 10 to 200 cytidine nucleotides, preferably about 10 to 100 cytidine nucleotides, more preferably about 20 to 70 cytidine nucleotides or even more preferably about 20 to 60 or even 10 to 40 cytidine nucleotides.

Analogously, in this case too, such a ("poly-A tail" and/or "poly-C tail"-) modification can be introduced only if no modification, for example a lipid modification, has already been introduced at the 3' end of the nucleic acid molecule of either formula (I), (Ia), (II), (IIa), (IIIb), (IIIa) and/or (IIIb) according to the invention as defined above or if the modification does not interfere with the immunogenic properties of the (unmodified or chemically modified) nucleic acid molecule of either formula (I), (Ia), (II), (IIa), (IIIb), (IIIa) and/or (IIIb) according to the invention as defined above.

The above-mentioned modifications, that is to say the insertion of a "5' Cap" structure or the insertion of a "poly-A tail" and/or a "poly-C tail" at the 3' end, prevent premature degradation of the nucleic acid molecule of either formula (I), (Ia), (II), (IIa), (IIIb), (IIIa) and/or (IIIb) according to the invention as defined above in vivo and accordingly stabilize the nucleic acid molecule of either formula (I), (Ia), (II), (IIa), (IIIb), (IIIa) and/or (IIIb) according to the invention as defined above in vivo.

According to a particular embodiment, the nucleic acid molecule of either formula (I), (Ia), (II), (IIa), (IIIb), (IIIa) and/or (IIIb) according to the invention as defined above can contain a lipid modification. Such a lipid-modified nucleic acid molecule according to the invention typically comprises a nucleic acid molecule of either formula (I), (Ia), (II), (IIa), (IIIb), (IIIa) and/or (IIIb) according to the invention as defined above, at least one linker covalently linked with that nucleic acid molecule according to the invention, and at least one lipid covalently linked with the respective linker. Alternatively, the lipid-modified nucleic acid molecule according to the invention comprises a (at least one) nucleic acid molecule of either formula (I), (Ia), (II), (IIa), (IIIb), (IIIa) and/or (IIIb) according to the invention as defined above and at least one (bifunctional) lipid covalently linked (without a linker) with that nucleic acid molecule according to the invention. According to a third alternative, the lipid-modified nucleic acid molecule according to the invention comprises a nucleic acid molecule of either formula (I), (Ia), (II), (IIa), (IIIb), (IIIa) and/or (IIIb) according to the invention as defined above, at least one linker covalently linked with that nucleic acid molecule according to the invention, and at least one lipid covalently linked with the respective linker, and also at least one (bifunctional) lipid covalently linked (without a linker) with that nucleic acid molecule according to the invention.

The lipid contained in the lipid-modified nucleic acid molecule according to the invention is typically a lipid or a lipophilic residue that preferably is itself biologically active. Such lipids preferably include natural substances or compounds such as, for example, vitamins, e.g. α-tocopherol (vitamin E), including RRR-α-tocopherol (formerly D-α-tocopherol), L-α-tocopherol, the racemate D,L-α-tocopherol, vitamin E succinate (VES), or vitamin A and its derivatives, e.g. retinoic acid, retinol, vitamin D and its derivatives, e.g. vitamin D and also the ergosterol precursors thereof, vitamin E and its derivatives, vitamin K and its derivatives, e.g. vitamin K and related quinone or phytol compounds, or steroids, such as bile acids, for example cholic acid, deoxycholic acid, dehydrocholic acid, cortisone, digoxygenin, testosterone, cholesterol or thiocholesterol. Further lipids or lipophilic residues within the scope of the present invention include, without implying any limitation, polyalkylene glycols (Oberhauser et al., Nucl. Acids Res., 1992, 20, 533), aliphatic groups such as, for example, $C_1$-$C_{20}$-alkanes, $C_1$-$C_{20}$-alkenes or $C_1$-$C_{20}$-alkanol compounds, etc., such as, for example, dodecanediol, hexadecanol or undecyl residues (Saison-Behmoaras et al., EMBO), 1991, 10, 111; Kabanov et al., FEBS Lett., 1990, 259, 327; Svinarchuk et al., Biochimie, 1993, 75, 49), phospholipids such as, for example, phosphatidylglycerol, diacylphosphatidylglycerol, phosphatidylcholine, dipalmitoylphosphatidylcholine, distearoylphosphatidylcholine, phosphatidylserine, phosphatidylethanolamine, di-hexadecyl-rac-glycerol, sphingolipids, cerebrosides, gangliosides, or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), polyamines or polyalkylene glycols, such as, for example, polyethylene glycol (PEG) (Manoharan et al., Nucleosides & Nucleotides, 1995, 14, 969), hexaethylene glycol (HEG), palmitin or palmityl residues (Mishra et al., Biochim. Biophys. Acta, 1995, 1264, 229), octadecylamines or hexylamino-carbonyl-oxycholesterol residues (Crooke et al., J. Pharmacol. Exp. Ther., 1996, 277, 923), and also waxes, terpenes, alicyclic hydrocarbons, saturated and mono- or poly-unsaturated fatty acid residues, etc.

Linking between the lipid and the nucleic acid molecule of either formula (I), (Ia), (II), (IIa), (IIIb), (IIIa) and/or (IIIb) according to the invention as defined above can in principle take place at any nucleotide, at the base or the sugar component of any nucleotide of the inventive nucleic acid, at the 3' and/or 5' end, and/or at the phosphate backbone of the nucleic acid molecule of either formula (I), (Ia), (II), (IIa), (IIIb), (IIIa) and/or (IIIb) according to the invention as defined above. Particular preference is given according to the invention to a terminal lipid modification of the nucleic acid molecule according to the invention at the 3' and/or 5' end thereof. A terminal modification has a number of advantages over modifications within the sequence. On the one hand, modifications within the sequence can influence the hybridisation behaviour, which may have an adverse effect in the case of sterically demanding residues. On the other hand, in the case of the synthetic preparation of a lipid-modified nucleic acid molecule according to the invention that is modified only terminally, the synthesis of the nucleic acid molecule of either formula (I), (Ia), (II), (IIa), (IIIb), (IIIa) and/or (IIIb) according to the invention as defined above can be carried out with commercially available monomers that are obtainable in large quantities, and synthesis protocols known in the prior art can be used.

According to a first preferred embodiment, linking between the nucleic acid molecule according to the invention and at least one lipid that is used is effected via a "linker" (covalently linked with the nucleic acid molecule of either formula (I), (Ia), (II), (IIa), (IIIb), (IIIa) and/or (IIIb) according to the invention as defined above). Linkers within the scope of the present invention typically have at least two and optionally 3, 4, 5, 6, 7, 8, 9, 10, 10-20, 20-30 or more reactive groups, selected from, for example, a hydroxy group, an amino group, an alkoxy group, etc. One reactive group preferably serves to bind the above-described nucleic acid molecule of either formula (I), (Ia), (II), (IIa), (IIIb), (IIIa) and/or (IIIb) according to the invention as defined above, for example an RNA oligonucleotide. This reactive group can be present in protected form, for example as a DMT group (dimethoxytrityl chloride), as a Fmoc group, as a MMT (monomethoxytrityl) group, as a TFA (trifluoroacetic acid) group, etc. Furthermore, sulfur groups can be protected by disulfides, for example alkylthiols such as, for example, 3-thiopropanol, or by activated components such as 2-thiopyridine. One or more further reactive groups serve according to the invention for the covalent binding of one or more lipids. According to the first embodiment, therefore, a nucleic acid molecule of either formula (I), (Ia), (II), (IIa), (IIIb), (IIIa) and/or (IIIb) according to the invention as defined above can bind via the covalently bound linker preferably at least one lipid, for example 1, 2, 3, 4, 5, 5-10, 10-20, 20-30 or more lipid(s), particularly preferably at least 3-8 or more lipid(s) per nucleic acid molecule of either formula (I), (Ia), (II), (IIa), (IIIb), (IIIa) and/or (IIIb) according to the invention as defined above. The bound lipids can thereby be bound separately from one another at different positions of the nucleic acid molecule of either formula (I), (Ia), (II), (IIa), (IIIb), (IIIa) and/or (IIIb) according to the invention as defined above, or they can be present in the form of a complex at one or more positions of the nucleic acid molecule of either formula (I), (Ia), (II), (IIa), (IIIb), (IIIa) and/or (IIIb) according to the invention as defined above. An additional reactive group of the linker can be used for direct or indirect (cleavable) binding to a carrier material, for example a solid phase. Preferred linkers according to the present invention are, for example, glycol, glycerol and glycerol derivatives, 2-aminobutyl-1,3-propanediol and 2-aminobutyl-1,3-propanediol derivatives/skeleton, pyrrolidine linkers or pyrrolidine-containing organic molecules (in particular for a modification at the 3' end), etc. Glycerol or glycerol derivatives ($C_3$ anchor) or a 2-aminobutyl-1,3-propanediol derivative/skeleton ($C_7$ anchor) are particularly preferably used according to the invention as linkers. A glycerol derivative ($C_3$ anchor) as linker is particularly preferred when the lipid modification can be introduced via an ether bond. If the lipid modification is to be introduced via an amide or a urethane bond, for example, a 2-aminobutyl-1,3-propanediol skeleton ($C_7$ anchor), for example, is preferred. In this connection, the nature of the bond formed between the linker and the nucleic acid molecule of either formula (I), (Ia), (II), (IIa), (IIIb), (IIIa) and/or (IIIb) according to the invention as defined above is preferably such that it is compatible with the conditions and chemicals of amidite chemistry, that is to say it is preferably neither acid-nor base-labile. Preference is given in particular to bonds that are readily obtainable synthetically and are not hydrolysed by the ammoniacal cleavage procedure of a nucleic acid synthesis process. Suitable bonds are in principle all correspondingly suitable bonds, preferably ester bonds, amide bonds, urethane and ether bonds. In addition to the good accessibility of the starting materials (few synthesis steps), particular preference is given to the ether bond owing to its relatively high biological stability towards enzymatic hydrolysis. According to a second preferred embodiment, the (at least one) nucleic acid molecule of either formula (I), (Ia), (II), (IIa), (IIIb), (IIIa) and/or (IIIb) according to the invention as defined above is linked directly with at least one (bifunctional) lipid as described above, that is to say without the use of a linker as described above. In this case, the (bifunctional) lipid used according to the invention preferably contains at least two reactive groups or optionally 3, 4, 5, 6, 7, 8, 9, 10 or more reactive groups, a first reactive group serving to bind the lipid directly or indirectly to a carrier material described herein and at least one further reactive group serving to bind a nucleic acid molecule of either formula (I), (Ia), (II), (IIa), (IIIb), (IIIa) and/or (IIIb) according to the invention as defined above. According to the second embodiment, a nucleic acid molecule of either formula (I), (Ia), (II), (IIa), (IIIb), (IIIa) and/or (IIIb) according to the invention as defined above can therefore preferably bind at least one lipid (directly without a linker), for example 1, 2, 3, 4, 5, 5-10, 10-20, 20-30 or more lipid(s), particularly preferably at least 3-8 or more lipid(s) per nucleic acid molecule of either formula (I), (Ia), (II), (IIa), (IIIb), (IIIa) and/or (IIIb) according to the invention as defined above. The bound lipids can be bound separately from one another at different positions of the nucleic acid molecule of either formula (I), (Ia), (II), (IIa), (IIIb), (IIIa) and/or (IIIb) according to the invention as defined above, or they can be present in the form of a complex at one or more positions of the nucleic acid molecule of either formula (I), (Ia), (II), (IIa), (IIIb), (IIIa) and/or (IIIb) according to the invention as defined above. Alternatively, at least one nucleic acid molecule of either formula (I), (Ia), (II), (IIa), (IIIb), (IIIa) and/or (IIIb) according to the invention as defined above, for example optionally 3, 4, 5, 6, 7, 8, 9, 10, 10-20, 20-30 or more nucleic acids of either formula (I), (Ia), (II), (IIa), (IIIb), (IIIa) and/or (IIIb) according to the invention as defined above, can be bound according to the second embodiment to a lipid as described above via its reactive groups. Lipids that can be used for this second embodiment particularly preferably include those (bifunctional) lipids that permit coupling (preferably at their termini or optionally intramolecularly), such as, for example, polyethylene glycol (PEG) and derivatives thereof, hexaethylene glycol (HEG) and derivatives thereof, alkanediols, aminoalkane, thioalkanols, etc. The nature of the bond between a (bifunctional) lipid and a nucleic acid molecule of either formula (I), (Ia), (II), (IIa), (IIIb), (IIIa) and/or (IIIb) according to the invention as defined above, as described above, is preferably as described for the first preferred embodiment.

According to a third embodiment, linking between the nucleic acid molecule of either formula (I), (Ia), (II), (IIa), (IIIb), (IIIa) and/or (IIIb) according to the invention as defined above and at least one lipid as described above can take place via both of the above-mentioned embodiments simultaneously. For example, the nucleic acid molecule of either formula (I), (Ia), (II), (IIa), (IIIb), (IIIa) and/or (IIIb) according to the invention as defined above can be linked at one position of the nucleic acid with at least one lipid via a linker (analogously to the first embodiment) and at a different position of the nucleic acid molecule of either formula (I), (Ia), (II), (IIa), (IIIb), (IIIa) and/or (IIIb) according to the invention as defined above directly with at least one lipid without the use of a linker (analogously to the second embodiment). For example, at the 3' end of a nucleic acid molecule of either formula (I), (Ia), (II), (IIa), (IIIb), (IIIa) and/or (IIIb) according to the invention as defined above, at least one lipid as described above can be covalently linked with the nucleic acid via a linker, and at the 5' end of the nucleic acid molecule according to the invention, a lipid as described above can be covalently linked with the nucleic acid without a linker. Alternatively, at the 5' end of a nucleic acid molecule of either formula (I), (Ia), (II), (IIa), (IIIb), (IIIa) and/or (IIIb) according to the invention as defined above, at least one lipid as described above can be covalently linked with the nucleic acid molecule via a linker, and at the 3' end of the nucleic acid molecule of either formula (I), (Ia), (II), (IIa), (IIIb), (IIIa) and/or (IIIb) according to the invention as defined above, a lipid as described above can be covalently linked with the nucleic acid molecule without a linker. Likewise, covalent linking can take place not only at the termini of the nucleic acid molecule of either formula (I), (Ia), (II), (IIa), (IIIb), (IIIa) and/or (IIIb) according to the invention as defined above but also intramolecularly, as described above, for example at the 3' end and intramolecularly, at the 5' end and intramolecularly, at the 3' and 5' end and intramolecularly, only intramolecularly, etc.

The lipid-modified nucleic acid molecule of either formula (I), (Ia), (II), (IIa), (IIIb), (IIIa) and/or (IIIb) according to the invention as defined above can preferably be obtained by various processes. The lipid modification can in principle— as defined above—be introduced at any position of the nucleic acid molecule of either formula (I), (Ia), (II), (IIa), (IIIb), (IIIa) and/or (IIIb) according to the invention as defined above, for example at the 3' and/or 5' ends or at the phosphate backbone of the nucleic acid molecule of either formula (I), (Ia), (II), (IIa), (IIIb), (IIIa) and/or (IIIb) according to the invention as defined above and/or at any base or at the sugar of any nucleotide of the nucleic acid molecule of either formula (I), (Ia), (II), (IIa), (IIb), (IIIa) and/or (IIIb) according to the invention as defined above. According to the invention, preference is given to terminal lipid modifications at the 3' and/or 5' ends of the nucleic acids of either formula (I), (Ia), (II), (IIa), (IIIb), (IIIa) and/or (IIIb) according to the invention as defined above. By means of such a terminal chemical modification it is possible according to the invention to obtain a large number of differently derivatised nucleic acids. The process for preparing such lipid-modified nucleic acids of either formula (I), (Ia), (II), (IIa), (IIIb), (IIIa) and/or (IIIb) according to the invention as defined above is preferably chosen in dependence on the position of the lipid modification.

If, for example, the lipid modification takes place at the 3' end of the nucleic acid molecule of either formula (I), (Ia), (II), (IIa), (IIIb), (IIIa) and/or (IIIb) according to the invention as defined above, then the lipid modification is typically carried out either before or after the preparation of the nucleic acid molecule of either formula (I), (Ia), (II), (IIa), (IIIb), (IIIa) and/or (IIIb) according to the invention as defined above. The preparation of the nucleic acid molecule of either formula (I), (Ia), (II), (IIa), (IIIb), (IIIa) and/or (IIIb) according to the invention as defined above can be carried out by direct synthesis of the nucleic acid or optionally by addition of a ready synthesized nucleic acid or a nucleic acid from samples isolated from other sources.

According to a first alternative, the nucleic acid molecule of either formula (I), (Ia), (II), (IIa), (IIIb), (IIIa) and/or (IIIb) according to the invention as defined above is synthesized directly before introduction of the lipid, typically by means of processes known in the prior art for the synthesis of nucleic acids. To this end, a starting nucleotide (nucleoside) is preferably bound to a solid phase, for example via a coupling molecule, e.g. a succinyl residue, and the nucleic acid molecule of either formula (I), (Ia), (II), (IIa), (IIIb), (IIIa) and/or (IIIb) according to the invention as defined above is synthesized, for example by the process of amidite chemistry. A linker as described hereinbefore is then covalently bonded, preferably v/a a first reactive group of the linker, to the 3' end of the nucleic acid molecule of either formula (I), (Ia), (II), (IIa), (IIIb), (IIIa) and/or (IIIb) according to the invention as defined above. A lipid as described hereinbefore can then be covalently linked with the linker Via a second reactive group of the linker. Alternatively, the linker can be covalently linked with the lipid before it is bound to the 3' end of the nucleic acid molecule of either formula (I), (Ia), (II), (IIa), (IIIb), (IIIa) and/or (IIIb) according to the invention as defined above. In this case, only the binding of a first reactive group of the linker with the 3' end of the nucleic acid molecule of either formula (I), (Ia), (II), (IIa), (IIIb), (IIIa) and/or (IIIb) according to the invention as defined above is necessary. After synthesis of the nucleic acid molecule of either formula (I), (Ia), (II), (IIa), (IIIb), (IIIa) and/or (IIIb) according to the invention as defined above, or after binding of the lipid, the nucleic acid molecule of either formula (I), (Ia), (II), (IIa), (IIIb), (IIIa) and/or (IIIb) according to the invention as defined above can be separated from the solid phase and deprotected. If the synthesis has been carried out in solution, a washing and purification step for removing unreacted reactants as well as solvents and undesirable secondary products can be carried out after the synthesis of the lipid-modified nucleic acid molecule according to the invention (and optionally before separation from the carrier material).

According to a further alternative, a 3'-lipid-modified nucleic acid molecule of either formula (I), (Ia), (II), (IIa), (IIIb), (IIIa) and/or (IIIb) according to the invention as defined above, as defined above, is synthesized after introduction of the lipid on a reactive group of the linker or is bound to the reactive group of the linker as a ready synthesized nucleic acid molecule of either formula (I), (Ia), (II), (IIa), (IIIb), (IIIa) and/or (IIIb) according to the invention as defined above. To this end, for example, a first reactive group of a linker as described above can be reacted with a lipid as described hereinbefore. Then, preferably in a second step, a second reactive group of the linker is provided with an acid-stable protecting group, e.g. DMT, Fmoc, etc., in order to permit subsequent binding of the nucleic acid molecule of either formula (I), (Ia), (II), (IIa), (IIIb), (IIIa) and/or (IIIb) according to the invention as defined above to that reactive group. The linker can then be bound directly or indirectly to a solid phase via a third reactive group of the linker. Indirect binding is possible, for example, via a (coupling) molecule, which can be bound both covalently to the linker and to the solid phase. Such a (coupling) molecule is, for example, a succinyl residue, etc., as described hereinbelow. Removal of the protecting group at the third reactive group of the linker and the binding or synthesis of the nucleic acid molecule of either formula (I), (Ia), (II), (IIa), (IIIb), (IIIa) and/or (IIIb) according to the invention as defined above at the reactive group that is now accessible then usually take place. Finally, the lipid-modified nucleic acid molecule according to the invention is typically cleaved from the carrier material (and the protective groups on the nucleic acid are optionally removed). However, a further lipid can optionally also be coupled to the 3' end of the coupled nucleic acid molecule according to the invention of either formula (I), (Ia), (II), (IIa), (IIIb), (IIIa) and/or (IIIb), preferably according to one of the steps described hereinbefore.

According to a variant of this above-mentioned alternative, a linker as described above can be bound directly or indirectly to a solid phase via a first reactive group. An acid-stable protecting group is then first bound to a second reactive group of the linker. After binding of the protecting group to the second reactive group, a lipid as described above can first be bound to a third reactive group of the linker. Then there are likewise preferably carried out the removal of the protecting group at the third reactive group of the linker, the binding or synthesis of a nucleic acid molecule of either formula (I), (Ia), (II), (IIa), (IIIb), (IIIa) and/or (IIIb) according to the invention as defined above at the reactive group that is now accessible, and the cleavage of the lipid-modified nucleic acid molecule according to the invention from the carrier material (and optionally the removal of the protecting groups at the nucleic acid).

According to a particularly preferred embodiment of the 3'-lipid modification of a nucleic acid molecule of either formula (I), (Ia), (II), (IIa), (IIIb), (IIIa) and/or (IIIb) according to the invention as defined above, such a lipid-modified nucleic acid molecule according to the invention can be synthesized via a linker having three reactive groups (a trifunctional anchor compound) based on a glycerol fundamental substance ($C_3$ anchor) and having a monofunctional lipid, such as, for example, a palmityl residue, cholesterol or tocopherol. As starting material for the synthesis of the linker there can be used, for example, alpha,beta-isopropylidene-glycerol (a glycerol containing a ketal protecting group), which is preferably first converted into the alcoholate with sodium hydride and is reacted with hexadecyl bromide and a lipid in a Williamson synthesis to form the corresponding ether. Alternatively, the ether bond can be linked in the first step by a different method, for example by formation of a tosylate of α,β-isopropylidene-glycerol, and reaction of the tosylate with the reactive group of a lipid, for example an acidic proton, to form the corresponding ether. In a second stage, the ketal protecting group can be removed with an acid, for example acetic acid, dilute hydrochloric acid, etc., and then the primary hydroxy group of the diol can be protected selectively by dimethoxytrityl chloride (DMT-Cl). In the last stage, the reaction of the product obtained in the preceding step with succinic anhydride is preferably carried out to form the succinate with DMAP as catalyst. Such a linker is particularly suitable, for example, for the binding of palmityl residues or tocopherol as lipid.

According to another alternative, the 3'-lipid modification of a nucleic acid molecule of either formula (I), (Ia), (II), (IIa), (IIIb), (IIIa) and/or (IIIb) according to the invention as defined above, is effected using a (bifunctional) lipid, such as, for example, polyethylene glycol (PEG) or hexaethylene glycol (HEG), without using a linker as described above. Such bifunctional lipids typically have two functional groups as described above, wherein one end of the bifunctional lipid can preferably be bound to the carrier material via a (coupling) molecule, for example a base-labile succinyl anchor, etc., as described herein, and the nucleic acid molecule of either formula (I), (Ia), (II), (IIa), (IIIb), (IIIa) and/or (IIIb) according to the invention as defined above can be synthesized at the other end of the bifunctional lipid (E. Bayer, M. Maier, K. Bleicher, H.-J. Gaus Z Naturforsch. 50b (1995) 671). By the omission of the third functionalisation and of a linker, respectively, as used hereinbefore, the synthesis of such a lipid-modified nucleic acid molecule according to the invention is simplified. For the preparation, the bifunctional lipid used according to the invention, for example polyethylene glycol, is typically first monosubstituted with a protecting group, for example DMT. In a second stage, esterification of the lipid protected at a reactive group is usually carried out with succinic anhydride, with DMAP catalysis, to form the succinate. Thereafter, in a third stage, the bifunctional lipid can be coupled to a carrier material and deprotected, following which the synthesis of the nucleic acid molecule of either formula (I), (Ia), (II), (IIa), (IIIb), (IIIa) and/or (IIIb) according to the invention as defined above takes place in a fourth step in accordance with a process as described hereinbefore. Deprotection of the synthesized nucleic acid molecule of either formula (I), (Ia), (II), (IIa), (IIIb), (IIIa) and/or (IIIb) according to the invention as defined above and cleavage of the lipid-modified nucleic acid from the carrier material are then optionally carried out.

According to another preferred embodiment, the lipid modification of a nucleic acid molecule of either formula (I), (Ia), (II), (IIa), (IIIb), (IIIa) and/or (IIIb) according to the invention as defined above, takes place at the 5' end of the nucleic acid. The lipid modification is thereby typically carried out either after the provision or after the synthesis of the nucleic acid molecule of either formula (I), (Ia), (II), (IIa), (IIIb), (IIIa) and/or (IIIb) according to the invention as defined above. The provision of the nucleic acid molecule of either formula (I), (Ia), (II), (IIa), (IIIb), (IIIa) and/or (IIIb) according to the invention as defined above can be carried out—as defined above—via a direct synthesis of the nucleic acid molecule of either formula (I), (Ia), (II), (IIa), (IIIb), (IIIa) and/or (IIIb) according to the invention as defined above or by addition of a ready synthesized nucleic acid molecule of either formula (I), (Ia), (II), (IIa), (IIIb), (IIIa) and/or (IIIb) according to the invention as defined above. A synthesis of the nucleic acid molecule of either formula (I), (Ia), (II), (IIa), (IIIb), (IIIa) and/or (IIIb) according to the invention as defined above takes place, preferably analogously to the method described above, according to processes of nucleic acid synthesis known in the prior art, more preferably according to the phosphoramidite process.

According to a particularly preferred embodiment, the lipid modification of a nucleic acid molecule of either formula (I), (Ia), (II), (IIa), (IIIb), (IIIa) and/or (IIIb) according to the invention as defined above takes place at the 5' end of the nucleic acid molecule according to the invention by specially modified phosphoramidites following a phosphoramidite process for the synthesis of the nucleic acid. Such amidites, which are obtainable quite simply by synthesis, are conventionally coupled as the last monomer to a commercially available or to a ready synthesized nucleic acid. These reactions are distinguished by a rather rapid reaction kinetics and very high coupling yields. The synthesis of the modified amidites preferably takes place by reaction of a phosphoramidite, for example beta-cyanoethyl-monochlorophosphoramidite (phosphorous acid mono-(2-cyanoethyl ester)-diisopropyl-amide chloride), with an alcohol, dissolved in a suitable solvent, for example in absolute dichloromethane, of a lipid as defined above, for example a lipid alcohol of tocopherol, cholesterol, hexadecanol, DMT-PEG, etc. Likewise preferably, DIPEA is added to the reaction solution as acid acceptor.

These phosphoramidites used for the synthesis of the 5'-lipid-modified nucleic acids according to the invention are relatively resistant to hydrolysis and can (prior to the synthesis) be purified chromatographically by means of silica gel. To this end, a small amount of a weak base, such as, for example, triethylamine, is typically added to the eluent in order to avoid decomposition of the amidite. It is important that this base is removed completely from the product again, in order to avoid poor coupling yields. This can be carried out, for example, by simple drying in vacuo, but preferably by purification of the phosphoramidites by precipitation thereof from tert-butyl methyl ether using pentane. If the lipid-modified amidites used have a very high viscosity, for example are present in the form of a viscous oil, (rapid) column chromatography can also be carried out, which makes it possible to dispense with triethylamine as base. Such a purification is typically not carried out in the case of PEG-modified amidites, however, because they contain the acid-labile DMT protecting group.

For the coupling reaction of the lipid-modified phosphoramidites to the 5' end of a nucleic acid molecule of either formula (I), (Ia), (II), (IIa), (IIIb), (IIIa) and/or (IIIb) according to the invention as defined above there are preferably used those solvents in which the amidites used are sufficiently soluble. For example, owing to the high lipophilicity of the amidites used according to the invention, their solubility in acetonitrile can be limited. Apart from acetonitrile as the solvent that is typically used, a solution of chlorinated hydrocarbons is therefore preferably used for the coupling reactions, for example a 0.1 M solution in (absolute) dichloromethane. The use of dichloromethane requires some changes to the standard protocol of the synthesis cycle, however. For example, in order to avoid precipitation of the amidite in the pipes of the automatic synthesis device and on the carrier material, all the valves and pipes that come into contact with the amidite are flushed with (absolute) dichloromethane before and after the actual coupling step and blown dry.

When lipid-modified amidites are used, high coupling yields are typically obtained, which are comparable with the coupling yield of amidites conventionally used in the prior art. The kinetics of the reaction of lipid-modified amidites generally proceeds more slowly. For this reason, the coupling times are preferably (markedly) lengthened when lipid-modified amidites are used, as compared with standard protocols. Such coupling times can easily be determined by a person skilled in the art. Because a capping step after the coupling can be omitted, it is likewise possible, if required, to carry out a further synthesis cycle with the same lipid-modified amidite, in order to increase the overall yield of the reaction. In this case, the detritylation step is not usually carried out, for example in the case of DMT-modified lipids such as DMT-PEG.

In the synthesis of 5'-lipid-modified nucleic acid molecules according to the invention, the phosphite triester via which the lipid is bound to the nucleic acid molecule of either formula (I), (Ia), (II), (IIa), (IIIb), (IIIa) and/or (IIIb) according to the invention as defined above can be oxidised by a sulfurising agent. To this end there is preferably used a sulfurising agent that achieves oxidation of the phosphotriester as completely as possible. Otherwise, the sulfurisation reaction, for example for steric reasons, may proceed so incompletely that only a small amount of product, or no product at all, is obtained after the ammoniacal cleavage and deprotection of the MON. This phenomenon is dependent on the type of modification, the sulfurising agent used and the sulfurisation conditions. The oxidation is therefore carried out preferably with iodine. As a result, although a phosphodiester bond is introduced, it is not to be expected, owing to the proximity of the lipid residue, that this bond will be recognised as a substrate by nucleases.

In a lipid modification, linkers or (bifunctional) lipids contained in the nucleic acid molecule of either formula (I), (Ia), (II), (IIa), (IIIb), (IIIa) and/or (IIIb) according to the invention as defined above, or optionally the nucleic acid molecule of either formula (I), (Ia), (II), (IIa), (IIIb), (IIIa) and/or (IIIb) according to the invention as defined above itself, can, as described hereinbefore, be coupled directly or indirectly to a carrier material. Direct coupling is carried out preferably directly with the carrier material, while indirect coupling to the carrier material is typically carried out via a further (coupling) molecule. The bond formed by the coupling to a carrier material preferably exhibits a (cleavable) covalent bond with the linker or bifunctional lipid and/or a (cleavable) covalent bond with the solid phase. Compounds suitable as (coupling) molecule are, for example, dicarboxylic acids, for example succinyl residues (=succinyl anchors), oxalyl residues (=Oxalyl anchors), etc. Linkers, (bifunctional) lipids or optionally nucleic acids of either formula (I), (Ia), (II), (IIa), (IIIb), (IIIa) and/or (IIIb) according to the invention as defined above which, like, for example, aminoalkyl residues (e.g. aminopropyl or aminohexanyl residues), carry a free amino function, can be bound to the carrier material via a phthalimide linker. Thiol-containing linkers, (bifunctional) lipids or optionally nucleic acids of either formula (I), (Ia), (II), (IIa), (IIIb), (IIIa) and/or (IIIb) according to the invention as defined above can be bound in disulfide form to the carrier material. Suitable carrier materials in connection with this invention are in particular solid phases such as CPG, Tentagel®, amino-functionalised PS-PEG (Tentagel® S $NH_2$), etc., preferably Tentagel® or amino-functionalised PS-PEG (Tentagel® S $NH_2$). According to a particular embodiment it is possible for the coupling to a carrier material to couple, for example, the succinates of the described linkers or bifunctional lipids used according to the invention, preferably with TBTU/NMM (1H-benzotriazol-1-yl-1,1,3,3-tetramethyluronium tetrafluoroborate/N-methylmorpholine) as coupling reagent, to amino-functionalised PS-PEG (Tentagel® S $NH_2$). In the case of PS-PEG carrier materials on the 1 µmol scale that is conventionally used, the best results are typically obtained with loads of from 50 to 100 µmol/g (E. Bayer, K. Bleicher, M. Maier Z Naturforsch. 50b (1995) 1096). If, however, nucleotides are to be synthesized on a large scale according to the invention, the loading of the carrier materials is preferably as high as possible (≥100 µmol). According to the invention, such a process likewise results in good coupling yields (M. Gerster, M. Maier, N. Clausen, J. Schewitz, E. Bayer Z. Naturforsch. 52b (1997) 110). For example, carrier materials such as, for example, resins with a load of up to 138 µmol/g or optionally more can be used with good synthesis yields. Because the coupling yields with the above-described linkers or bifunctional lipids are approximately 100%, the loading of the carrier material can be adjusted relatively precisely via the stoichiometry of these compounds. The loading is preferably monitored by spectroscopic quantification of the cleaved DMT protecting group (see experimental part). The residual amino functions still present on the carrier material can be capped with acetic anhydride. This capping is normally carried out following the loading of the carrier material but can also take place directly in the nucleic acid synthesis, for example in a DNA synthesizer. For the synthesis of lipid-modified nucleic acids on the derivatised PS-PEG carrier materials there are preferably used synthesis cycles developed specifically for Tentagel®, which take into account the characteristic properties of the material (E. Bayer, M. Maier, K. Bleicher, H.-J. Gaus Z. Naturforsch. 50b (1995) 671, E. Bayer, K. Bleicher, M. Maier Z. Naturforsch. 50b (1995) 1096). Preferred changes as compared with the standard protocol include:

lengthened reaction times in the coupling, capping and oxidation steps;
increased number of detritylation steps;
lengthened washing steps after each step;
use of an ascorbic-acid-containing washing solution (0.1 M in dioxane/water=9:1) after the oxidation step that is usually necessary (for oxidation of the phosphite triester) during the amidite process, in order to remove traces of iodine.

It should be noted that the nature of the modification can have an influence on the individual steps of the synthesis cycle. For example, in the case of $PEG_{1500}$-derivatised carrier materials, a considerably slowed reaction kinetics is observed, which requires the detritylation steps to be lengthened again and the coupling time to be lengthened in addition. Such changes and adaptations are within the scope of the normal capability of a person skilled in the art and can be carried out at any time within the context of the present disclosure. With these reaction cycles so modified, both lipid-modified phosphorodiesters and phosphorothioates can be synthesized. The coupling yields of amidites on linkers or bifunctional lipids used according to the invention are not impaired by the lipid residues but correspond to conventional values (97-99%). The possibility of 5' derivatisation and the introduction of further modifications, for example at base, sugar or phosphate backbone, is retained when such 3' modifications are used.

The nucleic acid molecule of either formula (I), (Ia), (II), (IIa), (IIIb), (IIIa) and/or (IIIb) according to the invention as defined above, as chemically unmodified nucleic acid or as (chemically) modified nucleic acid, e.g. as a lipid modified nucleic acid molecule of either formula (I), (Ia), (II), (IIa), (IIIb), (IIIa) and/or (IIIb) according to the invention as defined above, can likewise be stabilized by forming a complex of the nucleic acid molecule of either formula (I), (Ia), (II), (IIa), (IIIb), (IIIa) and/or (IIIb) according to the invention as defined above, e.g., without being limited thereto, with a cationic polymer, cationic peptides or polypeptides, preferably with a polycationic polymer such as polylysine or polyarginine or alternatively with cationic lipids or lipofectants, with a histone, a nucleoline, protamine, oligofectamine, spermine or spermidine, and cationic polysaccharides, in particular chitosan, TDM, MDP, muramyl dipeptide, pluronics, and/or one of the derivatives thereof, etc. Histones and protamines are cationic proteins which naturally compact DNA. They are thus responsible in vivo for the condensation of non-transcribed DNA and the DNA of certain viruses. As histones which may be used in the context of the present invention to form a complex with the nucleic acid molecule of either formula (I), (Ia), (II), (IIa), (IIIb), (IIIa) and/or (IIIb) according to the invention as defined above, mention may be made more particularly of histones H1, H2a, H3 and H4. However, protamin (protamin P1 or P2) or cationic partial sequences of protamine are specifically preferred. In the context of the present invention, the compound may advantageously be represented by a peptide sequence derived from the protamin P1 or P2, and more precisely corresponding to the (cationic) sequence (SRSRYYRQRQRSRRRRRRR (SEQ ID NO: 109) or RRRLHRIHRRQHRSCRRRKRR (SEQ ID NO: 110). Other compounds suitable for forming a complex with the nucleic acid molecule of either formula (I), (Ia), (II), (IIa), (IIIb), (IIIa) and/or (IIIb) according to the invention as defined above according to the invention may be selected from the adjuvant compounds as defined herein, without being limited thereto.

In this context, "forming a complex" shall mean that the nucleic acid molecule of either formula (I), (Ia), (II), (IIa), (IIIb), (IIIa) and/or (IIIb) according to the invention as defined above is bound to a stabilizing compound as defined above, e.g. a cationic polymer, cationic peptides or polypeptides, etc. by forming a non-covalent complex between nucleic acid and stabilizing compound. Herein, "non-covalent" means that a reversible association of nucleic acid and stabilizing compound is formed by non-covalent interactions of these molecules, wherein the molecules are associated together by some type of interaction of electrons, other than a covalent bond, e.g. by van der Waals-bonds, i.e. a weak electrostatic attraction arising from a nonspecific attractive force of both molecules. Association of the nucleic acid molecule of either formula (I), (Ia), (II), (IIa), (IIIb), (IIIa) and/or (IIIb) according to the invention as defined above and the stabilizing compound is in equilibrium with dissociation of that complex. Without being bound to any theory, it is expected that the equilibrium is intracellularly shifted towards dissociated nucleic acid molecule of either formula (I), (Ia), (II), (IIa), (IIIb), (IIIa) and/or (IIIb) according to the invention as defined above and the stabilizing compound.

According to an embodiment, the nucleic acid molecule of either formula (I), (Ia), (II), (IIa), (IIIb), (IIIa) and/or (IIIb) according to the invention as defined above can be an immunostimulating agent, if administered without any other pharmaceutically active component, or may be used as an adjuvant, if administered together with a pharmaceutically active component, e.g. as a composition containing both the pharmaceutically active component and the adjuvant component (e.g. a vaccine composition containing a specific antigen and a nucleic acid molecule according to either formula (I), (Ia), (II), (IIa), (IIIb), (IIIa) and/or (IIIb) according to the invention as defined above as an adjuvant).

A nucleic acid molecule of either formula (I), (Ia), (II), (IIa), (IIIb), (IIIa) and/or (IIIb) according to the invention as defined above as an "immunostimulating agent" is preferably capable of triggering a non-antigen-specific, immune reaction (as provided by the innate immune system), preferably in an immunostimulating manner. An immune reaction can generally be brought about in various ways. An important factor for a suitable immune response is the stimulation of different T-cell sub-populations. T-lymphocytes typically differentiate into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the immune response. In connection with the present invention, the Th1/Th2 ratio of the immune response is preferably displaced by the immunostimulating agent, namely the nucleic acid molecule of either formula (I), (Ia), (II), (IIa), (IIIb), (IIIa) and/or (IIIb) according to the invention as defined above in the direction towards the cellular response, that is to say the Th1 response, and a predominantly cellular immune response is thereby induced. As defined above, the nucleic acid of the invention exerts by itself an unspecific immune response, which allows the nucleic acid to be used as such (without adding another pharmaceutically active component) as an immunostimulating agent. If administered together with another pharmaceutically active component, preferably a specifically immunostimulating component, the nucleic acid of the invention serves as an adjuvant supporting the specific immune response elicited by the other pharmaceutically active component.

The present invention also relates to pharmaceutical compositions containing at least one inventive nucleic acid molecule of either formula (I), (Ia), (II), (IIa), (IIIb), (IIIa) and/or (IIIb) according to the invention as defined above and optionally a (compatible) pharmaceutically acceptable carrier and/or further auxiliary substances and additives and/or adjuvants (first embodiment of an inventive composition). Moreover, the present invention relates to pharmaceutical compositions containing at least one nucleic acid molecule of either formula (I), (Ia), (II), (IIa), (IIIb), (IIIa) and/or (IIIb) according to the invention as defined above, e.g. one, two three, four six seven, or more nucleic acid molecules thereof, a pharmaceutically active component and optionally a pharmaceutically acceptable carrier and/or further auxiliary substances and additives and/or adjuvants (second embodiment of an inventive composition).

The pharmaceutical compositions according to the present invention typically comprise a safe and effective amount of at least one nucleic acid molecule of either formula (I), (Ia), (II), (IIa), (IIIb), (IIIa) and/or (IIIb) according to the invention as defined above, or one, two three, four six seven, or more nucleic acids thereof. As used here, "safe and effective amount" means an amount of each or all nucleic acids of either formula (I), (Ia), (II), (IIa), (IIIb), (IIIa) and/or (IIIb) according to the invention as defined above in the composition, that is sufficient to significantly induce a positive modification of a condition to be treated, for example of a tumour, autoimmune diseases, allergies or infectious disease, etc. At the same time, however, a "safe and effective amount" is small enough to avoid serious side-effects, that are to say to permit a sensible relationship between advantage and risk. The determination of these limits typically lies within the scope of sensible medical judgment. In relation to the nucleic acid molecule of either formula (I), (Ia), (II), (IIa), (IIIb), (IIIa) and/or (IIIb) according to the invention as defined above, the expression "safe and effective amount" preferably means an amount that is suitable for stimulating the immune system in such a manner that no excessive or damaging immune reactions are achieved but, preferably, also no such immune reactions below a measurable level. A "safe and effective amount" of the nucleic acid molecule of either formula (I), (Ia), (II), (IIa), (IIIb), (IIIa) and/or (IIIb) according to the invention as defined above, will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The pharmaceutical compositions according to the invention can be used according to the invention for human and also for veterinary medical purposes.

According to the first embodiment, the above-described nucleic acid molecule of either formula (I), (Ia), (II), (IIa), (IIIb), (IIIa) and/or (IIIb) according to the invention as defined above, can by itself be the immunostimulating agent (without addition of any other pharmaceutically active components). This holds in particular, if the nucleic acid molecule of either formula (I), (Ia), (II), (IIa), (IIIb), (IIIa) and/or (IIIb) according to the invention as defined above contains a lipid modification. The lipid may further enhance the immunostimulatory properties of the inventive nucleic acids or may well form a therapeutically active molecule, such as, for example, a vitamin, or steroid, as described above, for example alpha-tocopherol (vitamin E), D-alpha-tocopherol, L-alpha-tocopherol, D,L-alpha-tocopherol, vitamin E succinate (VES), vitamin A and its derivatives, vitamin D and its derivatives, vitamin K and its derivatives, etc.

The pharmaceutical composition according to the second embodiment of the invention may contain (in addition to the at least one nucleic acid molecule of either formula (I), (Ia), (II), (IIa), (IIIb), (IIIa) and/or (IIIb) according to the invention as defined above) at least one additional pharmaceutically active component. A pharmaceutically active component in this connection is a compound that has a therapeutic effect against a particular indication, preferably cancer diseases, autoimmune disease, allergies or infectious diseases. Such compounds include, without implying any limitation, peptides, proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions; modified, attenuated or de-activated (e.g. chemically or by irradiation) pathogens (virus, bacteria etc.) etc.

According to a first alternative of the second embodiment (of a composition according to the invention), the pharmaceutically active component contained in the pharmaceutical composition is an immunomodulatory component, preferably an immuno-stimulatory component. Most preferably, the pharmaceutically active component is an antigen or immunogen. An "antigen" and an "immunogen" are to be understood as being any structure that is able to bring about the formation of antibodies and/or the activation of a cellular immune response, that is to say a specific (and not an adjuvant) immune response. According to the invention, therefore, the terms "antigen" and "immunogen" are used synonymously. Examples of antigens are peptides, polypeptides, that is to say also proteins, cells, cell extracts, polysaccharides, polysaccharide conjugates, lipids, glycolipids and carbohydrates. There come into consideration as antigens, for example, tumour antigens, animal, herbal, viral, bacterial, fungal and protozoological antigens, autoimmune antigens or allergens. Preference is given to surface antigens of tumour cells and surface antigens, in particular secreted forms, of viral, bacterial, fungal or protozoological pathogens. The antigen can, of course, be present, for example in a vaccine according to the invention, also as a haptene coupled to a suitable carrier. Other antigenic components, e.g. deactivated or attenuated pathogens (as described above), may be used as well.

Antigenic (poly)peptides include all known antigenic peptides, for example tumour antigens, etc. Specific examples of tumour antigens are inter alia tumour-specific surface antigens (TSSAs), for example 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class 1/m, NA88-A, N-acetylglucosaminyltransferase-V, Neo-PAP, Neo-PAP/m, NFYC/m, NGEP, NMP22, NPM/ALK, N-Ras/ m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaR11, TGM-4, TPI/m, TRAG-3, TRG, TRP-1, TRP-2/6b, TRP/INT2, TRP-p8, tyrosinase, UPA, VEGF, VEGFR-2/FLK-1, and WT1. Any class of tumor antigens is suitable for the purpose of the present invention, e.g. tumor antigens known to be involved in neovascularization, influencing the extracellular matrix structure etc. The tumor antigens may be provided in the pharmaceutical composition as protein or peptide antigen or as mRNA or DNA encoding the tumor antigens or epitopes thereof, preferably the above tumor antigens.

By a second alternative of the second embodiment (for a composition according to the invention containing the inventive nucleic acid (as an adjuvant) and the additional pharmaceutically active component) the pharmaceutically active component is an antibody. In this connection, any therapeutically suitable antibody can be used. Particular preference is given according to the invention to an antibody directed against antigens, proteins or nucleic acids that play an important part in cancer diseases or infectious diseases, for example cell surface proteins, tumour suppressor genes or inhibitors thereof, growth and elongation factors, apoptosis-relevant proteins, tumour antigens, or antigens as described hereinbefore, etc.

According to a third alternative of the second embodiment, the pharmaceutically active component contained in the pharmaceutical composition according to the invention is a nucleic acid. Such a nucleic acid can be single-stranded or double-stranded and can be in the form of a homo- or heteroduplex and also in linear or circular form. A nucleic acid contained as a pharmaceutically active component in the pharmaceutical composition is not limited in terms of its length and can include any naturally occurring nucleic acid sequence or its complement or a fragment thereof. Likewise, the nucleic acid used in this connection can be partially or wholly of synthetic nature. For example, the nucleic acid can include a nucleic acid that codes for a (therapeutically relevant) protein and/or that is capable of bringing about an immune reaction, for example an antigen or a nucleic acid coding for an antigen. An antigen here is preferably an antigen as described hereinbefore.

Preferably, the nucleic acid contained as a pharmaceutically active component in the pharmaceutical composition according to the invention is an mRNA. Such an mRNA can be added in its naked form to the pharmaceutical composition according to the invention or in a stabilized form that reduces or even prevents the degradation of the nucleic acid in vivo, for example by exo- and/or endo-nucleases.

For example, the mRNA contained as a pharmaceutically active component in the pharmaceutical composition according to the invention can be stabilized by an above-defined 5' Cap, and alternatively or additionally by a poly-A tail and/or a poly-C tail at the 3' end of at least 50 nucleotides, preferably at least 70 nucleotides, more preferably at least 100 nucleotides, particularly preferably at least 200 nucleotides. As already mentioned, the terminal structure is of critical importance in vivo. The RNA is recognised as mRNA via these structures and the degradation is regulated. In addition, however, there are further processes that stabilize or destabilize RNA. Many of these processes are still unknown, but an interaction between the RNA and proteins often appears to be decisive therefor. For example, an "mRNA surveillance system" has recently been described (Hellerin and Parker, Ann. Rev. Genet. 1999, 33: 229 to 260), in which incomplete or non-sense mRNA is recognised by particular feedback protein interactions in the cytosol and is made amenable to degradation, a majority of these processes being carried out by exonucleases.

The stabilization of the mRNA contained as a pharmaceutically active component in the pharmaceutical composition according to the invention can likewise by carried out by associating or complexing the mRNA with, or binding it to, a cationic compound, in particular a polycationic compound, for example a (poly)cationic peptide or protein. In particular the use of protamine, nucleoline, spermin or spermidine as the polycationic (nucleic-acid-binding) protein is particularly effective. Furthermore, the use of other cationic peptides or proteins, such as poly-L-lysine or histones, is likewise possible. This procedure for stabilizing mRNA is described in EP-A-1083232, the disclosure of which is incorporated by reference into the present invention in its entirety. Further preferred cationic substances which can be used for stabilizing the mRNA present as a pharmaceutically active component include cationic compounds as disclosed herein in connection with adjuvants, which are suitable for depot and delivery of the inventive nucleic acid, e.g. cationic polysaccharides, for example chitosan, polybrene, polyethyleneimine (PEI) or poly-L-lysine (PLL), etc. Apart from the action of the lipid-modified nucleic acid molecule of either formula (I), (Ia), (II), (IIa), (IIIb), (IIIa) and/or (IIIb) in the form of an adjuvant in improving cell permeability, which is already advantageous, the association or complexing of the mRNA with cationic compounds, e.g. cationic proteins or cationic lipids, e.g. oligofectamine as a lipid based complexation reagent) preferably increases the transfer of the mRNA present as a pharmaceutically active component into the cells to be treated or into the organism to be treated. It is also referred to the disclosure herein with regard to the stabilizing effect for the nucleic acid molecule of the invention by complexation, which holds for the stabilization of mRNA as well.

Another approach to stabilize mRNA as a pharmaceutically active component in the pharmaceutical composition according to the invention is the targeted changing of the sequence of the mRNA by removing or changing so-called destabilizing sequence elements (DSEs). Signal proteins are able to bind to these destabilizing sequence elements (DSEs), which occur in eukaryotic mRNA in particular, and regulate the enzymatic degradation of the mRNA in vivo. Therefore, in order further to stabilize an mRNA present as a pharmaceutically active component, one or more changes are preferably made as compared with the corresponding region of the wild-type mRNA, so that no destabilizing sequence elements are present. Of course, it is likewise preferred according to the invention to eliminate DSEs optionally present in the untranslated regions (3'- and/or 5'-UTR) from the mRNA. Examples of the above DSEs are AU-rich sequences ("AURES"), which occur in 3'-UTR sections of numerous unstable mRNAs (Caput et al., Proc. Natl. Acad. Sci. USA 1986, 83: 1670 to 1674). The mRNA used as a pharmaceutically active component is therefore preferably modified as compared with the wild-type mRNA in such a manner that it does not contain any such destabilizing sequences. This is also true of those sequence motifs that are recognised by possible endonucleases, for example the sequence GAACAAG, which is contained in the 3'-UTR segment of the gene coding for the transferrin receptor (Binder et al., EMBO J. 1994, 13: 1969 to 1980). Such sequence motifs are preferably also eliminated from the lipid-modified nucleic acid molecule according to the invention.

The mRNA as a pharmaceutically active component in the pharmaceutical composition according to the invention can further be modified, for example for an efficient translation that may be desired, in such a manner that effective binding of the ribosomes to the ribosomal binding site (Kozak sequence: GCCGCCACCAUGG (SEQ ID NO: 111), the AUG forms the start codon) takes place. It has been noted in this connection that an increased A/U content around this position permits more efficient ribosome binding to the mRNA.

Furthermore, it is possible to introduce one or more so-called IRES (internal ribosome entry side(s)) (sequences) into the mRNA used as a pharmaceutically active component. An IRES can thus function as the only ribosomal binding site, but it can also serve to provide an mRNA that codes for a plurality of peptides or polypeptides which are to be translated independently of one another by the ribosomes ("multicistronic mRNA"). Examples of IRES sequences which can be used according to the invention are those from picorna viruses (e.g. FMDV), plague viruses (CFFV), polio viruses (PV), encephalo-myocarditis viruses (ECMV), foot-and-mouth viruses (FMDV), hepatitis C viruses (HCV), conventional swine fever viruses (CSFV), murine leukoma virus (MLV), simean immune deficiency virus (SIV) or cricket paralysis viruses (CrPV).

The mRNA optionally used as a pharmaceutically active component in the pharmaceutical composition according to the invention can likewise contain in its 5'- and/or 3'-untranslated regions stabilizing sequences that are capable of increasing the half-life of the mRNA in the cytosol. These stabilizing sequences can exhibit 100% sequence homology with naturally occurring sequences that occur in viruses, bacteria and eukaryotes, but they can also be partially or wholly of synthetic nature. As examples of stabilizing sequences which can be used in the present invention there may be mentioned the untranslated sequences (UTR) of the beta-globin gene, for example of Homo sapiens or Xenopus laevis. Another example of a stabilizing sequence has the general formula (C/U)CCAN$_x$CCC(U/A)Py$_x$UC(C/U)CC (SEQ ID NO: 112), which is contained in the 3'-UTR of the very stable mRNA that codes for α-globin, alpha-(I)-collagen, 15-lipoxygenase or for tyrosine-hydroxylase (see Holcik et al, Proc. Natl. Acad. Sci. USA 1997, 94: 2410 to 2414). Of course, such stabilizing sequences can be used individually or in combination with one another as well as in combination with other stabilizing sequences known to a person skilled in the art.

In order to further increase an eventually desired translation, the mRNA used as a pharmaceutically active component can exhibit the following modifications as compared with a corresponding wild-type mRNA, which modifications can be present either as alternatives or in combination with one another. On the one hand, the G/C content of the region of the modified mRNA coding for a peptide or polypeptide can be greater than the G/C content of the coding region of the wild-type mRNA coding for the peptide or polypeptide, the amino acid sequence coded for being unmodified compared with the wild type. This modification is based on the fact that, for an efficient translation of an mRNA, the stability of the mRNA as such is critical. The composition and sequence of the various nucleotides plays a large part thereby. In particular, sequences having an increased G(guanosine (guanine))/C(cytidine (cytosine)) content are more stable than sequences having an increased A(adenosine (adenine))/U(uridine (uracil)) content. According to the invention, therefore, while retaining the translated amino acid sequence, the codons are varied as compared with the wild-type mRNA in such a manner that they contain more G/C nucleotides. Because several codons code for the same amino acid (degeneracy of the genetic code) the codons that are advantageous for the stability can be determined (alternative codon usage). In dependence on the amino acid to be coded for by the mRNA, different possibilities for the modification of the mRNA sequence as compared to the wild-type sequence are possible. In the case of amino acids coded for by codons that contain solely G or C nucleotides, no modification of the codon is necessary. Accordingly, the codons for Pro (CCC or CCG), Arg (CGC or CGG), Ala (GCC or GCG) and Gly (GGC or GGG) do not require any change because no A or U is present. In the following cases, the codons that contain A and/or U nucleotides are changed by the substitution of different codons that code for the same amino acids but do not contain A and/or U. Examples are: the codons for Pro can be changed from CCU or CCA to CCC or CCG; the codons for Arg can be changed from CGU or CGA or AGA or AGG to CGC or CGG; the codons for Ala can be changed from GCU or GCA to GCC or GCG; the codons for Gly can be changed from GGU or GGA to GGC or GGG. In other cases, although A and U nucleotides cannot be eliminated from the codons, it is possible to reduce the A and U content by the use of codons that contain fewer A and/or U nucleotides. For example: the codons for Phe can be changed from UUU to UUC; the codons for Leu can be changed from UUA, CUU or CUA to CUC or CUG; the codons for Ser can be changed from UCU or UCA or AGU to UCC, UCG or AGC; the codon for Tyr can be changed from UAU to UAC; the stop codon UAA can be changed to UAG or UGA; the codon for Cys can be changed from UGU to UGC; the codon His can be changed from CAU to CAC; the codon for Gln can be changed from CAA to CAG; the codons for Ile can be changed from AUU or AUA to AUC; the codons for Thr can be changed from ACU or ACA to ACC or ACG; the codon for Asn can be changed from AAU to AAC; the codon for Lys can be changed from AAA to AAG; the codons for Val can be changed from GUU or GUA to GUC or GUG; the codon for Asp can be changed from GAU to GAC; the codon for Glu can be changed from GAA to GAG. In the case of the codons for Met (AUG) and Trp (UGG), on the other hand, there is no possibility of sequence modification. The substitutions listed above can, of course, be used individually but also in all possible combinations for increasing the G/C content of the modified mRNA as compared with the original sequence. Thus, for example, all codons for Thr occurring in the original (wild-type) sequence can be changed to ACC (or ACG). Preferably, however, combinations of the above substitution possibilities are used, for example: substitution of all codons in the original sequence coding for Thr to ACC (or ACG) and substitution of all codons originally coding for Ser to UCC (or UCG or AGC); substitution of all codons in the original sequence coding for Ile to AUC and substitution of all codons originally coding for Lys to AAG and substitution of all codons originally coding for Tyr to UAC; substitution of all codons in the original sequence coding for Val to GUC (or GUG) and substitution of all codons originally coding for Glu to GAG and substitution of all codons originally coding for Ala to GCC (or GCG) and substitution of all codons originally coding for Arg to CGC (or CGG); substitution of all codons in the original sequence coding for Val to GUC (or GUG) and substitution of all codons originally coding for Glu to GAG and substitution of all codons originally coding for Ala to GCC (or GCG) and substitution of all codons originally coding for Gly to GGC (or GGG) and substitution of all codons originally coding for Asn to AAC; substitution of all codons in the original sequence coding for Val to GUC (or GUG) and substitution of all codons originally coding for Phe to UUC and substitution of all codons originally coding for Cys to UGC and substitution of all codons originally coding for Leu to CUG (or CUC) and substitution of all codons originally coding for Gln to CAG and substitution of all codons originally coding for Pro to CCC (or CCG); etc. Preferably, the G/C content of the region (or of each other further section optionally present) of the mRNA that codes for the peptide or polypeptide is increased by at least 7% points, more preferably by at least 15% points, particularly preferably by at least 20% points, as compared with the G/C content of the coded region of the wild-type mRNA coding for the corresponding peptide or polypeptide and is preferably at least 50%, more preferably at least 70% and most preferably at least 90%. It is particularly preferred in this connection to increase the G/C content of the mRNA so modified in comparison with the wild-type sequence to the maximum possible degree.

A further preferred modification of an mRNA used as a pharmaceutically active component in the pharmaceutical composition is based on the finding that the translation efficiency is also determined by a different frequency in the occurrence of tRNAs in cells. If, therefore, so-called "rare" codons are present in an increased number in an RNA sequence, then the corresponding mRNA is translated markedly more poorly than in the case where codons coding for relatively "frequent" tRNAs are present. According to the invention, therefore, the coding region in the mRNA used as a pharmaceutically active component is modified as compared with the corresponding region of the wild-type mRNA in such a manner that at least one codon of the wild-type sequence that codes for a relatively rare tRNA in the cell is replaced by a codon that codes for a relatively frequent tRNA in the cell, which carries the same amino acid as the relatively rare tRNA. By means of this modification, the RNA sequences are so modified that codons are introduced for which frequently occurring tRNAs are available. Which tRNAs occur relatively frequently in the cell and which, by contrast, are relatively rare is known to a person skilled in the art; see, for example, Akashi, Curr. Opin. Genet. Dev. 2001, 11(6): 660-666. By means of this modification it is possible according to the invention to replace all codons of the wild-type sequence that code for a relatively rare tRNA in the cell by a codon that codes for a relatively frequent tRNA in the cell, which carries the same amino acid as the relatively rare tRNA. It is particularly preferred to combine the increased, in particular maximum, sequential G/C content in the mRNA as described above with the "frequent" codons, without changing the amino acid sequence of an antigenic peptide or polypeptide (one or more) coded for by the coding region of the mRNA. Preferred antigens, which may be coded by the G/C enriched/optimized mRNA, are listed above.

According to a fourth alternative of the second embodiment (for the composition of the present invention), the nucleic acid contained as a pharmaceutically active component in the pharmaceutical composition according to the invention is a dsRNA, preferably a siRNA. A dsRNA, or a siRNA, is of interest particularly in connection with the phenomenon of RNA interference. Attention was drawn to the phenomenon of RNA interference in the course of immunological research. In recent years, an RNA-based defense mechanism has been discovered, which occurs both in the kingdom of the fungi and in the plant and animal kingdom and acts as an "immune system of the genome". The system was originally described in various species independently of one another, first in C. elegans, before it was possible to identify the underlying mechanisms of the processes as being identical: RNA-mediated virus resistance in plants, PTGS (post-transcriptional gene silencing) in plants, and RNA interference in eukaryotes are accordingly based on a common procedure. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498). Recently, dsRNA molecules have also been used in vivo (McCaffrey et al. (2002), Nature 418: 38-39; Xia et al. (2002), Nature Biotech. 20: 1006-1010; Brummelkamp et al. (2002), Cancer Cell 2: 243-247).

The double-stranded RNA (dsRNA) eventually used as a pharmaceutically active component in the pharmaceutical composition according to the invention therefore preferably contains a sequence having the general structure 5'-($N_{17-29}$)-3', wherein N is any base and represents nucleotides. The general structure is composed of a double-stranded RNA having a macromolecule composed of ribonucleotides, the ribonucleotide comprising a pentose (ribose or deoxyribose), an organic base and a phosphate. The organic bases in the RNA here comprise the purine bases adenosine (adenine) (A) and guanosine (guanine) (G) and of the pyrimidine bases cytidine (cytosine) (C) and uridine (uracil) (U). The dsRNA eventually used as a pharmaceutically active component in the pharmaceutical composition according to the invention contains such nucleotides or nucleotide analogues having an oriented structure. dsRNAs used as a pharmaceutically active component according to the invention preferably have the general structure 5'-($N_{19-25}$)-3', more preferably 5L($N_{19-24}$)-3', yet more preferably 5'($N_{21-23}$)-3', wherein N is any base. Preferably at least 90%, more preferably 95% and especially 100% of the nucleotides of a dsRNA used as a pharmaceutically active component will be complementary to a section of the (m)RNA sequence of a (therapeutically relevant) protein or antigen described (as a pharmaceutically active component) hereinbefore. 90% complementary means that with a length of a dsRNA used according to the invention of, for example, 20 nucleotides, this contains not more than 2 nucleotides without corresponding complementarity with the corresponding section of the (m)RNA. The sequence of the double-stranded RNA optionally used in the pharmaceutical composition according to the invention is, however, preferably wholly complementary in its general structure with a section of the (m)RNA of a protein or antigen described as a pharmaceutically active component hereinbefore.

In principle, all the sections having a length of from 17 to 29, preferably from 19 to 25, base pairs that occur in the coding region of the (m)RNA can serve as target sequence for a dsRNA eventually used as a pharmaceutically active component in the pharmaceutical composition according to the invention. Equally, dsRNAs used as a pharmaceutically active component can also be directed against nucleotide sequences of a (therapeutically relevant) protein or antigen described (as a pharmaceutically active component) hereinbefore that do not lie in the coding region, in particular in the 5' non-coding region of the (m)RNA, for example, therefore, against non-coding regions of the (m)RNA having a regulatory function. The target sequence of the dsRNA used as a pharmaceutically active component of a protein or antigen described hereinbefore can therefore lie in the translated and untranslated region of the (m)RNA and/or in the region of the control elements. The target sequence of a dsRNA used as a pharmaceutically active component in the pharmaceutical composition according to the invention can also lie in the overlapping region of untranslated and translated sequence; in particular, the target sequence can comprise at least one nucleotide upstream of the start triplet of the coding region of the (m)RNA.

A modified nucleotide can preferably occur in a dsRNA eventually used as a pharmaceutically active component in the pharmaceutical composition according to the invention. The expression "modified nucleotide" means according to the invention that the nucleotide in question has been chemically modified. The person skilled in the art understands by the expression "chemical modification" that the modified nucleotide has been changed in comparison with naturally occurring nucleotides by the replacement, addition or removal of one or more atoms or atom groups. At least one modified nucleotide in dsRNA used according to the invention serves on the one hand for stability and on the other hand to prevent dissociation. Preferably, from 2 to 10 and more preferably from 2 to 5 nucleotides in a dsRNA used according to the invention have been modified. Advantageously, at least one 2'-hydroxy group of the nucleotides of the dsRNA in the double-stranded structure has been replaced by a chemical group, preferably a 2'-amino or a 2'-methyl group. At least one nucleotide in at least one strand of the double-stranded structure can also be a so-called "locked nucleotide" having a sugar ring that has been chemically modified, preferably by a 2'-O, 4'-C-methylene bridge. Several nucleotides of the dsRNA used according to the invention are advantageously locked nucleotides. Moreover, by modification of the backbone of a dsRNA used according to the invention, premature degradation thereof can be prevented. Particular preference is given in this connection to a dsRNA that has been modified in the form of phosphorothioate, 2'-O-methyl-RNA, LNA, LNA/DNA gapmers, etc. and therefore has a longer half-life in vivo.

The ends of the double-stranded RNA (dsRNA) used as a pharmaceutically active component in the pharmaceutical composition according to the invention can preferably be modified in order to counteract degradation in the cell or dissociation into the individual strands, in particular in order to avoid premature degradation by nucleases. A normally undesirable dissociation of the individual strands of dsRNA occurs in particular when low concentrations thereof or short chain lengths are used. For the particularly effective inhibition of dissociation, the cohesion, effected by the nucleotide pairs, of the double-stranded structure of dsRNA used according to the invention can be increased by at least one, preferably more than one, chemical linkage(s). A dsRNA used as a pharmaceutically active component in the pharmaceutical composition according to the invention whose dissociation has been reduced has higher stability towards enzymatic and chemical degradation in the cell or in the organism (in vivo) or ex vivo and therefore has a longer half-life. A further possibility for preventing premature dissociation in the cell of dsRNA used according to the invention consists in forming hairpin loop(s) at each end of the strands. In a particular embodiment, a dsRNA used in the pharmaceutical composition according to the invention therefore has a hairpin structure in order to slow the dissociation kinetics. In such a structure, a loop structure is formed preferably at the 5' and/or 3' end. Such a loop structure has no hydrogen bridges, and typically therefore no complementarity, between nucleotide bases. Typically, such a loop has a length of at least 5, preferably at least 7 nucleotides and in that manner links the two complementary individual strands of a dsRNA used according to the invention. In order to prevent dissociation of the strands, the nucleotides of the two strands of the dsRNA used according to the invention can likewise preferably be so modified that strengthening of the hydrogen bridge bond is achieved, for example by increasing the hydrogen bridge bond capacity between the bases by optionally modified nucleotides. As a result, the stability of the interaction between the strands is increased and the dsRNA is protected against attack by RNases.

According to a particularly preferred embodiment, the dsRNA used as a pharmaceutically active component in the pharmaceutical composition according to the invention is directed against the (m)RNA of a protein or antigen as described hereinbefore. The dsRNA used thereby preferably suppresses the translation of an above-described protein or antigen in a cell to the extent of at least 50%, more preferably 60%, yet more preferably 70% and most preferably at least 90%, that is to say the cell contains preferably not more than half of the naturally occurring (without treatment with dsRNA used according to the invention) cellular concentration of an above-described protein or antigen. The suppression of the translation of these proteins or antigens in cells after addition of dsRNA molecules used according to the invention is based on the phenomenon of RNA interference caused by such molecules. The dsRNA used according to the invention is then a so-called siRNA, which triggers the phenomenon of RNA interference and can bind the (m)RNA of an above-described protein or antigen. Measurement or demonstration of the translation suppression triggered in cells by the dsRNA used according to the invention can be carried out by Northern blot, quantitative real-time PCR or, at protein level, with specific antibodies against an above-described protein or antigen. The dsRNA eventually used as a pharmaceutically active component in the pharmaceutical composition according to the invention, and a corresponding siRNA, can be prepared by processes known to a person skilled in the art.

The pharmaceutical composition (according to the first or the second embodiment) according to the invention typically contains a (compatible) pharmaceutically acceptable carrier. The expression "(compatible) pharmaceutically acceptable carrier" used here preferably includes the liquid or non-liquid basis of the composition. The term "compatible" as used herein means that the constituents of the pharmaceutical composition are capable of being mixed with the pharmaceutically active component, with the nucleic acid of the invention as immunostimulating agent or as an adjuvant as such and with one another component in such a manner that no interaction occurs which would substantially reduce the pharmaceutical effectiveness of the composition under usual use conditions. Pharmaceutically acceptable carriers must, of course, have sufficiently high purity and sufficiently low toxicity to make them suitable for administration to a person to be treated.

If the composition is provided in liquid form, the pharmaceutically acceptable carrier will typically comprise one or more (compatible) pharmaceutically acceptable liquid carriers. The composition may comprise as (compatible) pharmaceutically acceptable liquid carriers e.g. pyrogen-free water; isotonic saline or buffered (aqueous) solutions, e.g phosphate, citrate etc. buffered solutions, vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid, etc. Particularly for injection of the inventive pharmaceutical composition, a buffer, preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$) and optionally potassium chloride (KCl), wherein further anions may be present additional to the chlorides. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the aforementioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

If the composition is provided in solid form, the pharmaceutically acceptable carrier will typically comprise one or more (compatible) pharmaceutically acceptable solid carriers. The composition may comprise as (compatible) pharmaceutically acceptable solid carriers e.g. one or more compatible solid or liquid fillers or diluents or encapsulating compounds may be used as well, which are suitable for administration to a person. Some examples of such (compatible) pharmaceutically acceptable solid carriers are e.g. sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulphate, etc.

The choice of a (compatible) pharmaceutically acceptable carrier is determined in principle by the manner in which the pharmaceutical composition according to the invention is administered. The pharmaceutical composition according to the invention can be administered, for example, systemically. Routes for administration include, for example, oral, subcutaneous, intravenous, intramuscular, intra-articular, intrasynovial, intrasternal, intrathecal, intrahepatic, intralesional, intracranial, transdermal, intradermal, intrapulmonal, intraperitoneal, intracardial, intraarterial, and sublingual topical and/or intranasal routes. The suitable amount of the pharmaceutical composition to be used can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those, which are suitable for use in lotions, creams, gels and the like. If the compound is to be administered perorally, tablets, capsules and the like are the preferred unit dose form. The pharmaceutically acceptable carriers for the preparation of unit dose forms, which can be used for oral administration are well known in the prior art. The choice thereof will depend on secondary considerations such as taste, costs and storability, which are not critical for the purposes of the present invention, and can be made without difficulty by a person skilled in the art.

In order to further increase the immunogenicity, the pharmaceutical composition according to the invention can additionally contain one or more auxiliary substances. A synergistic action of the nucleic acid molecule of either formula (I), (Ia), (II), (IIa), (IIIb), (IIIa) and/or (IIIb) according to the invention as defined above and of an auxiliary substance optionally additionally contained in the pharmaceutical composition (and, eventually, a pharmaceutically active component) as described above is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immunostimulating adjuvant according to the invention to be enhanced and/or influenced in a targeted manner. Particularly preferred auxiliary substances are cytokines, such as monokines, lymphokines, interleukins or chemokines, that promote the immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the pharmaceutical) compositions according to the invention are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The pharmaceutical composition according to the invention (first (without a pharmaceutically active component) and second (with a pharmaceutically active component) embodiment) can also additionally contain an adjuvant. Accordingly, the nucleic acid molecule of either formula (I), (Ia), (II), (IIa), (IIIb), (IIIa) and/or (IIIb) according to the invention as defined above as an immunostimulating agent or as an adjuvant (for the second embodiment of the inventive pharmaceutical composition), can be combined with further immunostimulating agents/adjuvants. Within the scope of the present invention, suitable agents/adjuvants for these purposes are in particular those compounds that enhance (by one or more mechanisms) the biological property/properties of the (modified or unmodified) nucleic acid molecule of either formula (I), (Ia), (II), (IIa), (IIIb), (IIIa) and/or (IIIb) according to the invention, that is to say in particular substances that potentiate the immunostimulating action of the nucleic acid molecule of either formula (I), (Ia), (II), (IIa), (IIIb), (IIIa) and/or (IIIb) according to the invention. Examples of agents/adjuvants which can be used according to the invention include, without implying any limitation, stabilizing cationic peptides or polypeptides as described above, such as protamine, nucleoline, spermine or spermidine, and cationic polysaccharides, in particular chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyldodecanoyl-amide hydroacetate); CALCITRIOL™ (1,25-dihydroxy-vitamin D3); calcium phosphate gel; CAPTM (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP(N-acetylglucosaminyl-(b1-4)-N-acetyl-muramyl-L-alanyl-D-isoglutamine); imiquimod (1-(2-methypropyl)-1H-imidazo[4,5-c]quinoline-4-amine); ImmTher™ (N-acetylglucosaminyl-N-acetyl muramyl-L-Ala-D-isoGlu-L-Ala-glycerol dipalmitate); DRVs (immunoliposomes prepared from dehydration-rehydration vesicles); interferon-gamma; interleukin-1 beta; interleukin-2; interleukin-7; interleukin-12; ISCOMS™ ("Immunostimulating Complexes"); ISCOPREP 7.0.3.™; liposomes; LOXORIBINE™ (7-allyl-8-oxoguanosine (guanine)); LT oral adjuvant (E. coli labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))ethylamide, monosodium salt); MURAMETIDE™ (Nac-Mur-L-Ala-D-Gln-OCH₃); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (beta-glucan); PLGA, PGA and PLA (homo- and co-polymers of lactic acid and glycolic acid; micro-/nano-spheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP); N-acetylmuramyl-L-threonyl-D-isoglutamine); Ty particles (Ty-VLPs or virus-like particles); Walter-Reed liposomes (liposomes containing lipid A adsorbed on aluminium hydroxide), and the like, etc. Lipopeptides, such as Pam3Cys, are likewise particularly suitable for combining with the inventive nucleic acid molecule of either formula (I), (Ia), (II), (IIa), (IIIb), (IIIa) and/or (IIIb) according to the invention as defined above, in the form of an immunostimulating adjuvant (see Deres et al., Nature 1989, 342: 561-564).

Adjuvants as mentioned above may be categorized into several classes, including adjuvants suitable for depot and delivery, for costimulation, adjuvants suitable as antagonists, etc. Preferred adjuvants suitable for depot and delivery may include e.g. aluminium salts such as Adju-phos, Alhydrogel, Rehydragel, etc., emulsions, such as CFA, SAF, IFA, MF59, Provax, TiterMax, Montanide, Vaxfectin, etc., copolymers, such as Optivax (CRL1005), L121, Poloaxmer4010), etc., liposomes, such as Stealth, etc., cochleates, such as BIORAL, etc., plant derived adjuvatns, such as QS21, Quil A, Iscomatrix, ISCOM, etc. Preferred adjuvants suitable for costimulation may include e.g. Tomatine, biopolymers, such as PLG, PMM, Inulin, etc., Microbe derived adjuvants, such as Romurtide, DETOX, MPL, CWS, Mannose, CpG7909, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP, etc. Preferred adjuvants suitable as antagonists may, e.g., include CGRP neuropeptide, etc.

Particularly preferred as adjuvants suitable for depot and delivery are cationic or polycationic compounds, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsl, FGF, Lactoferrin, Transportan, Buforin-2, Bac715-24, SynB, SynB(1), pVEC, hCT-derived peptides, SAP, protamine, spermine, spermidine, or histones. Additionally, preferred cationic or polycationic proteins or peptides may be selected from following proteins or peptides having the following total formula: $(Arg)_l$; $(Lys)_m$; $(His)_n$; $(Orn)_o$; $(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, H is or Orn; and x may be any number selected from 0, 1, 2, 3 or 4, provided, that the overall content of Xaa does not exceed 50% of all amino acids of the oligopeptide. Particularly preferred oligoarginines in this context are e.g. $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as adjuvant may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Blockpolymers consisting of a combination of one or more cationic blocks (e.g. selected og a cationic polymer as mentioned above) and of one or more hydrophilic- or hydrophobic blocks (e.g polyethyleneglycole); etc. Association or complexing the inventive nucleic acid molecule according to either formula (I), (Ia), (II), (IIa), (IIIb), (IIIa) and/or (IIIb) according to the invention as defined above with cationic or polycationic compounds preferably provides adjuvant properties to the nucleic acid and confers a stabilizing effect to the nucleic acid by complexation. The procedure for stabilizing the inventive nucleic acid is in general described in EP-A-1083232, the disclosure of which is incorporated by reference into the present invention in its entirety. Particularly preferred as cationic or polycationic compounds are compounds selected from the group consisting of protamine, nucleoline, spermin, spermidine, oligoarginines as defined above, such as $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc.

Adjuvants which may have a costimulating effect include nucleic acids of formula (IV): $G_lX_mG_n$, wherein: G is guanosine (guanine), uridine (uracil) or an analogue of guanosine (guanine) or uridine (uracil); X is guanosine (guanine), uridine (uracil), adenosine (adenine), thymidine (thymine), cytidine (cytosine) or an analogue of the above-mentioned nucleotides; l is an integer from 1 to 40, wherein when l=1 G is guanosine (guanine) or an analogue thereof, when l>1 at least 50% of the nucleotides are guanosine (guanine) or an analogue thereof; m is an integer and is at least 3; wherein when m=3 X is uridine (uracil) or an analogue thereof, when m>3 at least 3 successive uridines (uracils) or analogues of uridine (uracil) occur; n is an integer from 1 to 40, wherein when n=1 G is guanosine (guanine) or an analogue thereof, when n>1 at least 50% of the nucleotides are guanosine (guanine) or an analogue thereof;

or nucleic acids of formula (V): $C_lX_mC_n$, wherein: C is cytidine (cytosine), uridine (uracil) or an analogue of cytidine (cytosine) or uridine (uracil); X is guanosine (guanine), uridine (uracil), adenosine (adenine), thymidine (thymine), cytidine (cytosine) or an analogue of the above-mentioned nucleotides; l is an integer from 1 to 40, wherein when l=1 C is cytidine (cytosine) or an analogue thereof, when l>1 at least 50% of the nucleotides are cytidine (cytosine) or an analogue thereof; m is an integer and is at least 3; wherein when m=3 X is uridine (uracil) or an analogue thereof, when m>3 at least 3 successive uridines (uracils) or analogues of uridine (uracil) occur; n is an integer from 1 to 40, wherein when n=1 C is cytidine (cytosine) or an analogue thereof, when n>1 at least 50% of the nucleotides are cytidine (cytosine) or an analogue thereof.

Any compound, which is known to be immunostimulating due to its binding affinity (as ligands) to Toll-like receptors: TLR1, TLR2, TLR3, TLR4, TLR5, TLR6, TLR7, TLR8, TLR9, TLR10, TLR11, TLR12 or TLR13 may suitably be used as further component to further stimulate the immune response induced by nucleic acids of the invention in the inventive pharmaceutical compositions.

Another class of compounds, which may be added to a pharmaceutical composition of the invention, are CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytidine (cytosine)/guanine dinucleotide sequence(s) (CpG motif(s)). According to a first preferred alternative, at least one CpG motif contained in these sequences, that is to say the C (cytidine (cytosine)) and the G (guanine) of the CpG motif, is unmethylated. All further cytidines (cytosines) or guanines optionally contained in these sequences can be either methylated or unmethylated. According to a further preferred alternative, however, the C (cytidine (cytosine)) and the G (guanine) of the CpG motif can also be present in methylated form.

According to a particularly preferred embodiment, the pharmaceutical composition according to the invention can also be provided as a vaccine. Vaccines according to the invention typically comprise (correspond to) a pharmaceutical composition according to the invention. The composition of such vaccines according to the invention is characterized by a specific class of pharmaceutically active components incorporated into the vaccine composition. Typically, the pharmaceutically active compound will be an immunstimulatory substance, which evokes a specific (adaptive) immune response against a certain antigen/s. The specific (adaptive) immune response elicited allows the subject to develop an immune response (evoked by an active or passive mode) against e.g. a specific pathogen or a specific tumor.

The inventive pharmaceutical composition and, in particular the inventive vaccine, is specifically characterized by the manner in which it is administered. Typically, pharmaceutical compositions of the invention, in particular vaccines, are preferably administered systemically. Routes for the administration of such an inventive pharmaceutical composition/vaccine typically include oral, subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual topical and/or intranasal routes. Alternatively, vaccines or pharmaceutical composition of the invention may be administered by an intradermal, subcutaneous, intramuscular route. Compositions/vaccines are therefore formulated preferably in liquid or solid form as defined above for pharmaceutical compositions in general. Further auxiliary substances (as defined above) can further increase the immunogenicity, in particular of the vaccine, which may preferably be incorporated into a vaccine according to the invention. Advantageously, one or more such auxiliary substances as defined hereinbefore is/are to be chosen, depending on the immunogenicity and other properties of the pharmaceutically active component in the vaccine according to the invention.

According to a further preferred object of the present invention, the pharmaceutical composition according to the invention, particularly preferably the inventive vaccine, are used for the treatment of indications mentioned by way of example hereinbelow. With a pharmaceutical composition according to the invention, particularly preferably an inventive vaccine, it is possible to treat, for example, diseases or conditions that are associated with various pathologically absent immune responses or that require an immune response, preferably an increased immune response, within the context of a therapy, for example tumour-specific or pathogen-specific diseases, infectious diseases, etc or diseases, which may be treated by shifting the (exceeding) immune response to a TH1 dominated immune response and/or by desensitizing the patient suffering from an exceeding immune response, as e.g. in allergies or autoimmune diseases. The production of such an immune response, or the increase of an already existing but optionally inadequate immune response, by the pharmaceutical composition according to the invention is based substantially on its ability to trigger an a non-antigen-specific immune reaction. An important factor for a suitable immune response is the stimulation of different T-cell sub-populations. T-lymphocytes typically differentiate into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of the B-cells for conversion into plasma cells and by formation of antibodies (e.g. against antigens). The Th1/Th2 ratio is therefore of great importance in the immune response. In connection with the present invention, the Th1/Th2 ratio of the immune response is preferably displaced by the pharmaceutical composition according to the invention containing at least one nucleic acid molecule of either formula (I), (Ia), (II), (IIa), (IIIb), (IIIa) and/or (IIIb) according to the invention as defined above, e.g. one, two three, four six seven, or more nucleic acids thereof, in the direction towards the cellular response, that is to say the Th1 response, and a predominantly cellular immune response is thereby induced. Only by this displacement and the preferential, or even exclusive, occurrence of a TH1 immune response an efficient treatment of the above-mentioned indications is possible. Preferably, therefore, the present pharmaceutical compositions or vaccines according to the invention are used to trigger tumour-specific or pathogen-specific immune responses. Such pharmaceutical compositions or vaccines according to the invention can be used particularly preferably for increasing immune responses of antigen-presenting cells (APCs). Likewise particularly preferably, the pharmaceutical compositions or vaccines according to the invention can be used for the treatment of cancer or tumour diseases, preferably selected from colon carcinomas, melanomas, renal carcinomas, lymphomas, acute myeloid leukaemia (AML), acute lymphoid leukaemia (ALL), chronic myeloid leukaemia (CML), chronic lymphocytic leukaemia (CLL), gastrointestinal tumours, pulmonary carcinomas, gliomas, thyroid tumours, mammary carcinomas, prostate tumours, hepatomas, various virus-induced tumours such as, for example, papilloma virus-induced carcinomas (e.g. cervical carcinoma), adenocarcinomas, herpes virus-induced tumours (e.g. Burkitt's lymphoma, EBV-induced B-cell lymphoma), heptatitis B-induced tumours (hepatocell carcinoma), HTLV-1- and HTLV-2-induced lymphomas, acoustic neuromas/neurinomas, cervical cancer, lung cancer, pharyngeal cancer, anal carcinomas, glioblastomas, lymphomas, rectal carcinomas, astrocytomas, brain tumours, stomach cancer, retinoblastomas, basaliomas, brain metastases, medulloblastomas, vaginal cancer, pancreatic cancer, testicular cancer, melanomas, thyroidal carcinomas, bladder cancer, Hodgkin's syndrome, meningiomas, Schneeberger disease, bronchial carcinomas, hypophysis tumour, Mycosis fungoides, oesophageal cancer, breast cancer, carcinoids, neurinomas, spinaliomas, Burkitt's lymphomas, laryngeal cancer, renal cancer, thymomas, corpus carcinomas, bone cancer, non-Hodgkin's lymphomas, urethral cancer, CUP syndrome, head/neck tumours, oligodendrogliomas, vulval cancer, intestinal cancer, colon carcinomas, oesophageal carcinomas, wart involvement, tumours of the small intestine, craniopharyngeomas, ovarian carcinomas, soft tissue tumours/sarcomas, ovarian cancer, liver cancer, pancreatic carcinomas, cervical carcinomas, endometrial carcinomas, liver metastases, penile cancer, tongue cancer, gall bladder cancer, leukaemia, plasmocytomas, uterine cancer, lid tumour, prostate cancer, etc. It is particularly preferred, if the lipid used in the lipid-modified nucleic acid or as pharmaceutically active component in the composition is alpha-tocopherol (vitamin E), D-alpha-tocopherol, L-alpha-tocopherol, D,L-alpha-tocopherol or vitamin E succinate (VES). alpha-Tocopherol (vitamin E) is not very toxic and exhibits potent anti-tumour activity (A. Bendich, L. J. Machlin *Am. J. Clin. Nutr.* 48 (1988) 612), which makes it appear very promising in cancer therapy. As an explanation for the inhibition of the proliferation of tumour cells or the cytotoxic activity thereon, two mechanisms inter alia are known: On the one hand, vitamin E is a potent antioxidant and a good radical acceptor (C. Borek *Ann. NY Acad. Sci.* 570 (1990) 417); on the other hand, it is able, by stimulating the immune response, to prevent tumour growth (G. Shklar, J. Schwartz, D. P. Trickier, S. Reid *J. Oral Pathol. Med.* 19 (1990) 60). In more recent works, a connection has further been found between the expression of the tumour suppressor gene p53 in tumour cells (oral squamous cancer) and treatment with vitamin E succinate (VES) (J. Schwartz, G. Shklar, D. Trickier *Oral Oncol. Europ. J. Cancer* 29B (1993) 313). It has thereby been possible to observe both a stimulation of the production of wild-type p53, which acts as a tumour suppressor, and a reduction in mutated p53, which develops oncogenic activity. Interestingly, the biological activity of VES on these tumour cells is dose-dependent in two respects: in physiological doses (0.001 to 50 µmol/l), increasing cell growth is to be observed; in pharmacological doses (100 to 154 µmol/l), cell growth is inhibited. This has been shown in cell culture (T. M. A. Elattar, A. S. Virji *Anticancer Res.* 19 (1999) 365). It has also been possible to induce apoptosis in various breast cancer cell lines by treatment with VES (W. Yu, K. Israel, Q. Y. Liao, C. M. Aldaz, B. G. Sanders, K. Kline Cancer Res. 59 (1999) 953). The induced apoptosis is initiated via an interaction of Fas ligand and Fas receptor. This is to be particularly emphasised because it has hitherto not been possible to observe such a mechanism in the corresponding cell lines. There are various isomers of vitamin E, which differ in the number and position of the methyl groups on the aromatic ring. In the described works, the biologically most active form of naturally occurring vitamin E, α-tocopherol, was used. This in turn occurs in various stereoisomers, because the molecule contains three optically active centres. The natural form of vitamin E is RRR-alpha-tocopherol (formerly D-alpha-tocopherol), but the racemate (D,L-alpha-tocopherol) is predominantly used nowadays. All the above-mentioned forms of vitamin E are likewise included as lipid within the scope of the present invention.

Likewise particularly preferably, at least one nucleic acid molecule of either formula (I), (Ia), (II), (IIa), (IIIb), (IIIa) and/or (IIIb) according to the invention as defined above, or the pharmaceutical composition according to the invention, are used for the treatment of infectious diseases. Without implying any limitation, such infectious diseases are preferably selected from influenza, malaria, SARS, yellow fever, AIDS, Lyme borreliosis, Leishmaniasis, anthrax, meningitis, viral infectious diseases such as AIDS, Condyloma acuminata, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, measles, foot-and-mouth disease, mononucleosis, mumps, Norwalk virus infection, Pfeiffer's glandular fever, smallpox, polio (childhood lameness), pseudo-croup, fifth disease, rabies, warts, West Nile fever, chickenpox, cytomegalic virus (CMV), from bacterial infectious diseases such as miscarriage (prostate inflammation), anthrax, appendicitis, borreliosis, botulism, Camphylobacter, *Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella paratyphus, Salmonella typhus*, scarlet fever, syphilis, tetanus, tripper, tsutsugamushi disease, tuberculosis, typhus, vaginitis (colpitis), soft chancre, and from infectious diseases caused by parasites, protozoa or fungi, such as amoebiasis, bilharziosis, Chagas disease, athlete's foot, yeast fungus spots, scabies, malaria, onchocercosis (river blindness), or fungal diseases, toxoplasmosis, trichomoniasis, trypanosomiasis (sleeping sickness), visceral Leishmaniosis, nappy/diaper dermatitis, schistosomiasis, fish poisoning (Ciguatera), candidosis, cutaneous Leishmaniosis, lambliasis (giardiasis), or sleeping sickness, or from infectious diseases caused by *Echinococcus*, fish tapeworm, fox tapeworm, canine tapeworm, lice, bovine tapeworm, porcine tapeworm, miniature tapeworm.

Accordingly, at least one nucleic acid of the invention of either formula (I), (Ia), (II), (IIa), (IIIb), (IIIa) and/or (IIIb) according to the invention as defined above, or the pharmaceutical composition of the invention may be used for the preparation of a medicament for the treatment of an allergic disorder or disease. Allergy is a condition that typically involves an abnormal, acquired immunological hypersensitivity to certain foreign antigens or allergens. Allergies normally result in a local or systemic inflammatory response to these antigens or allergens and leading to immunity in the body against these allergens. Allergens in this context include e.g. grasses, pollens, molds, drugs, or numerous environmental triggers, etc. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, allergic asthma (leading to swelling of the nasal mucosa), allergic conjunctivitis (leading to redness and itching of the conjunctiva), allergic rhinitis ("hay fever"), anaphylaxis, angiodema, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. With regard to the present invention, e.g. an inventive pharmaceutical composition or vaccine is provided, which contains an allergen (e.g. from a cat allergen, a dust allergen, a mite antigen, a plant antigen (e.g. a birch antigen) etc.) either as a protein, an mRNA (or DNA) encoding for that protein allergen in combination with a nucleic acid of the invention of either formula (I), (Ia), (II), (IIa), (IIIb), (IIIa) and/or (IIIb) according to the invention as defined above. A pharmaceutical composition of the present invention may shift the (exceeding) immune response to a stronger TH1 response, thereby suppressing or attenuating the undesired IgE response.

Likewise, at least one nucleic acid of the invention of either formula (I), (Ia), (II), (IIa), (IIIb), (IIIa) and/or (IIIb) according to the invention as defined above, or the pharmaceutically active composition of the invention may be used for the preparation of a medicament for the treatment of autoimmune diseases. Autoimmune diseases can be broadly divided into systemic and organ-specific or localised autoimmune disorders, depending on the principal clinico-pathologic features of each disease. Autoimmune disease may be divided into the categories of systemic syndromes, including SLE, Sjögren's syndrome, Scleroderma, Rheumatoid Arthritis and polymyositis or local syndromes which may be endocrinologic (DM Type 1, Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus), systemic lupus erythematosus (SLE), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), psoriasis, Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T-Cell Bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to one subunit of T-cell receptors in a non-specific fashion. Another explanation deduces autoimmune diseases from a molecular mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of rheumatic fever. The present invention allows therefore provision of a pharmaceutical composition containing an autoantigen (as protein, mRNA or DNA encoding for a autoantigen protein) and a nucleic acid of the invention which typically allows the immune system to be desensitized.

The invention relates also to the use of at least one inventive nucleic acid molecule of either formula (I), (Ia), (II), (IIa), (IIIb), (IIIa) and/or (IIIb) according to the invention as defined above in the preparation of a pharmaceutical composition according to the invention or of a vaccine according to the invention for the treatment of indications described hereinbefore, for example for the treatment of the mentioned tumour, autoimmune diseases, allergies and infectious diseases. Alternatively, the invention includes the (therapeutic) use of at least one nucleic acid molecule of either formula (I), (Ia), (II), (IIa), (IIIb), (IIIa) and/or (IIIb) according to the invention as defined above, for the treatment of tumour or infectious diseases, as described hereinbefore.

Likewise included in the present invention are kits, e.g. kit of parts, (each part) containing at least one nucleic acid molecule of either formula (I), (Ia), (II), (IIa), (IIIb), (IIIa) and/or (IIIb) according to the invention, and/or a pharmaceutical composition according to the invention and/or a vaccine according to the invention as well as, optionally, technical instructions for use with information on the administration and dosage of the at least one nucleic acid molecule of either formula (I), (Ia), (II), (IIa), (IIIb), (IIIa) and/or (IIIb) according to the invention as defined above, and/or of the pharmaceutical composition according to the invention and/or of the vaccine according to the invention.

Methods of treating a disorder or disease selected from the group consisting of cancer diseases, infectious diseases, autoimmune diseases and allergies by administering to a patient in need thereof a pharmaceutically effective amount of a nucleic acid molecule according to the invention.

FIGURES

The following Figures are intended to illustrate the invention further. They are not intended to limit the subject matter of the invention thereto.

FIG. 1: shows the TNFα inducing capacity of DOTAP formulated RNAs according to formula (I). PBMCs were seeded at a density of $2*10^5$/well/200 µl Medium and stimulated with RNA (4 µg/ml) formulated with DOTAP (12 µg/ml) for 20 h. A TNFα-ELISA was then performed with cell free supernatants. As can be seen in FIG. 1, secretion of TNFα is significantly induced by the inventive nucleic acids according to formula (I), particularly by mRNA sequences according to SEQ ID NOs: 114 to 119 inventive nucleic acids according to formula (I) as defined above, i.e. mRNA sequences according to SEQ ID NOs: 114 to 119 (SEQ ID NO: 114 (R820/(N100)$_2$), SEQ ID NO: 115 (R719/(N100)$_5$), SEQ ID NO: 116 (R720/(N100)$_{10}$), SEQ ID NO: 117 (R821/(N40T20N40)$_2$), SEQ ID NO: 118 (R722/(N40T20N40)$_5$), and SEQ ID NO: 119 (R723/(N40T20N40)$_{10}$)) and controls $G_2U_{20}G_2$ (GGUUUUUUUUUUUUUUUUUUUUGG) (SEQ. ID NO: 125), Seq. $U_{21}$: UUUUUUUUUUUUUUUUUUUUU (SEQ ID NO: 126) (Phosphodiester) and Poly(U) (Sigma, 800-1000 kDa).

Figure 2:
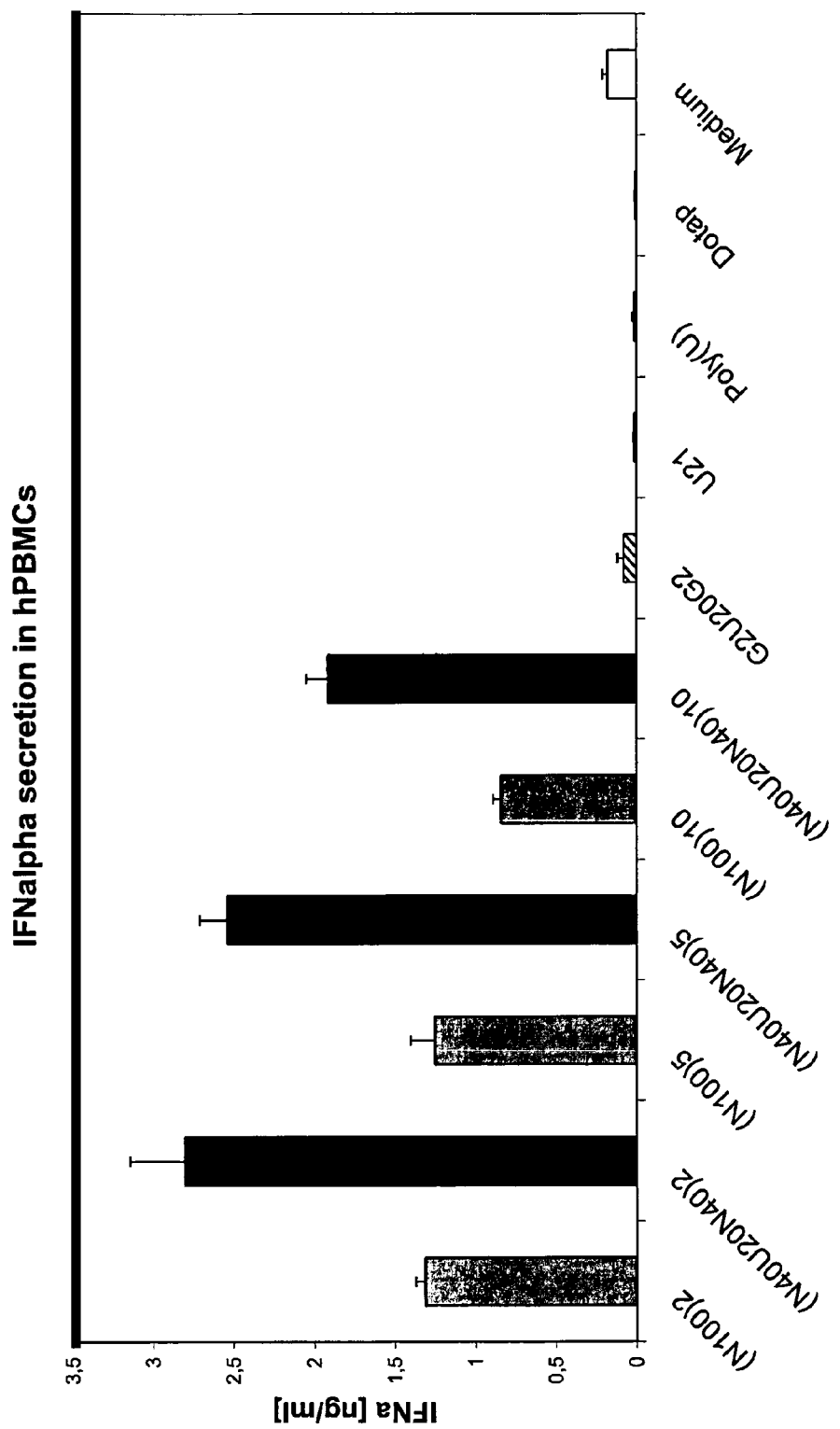

FIG. 2: shows the IFNα inducing capacity of DOTAP formulated RNAs according to formula (I). PBMCs were seeded at a density of $2*10^5$/well/200 µl Medium and stimulated with RNA (2 µg/ml) formulated with DOTAP (12 µg/ml) for 20 h. An IFNα-ELISA was then performed with cell free supernatants. As can be seen in FIG. 2, secretion of IFNα is significantly induced by the inventive nucleic acids according to formula (I), particularly by mRNA sequences according to SEQ ID NOs: 114 to 119 inventive nucleic acids according to formula (I) as defined above, i.e. mRNA sequences according to SEQ ID NOs: 114 to 119 (SEQ ID NO: 114 (R820/(N100)$_2$), SEQ ID NO: 115 (R719/(N100)$_5$), SEQ ID NO: 116 (R720/(N100)$_{10}$), SEQ ID NO: 117 (R821/(N40T20N40)$_2$), SEQ ID NO: 118 (R722/(N40T20N40)$_5$), and SEQ ID NO: 119 (R723/(N40T20N40)$_{10}$)) and controls $G_2U_{20}G_2$ (GGUUUUUUUUUUUUUUUUUUUUGG) (SEQ. ID NO: 125), Seq. $U_{21}$: UUUUUUUUUUUUUUUUUUUUU (SEQ ID NO: 126) (Phosphodiester) and Poly(U) (Sigma, 800-1000 kDa).

EXAMPLES

The following Examples are intended to illustrate the invention further. They are not intended to limit the subject matter of the invention thereto.

1. Synthesis of Exemplary Nucleic Acids of Either Formula (I), (Ia), (II), (IIa), (IIIb), (IIIa) and/or (IIIb) According to the Invention RNA oligonucleotides, as examples of the nucleic acid of the general formula (I), (Ia), (II), (IIa), (IIIb), (IIIa) and/or (IIIb) according to the invention, were prepared by automatic solid-phase synthesis by means of phosphoramidite chemistry (including sequences according to SEQ ID NOs: 84-85 (formula (I)), SEQ ID NOs: 86-87 (formula (Ia)), SEQ ID NOs: 88-94 (formulas (II), (IIa) and (IIIb)), and SEQ ID NOs: 107-108 (formulas (IIIa) and (IIIb))). In each case the RNA-specific 2'-hydroxyl groups of the nucleotides were protected with TBDMS protecting groups. In the synthesis of phosphorothioates, Beaucage reagent was used for the oxidation. The cleavage of carrier material and of the base-labile protecting groups was carried out with methylamine, and the cleavage of the TBDMS protecting group was effected with triethylamine hydrofluoride.

The crude product was purified by means of HPLC either by ion-pair chromatography, by ion-exchange chromatography or by a combination of the two methods, desalinated and dried. The product was checked for purity and correct base composition by mass spectrometry.

According to an alternative way, the above sequences were prepared by in vitro translation based on DNA vectors or oligonucleotide sequences carrying the inventive sequences.

2. In vitro Immunostimulation with Exemplary Nucleic Acids of Either Formula (I), (Ia), (II). (IIa), (IIIb), (IIIa) and/or (IIIb) according to the invention a) For the stimulation of mouse BDMCs (bone marrow derived dendritic cells), 3 µl of oligofectamine were mixed with 30 µl of FCS-free IMDM medium (BioWhittaker, catalogue no. BE12-722F) and incubated at room temperature for 5 minutes. 6 µg of a nucleic acid according to SEQ ID NOs: 84-94 and 107-108 (each type of nucleic acid forming a single experiment), respectively, in the form of RNA, was mixed with 60 µl of FCS-free IMDM and mixed with oligofectamine/IMDM, and incubated for 20 minutes at room temperature. 33 µl of this mixture were then placed for cultivation overnight in a well of a 96-well microtitre culture plate which contained 200,000 mouse BDMCs in 200 µl of FCS-free IMDM medium. After 4 hours, 100 µl of IMDM containing 20% FCS were added and, after 16 hours' co-incubation, the supernatant was removed and tested for interleukin-6 (IL-6) and interleukin-12 (IL-12) by a cytokine ELISA. Comparison tests were carried out analogously to the above sequences using the immuno-stimulating uncapped wild-type mRNA of beta-galactosidase (lacZ), complexed with protamine.

It was possible to show that the nucleic acids of formulas (I), (Ia), (II), (IIa), (IIIb), (IIIa) and/or (IIIb) according to the invention, present in the form of RNA, in particular the sequences according to the invention of SEQ ID NOs: 84-94 and 107-108, have good immunostimulating properties for stimulation of an innate immune response.

b) Human PBMCs were obtained via a Ficoll density gradient and cultivation overnight in X-VIVO-15 medium (BioWhittaker, catalogue no. BE04-418Q), which contained 1% glutamine and 1% penicillin in the presence of 10 µg/ml of the nucleic acids of either formula (I), (Ia), (II), (IIa), (IIIb), (IIIa) and/or (IIIb) according to the invention in the form of RNA, in particular of the sequences according to the invention of SEQ ID NOs: 84-94 and 107-108 (each type of nucleic acid forming a single experiment).

For stimulation, 3 µl of oligofectamine were mixed with 30 µl of X-VIVO-15 medium (BioWhittaker, catalogue no. BE04-418Q) and incubated at room temperature for 5 minutes. 6 µg of the nucleic acids of either formula (I), (Ia), (II), (IIa), (IIb), (IIIa) and/or (IIIb) according to the invention in the form of RNA, in particular the sequences according to the invention SEQ ID NOs: 84-94 and 107-108 (each type of nucleic acid in a single experiment), respectively, were mixed with 60 µl of X-VIVO-15 medium (Bio-Whittaker, catalogue no. BE04-418Q) and, mixed with oligofectamine/X-VIVO medium, incubated for 20 minutes at room temperature. 33 µl of this mixture were then placed for cultivation overnight in a well of a 96-well microtitre culture plate which contained 200,000 PBMCs in 200 µl of X-VIVO-15 medium (BioWhittaker, catalogue no. BE04-418Q). After co-incubation for 16 hours, the supernatant was removed and tested for interleukin-6 (IL-6) and interleukin-12 (IL-12) and TNFα by means of a cytokine-ELISA. Comparison tests were carried out analogously to the sequences according to the invention (see above) with the immunostimulating oligo RNA40 (5'-GCCCGU-CUGUUGUGUGACUC-3', SEQ ID NO: 113).

It was possible to show that the inventive nucleic acids in the form of RNA, in particular having the sequences according to the invention either formula (I), (Ia), (II), (IIa), (IIIb), (IIIa) and/or (IIIb) according to the invention as defined above have good immunostimulating properties.

3. In Vivo Immunostimulation with Exemplary Nucleic Acids of Either Formula (I), (Ia), (II), (IIa), (IIIb), (IIIa) and/or (IIIb) According to the Invention—use as Adjuvant BALB/c mice (5 per group) were injected with beta-galactosidase protein and with an adjuvant (as defined herein) on days 0 and 10. The mice were sacrificed on day 20 and the blood serum was used for an antibody test against beta-galactosidase protein by means of ELISA, and the IL-6, IL-12 and TNF-alpha values were determined analogously to the above-described in vitro cultures.

4. Stimulation of Human Cells with an Adjuvant According to the Invention in the Form of a Nucleic Acid Molecule of Either Formula (I), (Ia), (II), (IIa), (IIIb), (IIIa) and/or (IIIb)

a) In order to determine the immunogenic activity of nucleic acids of either formula (I), (Ia), (II), (IIa), (IIIb), (IIIa) and/or (IIIb) according to the invention as defined above in the form of adjuvants, particularly of nucleic acids containing a sequence according to SEQ ID NOs: 84-94 and 107-108 (each type of nucleic acid again forming a single experiment) were co-incubated with human cells. To this end, human PBMC cells, for example, were co-incubated for 16 hours in X-VIVO-15 medium (BioWhittaker, catalogue no. BE04-418Q), enriched with 2 mM L-glutamine (BioWhittaker), 10 U/ml penicillin (BioWhittaker) and 10 µg/ml streptomycin, with 10 µg/ml of RNA (mRNA coding for (3-galactosidase and optionally with 10 µg/ml protamine. The supernatants were removed and the release of IL-6 and TNFalpha was analysed by means of ELISA.

b) In a further experiment, the release of TNF-alpha by human PBMC cells was determined after stimulation with inventive nucleic acids of either formula (I), (Ia), (II), (IIa), (IIIb), (IIIa) and/or (IIIb) according to the invention (SEQ ID NOs: 84-94 and 107-108, each type of nucleic acid in a single experiment, see above) and also adjuvants used according to the invention.

To that end, human PBMC cells were co-incubated for 16 hours with 10 µg/ml said inventive nucleic acids in X-VIVO 15 medium (BioWhittaker), enriched with 2 mM L-glutamine (BioWhittaker), 10 U/ml penicillin (BioWhittaker) and 10 U/ml streptomycin. The supernatants were removed and analysed by means of ELISA.

5. Secretion of TNFα and IFN-α in Human PBMCs

For this experiments, several inventive nucleic acids according to formula (I) as defined above, i.e. mRNA sequences according to SEQ ID NOs: 114 to 119, were formulated with DOTAP (Roche).

The inventive nucleic acid sequences used in the experiment were

SEQ ID NO: 114 (R820/(N100)$_2$);
SEQ ID NO: 115 (R719/(N100)$_5$);
SEQ ID NO: 116 (R720/(N100)$_{10}$);
SEQ ID NO: 117 (R821/(N40T20N40)$_2$);
SEQ ID NO: 118 (R722/(N40T20N40)$_5$); and
SEQ ID NO: 119 (R723/(N40T20N40)$_{10}$.

Human PBMCs were then stimulated with the formulated RNAs at a concentration of 8 µg/ml and 12 µg/ml DOTAP for 20 hours. The Supernatants were then investigated for the secretion of TNFa and IFN-a using a matched-paired ELISA.

For the experiment, human PBMCs were obtained via a Ficoll density gradient and cultivation for 20 hours in X-VIVO-15 medium (BioWhittaker, catalogue no. BE04-418Q), which contained 1% glutamine and 1% penicillin in the presence of 2 or 4 µg/ml of the above nucleic acids for IFNα or TNFα stimulation respectively. For formulation and stimulation, 3 or 6 µg RNA in HBS buffer were transferred to a vial containing 18 µg N-[1-(2,3-Dioleoyloxy)propyl]-N,N,Ntrimethylammonium methylsulfate (DOTAP) (Roche Diagnostics, catalogue no. 11 811 177 001) in HBS buffer and carefully mixed by gently pipetting the mixture several times. The transfection mixture was incubated for 15 min at 15-25° C. 1 volume of the DOTAP/nucleic acid mixture was then gently diluted with 7.3 volumes of X-Vivo medium. 100 μl of this mixture were then placed for cultivation overnight in a well of a 96-well microtitre culture plate which contained 2*10⁵ PBMCs in 100 μl of X-VIVO-15 medium (BioWhittaker, catalogue no. BE04-418Q). After coincubation for 20 hours, the supernatant was removed and tested for IFNα and TNFα by means of a cytokine-ELISA. Comparison tests were carried out analogously to the sequences according to the invention (see above) with the immunostimulating oligo $G_2U_{20}G_2$ (Phosphothioat-modified), Poly(U) (Sigma, Taufkirchen, Germany) and the oligo $U_{21}$ (Phophodiester).

The results are shown in FIGS. 1 and 2. FIG. 1 shows the TNFα inducing capacity of DOTAP formulated RNAs. PBMCs were seeded at a density of 2*10⁵/well/200 μl Medium and stimulated with RNA (4 μg/ml) formulated with DOTAP (12 μg/ml) for 20 h. A TNFα-ELISA was then performed with cell free supernatants. FIG. 2 shows the IFNα inducing capacity of DOTAP formulated RNAs. PBMCs were seeded at a density of 2*10⁵/well/ 200 μl Medium and stimulated with RNA (2 μg/ml) formulated with DOTAP (12 μg/ml) for 20 h. An IFNα-ELISA was then performed with cell free supernatants. As can be seen in FIG. 1 and FIG. 2, both secretion of TNFα and IFNα is significantly induced by the inventive nucleic acids according to formula (I), particularly by mRNA sequences according to SEQ ID NOs: 114 to 119 inventive nucleic acids according to formula (I) as defined above, i.e. mRNA sequences according to SEQ ID NOs: 114 to 119 (SEQ ID NO: 114 (R820/(N100)₂), SEQ ID NO: 115 (R719/(N100)₅), SEQ ID NO: 116 (R720/(N100)₁₀), SEQ ID NO: 117 (R821/ (N40T20N40)₂), SEQ ID NO: 118 (R722/ (N40T20N40)₅), and SEQ ID NO: 119 (R723/ (N40T20N40)₇₀)) versus control sequences $G_2U_{20}G_2$ (Phosphothioat-modified), Poly(U) (Sigma, Taufkirchen, Germany) and the oligo $U_{21}$ (Phophodiester).

ADVANTAGES OF THE INVENTION

A nucleic acid of the general formula (I), (Ia), (II), (IIa), (IIIb), (IIIa) and/or (IIIb) according to the invention may be used as immunostimulating agent as such for stimulating the innate immune system of a patient to be treated. This immunostimulating property may well be enhanced by the addition of other compounds known in the art as actively stimulating the innate immune response to the inventive nucleic acids, e.g. by lipid modification or addition of additional adjuvants. The inventive nucleic acids as defined herein, particularly those according to formula (I) comprising the structure $(N_uG_lX_mG_nN_v)_a$, or of derivatives thereof, exhibit a significant better amplification in bacteria, e.g. *E. coli*. It is furthermore particularly advantageous, if the inventive nucleic acid $(N_vG_lX_mG_nN_u)_a$, of formula (I), or of derivatives thereof, is a partially double-stranded nucleic acid molecule or a mixture of a single-stranded and a double-stranded nucleic acid molecule, since such a (partially double-stranded) inventive nucleic acid molecule according to formula (I) (or of formula (Ia), (II) (IIa), (IIIb), (IIIa) and/or (IIIb)), can positively stimulate the innate immune response in a patient to be treated by addressing the PAMP-(pathogen associated molecular pattern) receptors for single-stranded RNA (TLR-7 and TLR-8) as well as the PAMP-receptors for double-stranded RNA (TLR-3, RIG-I and MDA-5). Receptors TLR-3, TLR-7 and TLR-8 are located in the endosome and are activated by RNA taken up by the endosome. In contrast, RIG-I and MDA-5 are cytoplasmic receptors, which are activated by RNA which was directly taken up into the cytoplasm or which has been released from the endosomes (endosomal release or endosomal escape). Accordingly, a partially double-stranded inventive nucleic acid $(N_uG_lX_mG_nN_v)_a$ of formula (I) (or of derivatives thereof, e.g. (a partially double-stranded) inventive nucleic acid molecule according to formula (Ia), (II) (IIa), (IIIb), (IIIa) and (IIIb) as defined herein)) is capable of activating different signal cascades of immunostimulation and thus leads to an increased innate immune response or enhances such a response significantly. A further advantage of the invention is the high induction of the antiviral cytokine IFNalpha which is preferred in stimulation of the innate immune system. An often underestimated limitation of generally accepted immunostimulating nucleic acids (e.g. poly A:U and poly I:C) is the undefined structure of them which results in regulatory restrictions.

The invention claimed is:

1. An isolated nucleic acid molecule comprising the nucleoside sequence of any one of SEQ ID NOs: 114-119 or the DNA coding sequence thereof, provided that: the guanosine (guanine), the uridine (uracil), the adenosine (adenine), the thymidine (thymine), or the cytidine (cytosine) positions of the nucleotide (nucleoside) sequence of the nucleic acid may be substituted with an analogue of nucleotides (nucleosides) selected from 1-methyl-adenosine (adenine), 2-methyl-adenosine (adenine), 2-methylthio-N6-isopentenyl-adenosine (adenine), N6-methyl-adenosine (adenine), N6-isopentenyl-adenosine (adenine), 2-thio-cytidine (cytosine), 3-methyl-cytidine (cytosine), 4-acetyl-cytidine (cytosine), 2,6-diaminopurine, 1-methyl-guanosine (guanine), 2-methyl-guanosine (guanine), 2,2-dimethyl-guanosine (guanine), 7-methyl-guanosine (guanine), inosine, 1-methyl-inosine, dihydro-uridine (uracil), 4-thio-uridine (uracil), 5-carboxymethylaminomethyl-2-thio-uridine (uracil), 5-(carboxyhydroxylmethyl)-uridine (uracil), 5-fluoro-uridine (uracil), 5-bromo-uridine (uracil), 5-carboxymethylaminomethyl-uridine (uracil), 5-methyl-2-thio-uridine (uracil), N-uridine (uracil)-5-oxyacetic acid methyl ester, 5-methylaminomethyl-uridine (uracil), 5-methoxyaminomethyl-2-thio-uridine (uracil), 5'-methoxycarbonylmethyl-uridine (uracil), 5-methoxy-uridine (uracil), uridine (uracil)-5-oxyacetic acid methyl ester, uridine (uracil)-5-oxyacetic acid (v), queosine, beta-D-mannosyl-queosine, wybutoxosine, and inosine; 2phosphate moieties may be substituted with phosphoramidates, phosphorothioates, peptide nucleotides, or methylphosphonates; and ribose components may be substituted with deoxyribose.

2. The nucleic acid according to claim 1, wherein the nucleic acid molecule comprises the sequence of SEQ ID NO: 114.

3. The nucleic acid according to claim 1, wherein the nucleic acid molecule comprises the sequence of SEQ ID NO: 115.

4. The nucleic acid according to claim 1, wherein the nucleic acid molecule comprises the sequence of SEQ ID NO: 116.

5. The nucleic acid according to claim 1, wherein the nucleic acid molecule comprises the sequence of SEQ ID NO: 117.

6. The nucleic acid according to claim 1, wherein the nucleic acid molecule comprises the sequence of SEQ ID NO: 118.

7. The nucleic acid according to claim 1, wherein the nucleic acid molecule comprises the sequence of SEQ ID NO: 119.

8. The nucleic acid according to claim 1, wherein the nucleic acid molecule is single-stranded.

9. The nucleic acid according to claim 1, wherein the nucleic acid molecule is double-stranded or partially double-stranded.

10. The nucleic acid according to claim 1, wherein the nucleic acid molecule is linear.

11. The nucleic acid according to claim 1, wherein the nucleic acid molecule is circular.

12. The nucleic acid according to claim 1, wherein the nucleic acid molecule is RNA.

13. The nucleic acid according to claim 1, wherein the nucleic acid is prepared by in vitro transcription.

14. An immunostimulating agent comprising the nucleic acid molecule of claim 1.

15. A pharmaceutical composition comprising the nucleic acid molecule according to claim 1 and a pharmaceutically acceptable carrier.

16. The pharmaceutical composition according to claim 15, further comprising at least one pharmaceutically active component.

17. The pharmaceutical composition according to claim 16, wherein the at least one pharmaceutically active component is selected from the group consisting of peptides, proteins, nucleic acids, low molecular weight organic compounds having a molecular weight less than 5000, low molecular weight inorganic compounds having a molecular weight less than 5000, sugars, antigens, antibodies, pathogens, attenuated pathogens, de-activated pathogens, cells, cellular fragments, cellular fractions and therapeutic agents.

18. The pharmaceutical composition according to claim 16, comprising a peptide antigen or a polypeptide antigen.

19. The pharmaceutical composition according to claim 15, further comprising at least one adjuvant.

20. The pharmaceutical composition according to claim 19, wherein the adjuvant is selected from the group consisting of cationic peptides; protamine; nucleoline; spermine; spermidine; cationic polysaccharides; chitosan; TDM (trehalose dimycolate); MDP (muramyl dipeptide); pluronics; alum solution; aluminium hydroxide; ADJUMER™ (polyphosphazene); aluminium phosphate gel; glucans from algae; algammulin; aluminium hydroxide gel (alum); highly protein adsorbing aluminium hydroxide gel; low viscosity aluminium hydroxide gel; SPT (emulsion of squalane (5%); Tween 80; Pluronic L121; phosphate buffered saline); AVRIDINE™ (propanediamine); BAY R1005™ (N-(2-deoxy-2-L-leucylamino-b-D-glucopyranosyl)-N-octadecyldodecanoyl-amide hydroacetate); CALCITRIOL™ (1-alpha,25-dihydroxy-vitamin D3); calcium phosphate gel; CAPTM (calcium phosphate nanoparticles); cholera holotoxin; cholera-toxin-A1-protein-A-D-fragment fusion protein; subunit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-Dglutamine (GMDP), ii) dimethyldioctadecylammonium chloride (DDA), iii) zinc-Lproline salt complex (ZnPro-8); GM-CSF); GMDP (N-acetylglucosaminyl-(b1-4)-Nacetylmuramyl-L-alanyl-D-isoglutamine); imiquimod (1-(2-methypropyl)-1H-imidazo[4,5-c]quinoline-4-amine); ImmTher™ (N-acetylglucosaminy 1-Nacetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™ ("Immunostimulating Complexes"); ISCOPREP 7.0.3.™; liposomes; LOXORIBINE™ (7-allyl-8-oxoguanosine (guanine)); LT oral adjuvant (*E. coli* labile enterotoxin-protoxin); microspheres; microparticles of any composition; MF59™ (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes (N-acetyl-L-alanyl-D-isoglutaminyl-L-alanine-2-(1,2-dipalmitoyl-sn-glycero-3-(hydroxyphosphoryloxy))ethylamide, monosodium salt); MURAMETIDE™ (Nac-Mur-L-Ala-D-Gln-OCH₃); MURAPALMITINE™ and D-MURAPALMITINE™ (Nac-Mur-L-Thr-D-isoGln-sn-glyceroldipalmitoyl); NAGO (neuraminidase-galactose oxidase); nanospheres; nanoparticles of any composition; NISVs (non-ionic surfactant vesicles); PLEURAN™ (beta-glucan); PLGA, PGA, and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); protein cochleates; STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes; Sendai-containing lipid matrices; Span-85 (sorbitan trioleate); Specol (emulsion of Marcol 52, Span 85 and Tween 85); squalene; Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide); lipopeptides; Pam3Cys; aluminium salts; Adju-phos; Alhydrogel; Rehydragel; emulsions; CFA; SAF; IFA; MF59; Provax; TiterMax; Montanide; Vaxfectin; copolymers; Optivax (CRL1005); L121; Poloaxmer4010; cochleates; BIORAL; plant derived adjuvants; QS21; Quil A; Iscomatrix; and ISCOM.

21. The pharmaceutical composition according to claim 19, wherein the adjuvant is selected from the group consisting of Tomatine; biopolymers; PLG; PMM; Inulin; microbe derived adjuvants; Romurtide; DETOX; MPL; CWS; Mannose; CpG7909; ISS-1018; IC31; Imidazoquinolines; Ampligen; Ribi529; IMOxine; IRIVs; VLPs; cholera toxin; heat-labile toxin; Pam3Cys; Flagellin; GPI anchor; LNFPIII/Lewis X; antimicrobial peptides; UC-1V150; RSV fusion protein; and cdiGMP.

22. The pharmaceutical composition according to claim 19, wherein the adjuvant is selected from the group consisting of CGRP neuropeptide; protamine; nucleoline; spermine; spermidine; poly-L-lysine (PLL); poly-arginine; basic polypeptides; cell penetrating peptides (CPPs); Tat; HIV-1 Tat (HIV); Tat-derived peptides; Penetratin; VP22 derived or analog peptides; HSV VP22 (Herpes simplex); MAP; KALA; protein transduction domains (PTDs); PpT620; proline-rich peptides; arginine-rich peptides; lysine-rich peptides; MPG-peptide(s); Pep-1; L-oligomers; Calcitonin peptide(s); Antennapedia-derived peptides; pAntp; plsl; FGF; Lactoferrin; Transportan; Buforin-2; Bac715-24; SynB; SynB(1); pVEC; hCT-derived peptides; SAP; protamine; and histones.

23. The pharmaceutical composition according to claim 15, wherein the nucleic acid molecule is complexed with lipids, polycationic compounds, polycationic peptides or polycationic proteins.

24. The pharmaceutical composition according to claim 15, further comprising cationic or polycationic proteins or peptides selected from the group consisting of proteins or peptides having the following total formula: $(Arg)_l; (Lys)_m;$ $(His)_n; (Orn)_o; (Xaa)_x,$ wherein 1+m+n+o+x=8-15, and 1, m, n or o are independently any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa is any amino acid selected from native or non-native amino acids except Arg, Lys, His or Orn; and x is any number selected from 0, 1, 2, 3 or 4, provided that the overall content of Xaa does not exceed 50% of all amino acids of the oligopeptide.

25. The pharmaceutical composition according to claim 15, further comprising cationic polysaccharides, chitosan, polybrene, cationic polymers, polyethyleneimine (PEI), cationic lipids, DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicyl-spermin, DIMRI: Dimyristo-oxypropyl dimethyl hydroxyethyl ammonium bromide, DOTAP: dioleoyloxy-3-(trimethylammonio)propane, DC-6-14: 0,0-ditetradecanoyl-N-(α-trimethylammonioacetyl)diethanolamine chloride, CLIP1: rac[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac[2(2,3-dihexadecyloxypropyl-oxysuccinyloxy)ethyl]-trimethylammonium, oligofectamine, modified polyaminoacids, β-aminoacid-polymers, reversed polyamides, modified polyethylenes, PVP (poly(N-ethyl-4-vinylpyridinium bromide)), modified acrylates, pDMAEMA (poly(dimethylaminoethyl methylacrylate)), modified Amidoamines, pAMAM (poly(amidoamine)), modified polybetaaminoester (PBAE), diamine end modified 1,4 butanediol diacrylate-co-5-amino-1-pentanol polymers, dendrimers, polypropylamine dendrimers, pAMAM based dendrimers, polyimine(s), poly(propyleneimine), polyallylamine, sugar backbone based polymers, cyclodextrin based polymers, dextran based polymers, Chitosan, silan backbone based polymers, PMOXA-PDMS copolymers, block polymers consisting of a combination of one or more cationic blocks, hydrophilic blocks or hydrophobic blocks.

26. The pharmaceutical composition according to claim 15, wherein the pharmaceutical composition is a vaccine.

27. A kit comprising the nucleic acid molecule according to claim 1.

28. The nucleic acid according to claim 1, wherein the nucleic acid molecule comprises a DNA encoding the sequence of SEQ ID NO: 114.

29. The nucleic acid according to claim 1, wherein the nucleic acid molecule comprises a DNA encoding the sequence of SEQ ID NO: 115.

30. The nucleic acid according to claim 1, wherein the nucleic acid molecule comprises a DNA encoding the sequence of SEQ ID NO: 116.

31. The nucleic acid according to claim 1, wherein the nucleic acid molecule comprises a DNA encoding the sequence of SEQ ID NO: 117.

32. The nucleic acid according to claim 1, wherein the nucleic acid molecule comprises a DNA encoding the sequence of SEQ ID NO: 118.

33. The nucleic acid according to claim 1, wherein the nucleic acid molecule comprises a DNA encoding the sequence of SEQ ID NO: 119.

34. The nucleic acid according to claim 1, wherein the nucleic acid molecule does not comprise a nucleoside analogue.

* * * * *

SEQUENCE LISTING

```
<160> NUMBER OF SEQ ID NOS: 126

<210> SEQ ID NO 1
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 1
gguuuuuuuu uuuuuuuggg                                                 20

<210> SEQ ID NO 2
<211> LENGTH: 20
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 2 gggggguuuuu uuuuugggggg                                              20

<210> SEQ ID NO 3
<211> LENGTH: 40
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 3 gggggguuuuu uuuuuuuuuu uuuuuuuuuu uuuuugggggg                        40

<210> SEQ ID NO 4
<211> LENGTH: 39
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 4
gugugugugu guuuuuuuuu uuuuuuugug ugugugugu                           39

<210> SEQ ID NO 5
<211> LENGTH: 39
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 5
gguugguugg uuuuuuuuuu uuuuuuugg u ugguuggu u                         39

<210> SEQ ID NO 6
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 6
gggggggggu uuggggggggg                                               20

<210> SEQ ID NO 7
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 7 ggggggggguu uugggggggg                                               20

<210> SEQ ID NO 8
<211> LENGTH: 20
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 8
ggggggguuu uuuggggggg                                                   20

<210> SEQ ID NO 9
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 9
ggggggguuu uuuugggggg                                                   20

<210> SEQ ID NO 10
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 10
gggggguuuu uuuugggggg                                                   20

<210> SEQ ID NO 11
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 11
gggggguuuu uuuuuggggg                                                   20

<210> SEQ ID NO 12
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 12
gggggguuuu uuuuuuggggg                                                  20

<210> SEQ ID NO 13
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 13 gggggguuuuu uuuuuugggg                                                  20

<210> SEQ ID NO 14
<211> LENGTH: 20
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 14 gggggguuuuu uuuuuuuggg                                              20

<210> SEQ ID NO 15
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 15 ggggguuuuuu uuuuuuuggg                                              20

<210> SEQ ID NO 16
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 16 ggggguuuuuu uuuuuuuugg                                              20

<210> SEQ ID NO 17
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 17
gguuuuuuuu uuuuuuuugg                                               20

<210> SEQ ID NO 18
<211> LENGTH: 20
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 18
guuuuuuuuu uuuuuuuuug                                               20

<210> SEQ ID NO 19
<211> LENGTH: 22
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 19
gggggggggg uuuggggggg gg                                            22

<210> SEQ ID NO 20
<211> LENGTH: 22
<212> TYPE: RNA
<213> ORGANISM: Artificial Sequence
```

```
<220> FEATURE:
<223> OTHER INFORMATION: Description of artificial sequence: Exemplary
      core structure "GlXmGn" of formula (I)

<400> SEQUENCE: 20 ggggggggggu uuggggggggg gg                                              22

<210> SEQ ID NO 21
<211> LENGTH: 22
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 21
gggggggguu uuugggggggg gg                                               22

<210> SEQ ID NO 22
<211> LENGTH: 22
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 22
gggggggguu uuuugggggg gg                                                22

<210> SEQ ID NO 23
<211> LENGTH: 22
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 23
ggggggguuu uuuugggggg gg                                                22

<210> SEQ ID NO 24
<211> LENGTH: 22
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 24
ggggggguuu uuuuugggg gg                                                 22

<210> SEQ ID NO 25
<211> LENGTH: 22
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 25
ggggggguuu uuuuuuggg gg                                                 22

<210> SEQ ID NO 26
<211> LENGTH: 22
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 26
gggggguuuu uuuuuuuggg gg                                                  22

<210> SEQ ID NO 27
<211> LENGTH: 22
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 27
gggggguuuu uuuuuuuugg gg                                                  22

<210> SEQ ID NO 28
<211> LENGTH: 22
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 28 gggggguuuuu uuuuuuuugg gg                                                 22

<210> SEQ ID NO 29
<211> LENGTH: 22
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 29 gggggguuuuu uuuuuuuuug gg                                                 22

<210> SEQ ID NO 30
<211> LENGTH: 22
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 30
ggguuuuuuu uuuuuuuuug gg                                                  22

<210> SEQ ID NO 31
<211> LENGTH: 22
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 31
gguuuuuuuu uuuuuuuuuu gg                                                  22

<210> SEQ ID NO 32
<211> LENGTH: 24
<212> TYPE: RNA
<213> ORGANISM: Artificial Sequence
```

```
<220> FEATURE:
<223> OTHER INFORMATION: Description of artificial sequence: Exemplary
      core structure "GlXmGn" of formula (I)

<400> SEQUENCE: 32
gggggggggg guuugggggg gggg                                              24

<210> SEQ ID NO 33
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 33
gggggggggg uuuuggggggg gggg                                             24

<210> SEQ ID NO 34
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 34 ggggggggggu uuuuggggg gggg                                              24

<210> SEQ ID NO 35
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 35 ggggggggggu uuuuugggg gggg                                              24

<210> SEQ ID NO 36
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 36
gggggggguu uuuuugggg gggg                                               24

<210> SEQ ID NO 37
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 37
gggggggguu uuuuuuggg gggg                                               24

<210> SEQ ID NO 38
<211> LENGTH: 24
<212> TYPE: RNA
<213> ORGANISM: Artificial Sequence
```

```
<220> FEATURE:
<223> OTHER INFORMATION: Description of artificial sequence: Exemplary
      core structure "GlXmGn" of formula (I)

<400> SEQUENCE: 38 ggggggggguu uuuuuuuugg gggg                                              24

<210> SEQ ID NO 39
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 39
ggggggguuu uuuuuuuugg gggg                                               24

<210> SEQ ID NO 40
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 40
ggggggguuu uuuuuuuug gggg                                                24

<210> SEQ ID NO 41
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 41
gggggguuuu uuuuuuuug gggg                                                24

<210> SEQ ID NO 42
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 42
gggggguuuu uuuuuuuuuu gggg                                               24

<210> SEQ ID NO 43
<211> LENGTH: 24
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 43
gggguuuuuu uuuuuuuuuu gggg                                               24

<210> SEQ ID NO 44
<211> LENGTH: 24
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 44
ggguuuuuuu uuuuuuuuuu uggg                                          24

<210> SEQ ID NO 45
<211> LENGTH: 32
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 45
guuuuuuuuu uuuuuuuuuu uuuuuuuuuu ug                                 32

<210> SEQ ID NO 46
<211> LENGTH: 34
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 46
gguuuuuuuu uuuuuuuuuu uuuuuuuuuu uugg                               34

<210> SEQ ID NO 47
<211> LENGTH: 36
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 47
ggguuuuuuu uuuuuuuuuu uuuuuuuuuu uuuggg                             36

<210> SEQ ID NO 48
<211> LENGTH: 37
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 48
gggguuuuuu uuuuuuuuuu uuuuuuuuuu uuuggg                             37

<210> SEQ ID NO 49
<211> LENGTH: 39
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 49
ggggguuuuu uuuuuuuuuu uuuuuuuuuu uuuugggg                           39

<210> SEQ ID NO 50
<211> LENGTH: 41
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 50
gggggguuuu uuuuuuuuuu uuuuuuuuuu uuuuuugggg g                          41

<210> SEQ ID NO 51
<211> LENGTH: 43
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 51
ggggggguuu uuuuuuuuuu uuuuuuuuuu uuuuuuuggg ggg                        43

<210> SEQ ID NO 52
<211> LENGTH: 45
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 52
gggggggguu uuuuuuuuuu uuuuuuuuuu uuuuuuuugg ggggg                      45

<210> SEQ ID NO 53
<211> LENGTH: 47
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 53 ggggggggu uuuuuuuuuu uuuuuuuuuu uuuuuuuug ggggggg                      47

<210> SEQ ID NO 54
<211> LENGTH: 7
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 54 gguuugg                                                                 7

<210> SEQ ID NO 55
<211> LENGTH: 8
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 55 gguuuugg                                                                8

<210> SEQ ID NO 56
<211> LENGTH: 9
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 56 gguuuuugg                                                                9

<210> SEQ ID NO 57
<211> LENGTH: 10
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 57
gguuuuuugg                                                              10

<210> SEQ ID NO 58
<211> LENGTH: 11
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 58
gguuuuuuug g                                                            11

<210> SEQ ID NO 59
<211> LENGTH: 12
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 59
gguuuuuuuu gg                                                           12

<210> SEQ ID NO 60
<211> LENGTH: 13
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 60
gguuuuuuuu ugg                                                          13

<210> SEQ ID NO 61
<211> LENGTH: 14
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 61
gguuuuuuuu uugg                                                         14

<210> SEQ ID NO 62
<211> LENGTH: 15
<212> TYPE: RNA
<213> ORGANISM: Artificial Sequence
```

```
<220> FEATURE:
<223> OTHER INFORMATION: Description of artificial sequence: Exemplary
      core structure "GlXmGn" of formula (I)

<400> SEQUENCE: 62
gguuuuuuuu uuugg                                                    15

<210> SEQ ID NO 63
<211> LENGTH: 16
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 63
gguuuuuuuu uuuugg                                                   16

<210> SEQ ID NO 64
<211> LENGTH: 17
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 64
gguuuuuuuu uuuuugg                                                  17

<210> SEQ ID NO 65
<211> LENGTH: 18
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 65
gguuuuuuuu uuuuuugg                                                 18

<210> SEQ ID NO 66
<211> LENGTH: 19
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 66
gguuuuuuuu uuuuuuugg                                                19

<210> SEQ ID NO 67
<211> LENGTH: 9
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 67 ggguuuggg                                                            9

<210> SEQ ID NO 68
<211> LENGTH: 10
<212> TYPE: RNA
<213> ORGANISM: Artificial Sequence
```

```
<220> FEATURE:
<223> OTHER INFORMATION: Description of artificial sequence: Exemplary
      core structure "GlXmGn" of formula (I)

<400> SEQUENCE: 68
ggguuuuggg                                                              10

<210> SEQ ID NO 69
<211> LENGTH: 11
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 69
ggguuuuugg g                                                            11

<210> SEQ ID NO 70
<211> LENGTH: 12
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 70
ggguuuuuug gg                                                           12

<210> SEQ ID NO 71
<211> LENGTH: 13
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 71
ggguuuuuuu ggg                                                          13

<210> SEQ ID NO 72
<211> LENGTH: 14
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 72
ggguuuuuuu uggg                                                         14

<210> SEQ ID NO 73
<211> LENGTH: 15
<212> TYPE: RNA
<213> ORGANISM: Artificial Sequence
<220> FEATURE:
<223> OTHER INFORMATION: Description of artificial sequence: Exemplary
      core structure "GlXmGn" of formula (I)

<400> SEQUENCE: 73
ggguuuuuuu uuggg                                                        15

<210> SEQ ID NO 74
<211> LENGTH: 16
<212> TYPE: RNA
<213> ORGANISM: Artificial Sequence
```

```
<220> FEATURE:
<223> OTHER INFORMATION: Description of artificial sequence:  Exemplary
      core structure "GlXmGn" of formula (I)

<400> SEQUENCE: 74
ggguuuuuuu uuuggg                                                  16

<210> SEQ ID NO 75
<211> LENGTH: 17
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 75
ggguuuuuuu uuuuggg                                                 17

<210> SEQ ID NO 76
<211> LENGTH: 18
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 76
ggguuuuuuu uuuuuggg                                                18

<210> SEQ ID NO 77
<211> LENGTH: 19
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 77
ggguuuuuuu uuuuuuggg                                               19

<210> SEQ ID NO 78
<211> LENGTH: 57
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 78
ggguuuuuuu uuuuuuuugg guuuuuuuuu uuuuugggu uuuuuuuuuu uuuggg       57

<210> SEQ ID NO 79
<211> LENGTH: 42
<212> TYPE: RNA
<213> ORGANISM: Artificial Sequence
<220> FEATURE:
<223> OTHER INFORMATION: Description of artificial sequence:  Exemplary
      core structure "GlXmGn" of formula (I)

<400> SEQUENCE: 79
ggguuuuuuu uuuuuuugg ggggguuuuu uuuuuuuug gg                       42

<210> SEQ ID NO 80
<211> LENGTH: 51
<212> TYPE: RNA
<213> ORGANISM: Artificial Sequence
```

```
<220> FEATURE:
<223> OTHER INFORMATION: Description of artificial sequence: Exemplary
      core structure "GlXmGn" of formula (I)

<400> SEQUENCE: 80
ggguuugggu uugggutuugg guuugggutuu gggutugggu uggguuugg g            51

<210> SEQ ID NO 81
<211> LENGTH: 57
<212> TYPE: RNA
<213> ORGANISM: Artificial Sequence
<220> FEATURE:
<223> OTHER INFORMATION: Description of artificial sequence: Exemplary
      core structure "ClXmCn" of formula (Ia)

<400> SEQUENCE: 81
cccuuuuuuu uuuuuuucc cuuuuuuuuu uuuuucccu uuuuuuuuuu uuucccc        57

<210> SEQ ID NO 82
<211> LENGTH: 51
<212> TYPE: RNA
<213> ORGANISM: Artificial Sequence
<220> FEATURE:
<223> OTHER INFORMATION: Description of artificial sequence: Exemplary
      core structure "ClXmCn" of formula (Ia)

<400> SEQUENCE: 82
cccuuucccu uucccuuucc cuuucccuuu cccuuucccu uucccuuucc c             51

<210> SEQ ID NO 83
<211> LENGTH: 42
<212> TYPE: RNA
<213> ORGANISM: Artificial Sequence
<220> FEATURE:
<223> OTHER INFORMATION: Description of artificial sequence: Exemplary
      core structure "ClXmCn" of formula (Ia)

<400> SEQUENCE: 83
cccuuuuuuu uuuuuuucc ccccuuuuuu uuuuuuuuuc cc                       42

<210> SEQ ID NO 84
<211> LENGTH: 60
<212> TYPE: RNA
<213> ORGANISM: Artificial Sequence
<220> FEATURE:
<223> OTHER INFORMATION: Description of sequence: Exemplary sequence
      according to formula (I)

<400> SEQUENCE: 84
uagcgaagcu cuuggaccua gguuuuuuuu uuuuuuuggg ugcguuccua gaaguacacg    60

<210> SEQ ID NO 85
<211> LENGTH: 60
<212> TYPE: RNA
<213> ORGANISM: Artificial Sequence
<220> FEATURE:
<223> OTHER INFORMATION: Description of sequence: Exemplary sequence
      according to formula (I)
<220> FEATURE:
<221> NAME/KEY: misc_feature
<222> LOCATION: (1)..(60)
<223> OTHER INFORMATION: sequence is double-stranded RNA

<400> SEQUENCE: 85
uagcgaagcu cuuggaccua gguuuuuuuu uuuuuuuggg ugcguuccua gaaguacacg    60
```

```
<210> SEQ ID NO 86
<211> LENGTH: 60
<212> TYPE: RNA
<213> ORGANISM: Artificial Sequence
<220> FEATURE:
<223> OTHER INFORMATION: Description of sequence: Exemplary sequence
      according to formula (Ia)

<400> SEQUENCE: 86
uagcgaagcu cuuggaccua ccuuuuuuuu uuuuuuuccc ugcguuccua gaaguacacg        60

<210> SEQ ID NO 87
<211> LENGTH: 60
<212> TYPE: RNA
<213> ORGANISM: Artificial Sequence
<220> FEATURE:
<223> OTHER INFORMATION: Description of sequence: Exemplary sequence
      according to formula (Ia)
<220> FEATURE:
<221> NAME/KEY: misc_feature
<222> LOCATION: (1)..(60)
<223> OTHER INFORMATION: sequence is double-stranded RNA

<400> SEQUENCE: 87
uagcgaagcu cuuggaccua ccuuuuuuuu uuuuuuuccc ugcguuccua gaaguacacg        60

<210> SEQ ID NO 88
<211> LENGTH: 40
<212> TYPE: RNA
<213> ORGANISM: Artificial Sequence
<220> FEATURE:
<223> OTHER INFORMATION: Description of sequence: Exemplary sequence
      according to general formula (II)

<400> SEQUENCE: 88
cccccccccc cccccccccc gguuuuuuuu uuuuuuuggg                              40

<210> SEQ ID NO 89
<211> LENGTH: 40
<212> TYPE: RNA
<213> ORGANISM: Artificial Sequence
<220> FEATURE:
<223> OTHER INFORMATION: Description of sequence: Exemplary sequence
      according to general formula (II)
<220> FEATURE:
<221> NAME/KEY: misc_feature
<222> LOCATION: (1)..(20)
<223> OTHER INFORMATION: sequence is ds RNA (poly(I:C))

<400> SEQUENCE: 89
cccccccccc cccccccccc gguuuuuuuu uuuuuuuggg                              40

<210> SEQ ID NO 90
<211> LENGTH: 40
<212> TYPE: RNA
<213> ORGANISM: Artificial Sequence
<220> FEATURE:
<223> OTHER INFORMATION: Description of sequence: Exemplary sequence
      according to general formula (II)
<220> FEATURE:
<221> NAME/KEY: misc_feature
<222> LOCATION: (23)..(37)
<223> OTHER INFORMATION: sequence is double stranded ((A:U)

<400> SEQUENCE: 90
cccccccccc cccccccccc gguuuuuuuu uuuuuuuggg                              40
```

```
<210> SEQ ID NO 91
<211> LENGTH: 40
<212> TYPE: RNA
<213> ORGANISM: Artificial Sequence
<220> FEATURE:
<223> OTHER INFORMATION: Description of sequence: Exemplary sequence
      according to general formula (II)
<220> FEATURE:
<221> NAME/KEY: misc_feature
<222> LOCATION: (1)..(40)
<223> OTHER INFORMATION: sequence is double-stranded RNA

<400> SEQUENCE: 91
cccccccccc cccccccccc gguuuuuuuu uuuuuuuggg                           40

<210> SEQ ID NO 92
<211> LENGTH: 80
<212> TYPE: RNA
<213> ORGANISM: Artificial Sequence
<220> FEATURE:
<223> OTHER INFORMATION: Description of sequence: Exemplary sequence
      according to general formula (II)

<400> SEQUENCE: 92
cccccccccc cccccccccc uagcgaagcu cuuggaccua gguuuuuuuu uuuuuuuggg     60
ugcguuccua gaaguacacg                                                 80

<210> SEQ ID NO 93
<211> LENGTH: 80
<212> TYPE: RNA
<213> ORGANISM: Artificial Sequence
<220> FEATURE:
<223> OTHER INFORMATION: Description of sequence: Exemplary sequence
      according to general formula (II)
<220> FEATURE:
<221> NAME/KEY: misc_feature
<222> LOCATION: (1)..(80)
<223> OTHER INFORMATION: sequence is double-stranded RNA

<400> SEQUENCE: 93
cccccccccc cccccccccc gguuuuuuuu uuuuuuuggg ugcguuccua gaaguacacg     60
uagcgaagcu cuuggaccua                                                 80

<210> SEQ ID NO 94
<211> LENGTH: 80
<212> TYPE: RNA
<213> ORGANISM: Artificial Sequence
<220> FEATURE:
<223> OTHER INFORMATION: Description of sequence: Exemplary sequence
      according to general formula (II)
<220> FEATURE:
<221> NAME/KEY: misc_feature
<222> LOCATION: (21)..(80)
<223> OTHER INFORMATION: sequence is double stranded RNA

<400> SEQUENCE: 94
cccccccccc cccccccccc gguuuuuuuu uuuuuuuggg ugcguuccua gaaguacacg     60
uagcgaagcu cuuggaccua                                                 80

<210> SEQ ID NO 95
<211> LENGTH: 20
<212> TYPE: RNA
<213> ORGANISM: Artificial Sequence
<220> FEATURE:
<223> OTHER INFORMATION: Description of sequence: exemplary sequence of
      stem 1 of formula (IIIa) or (IIIb)(sequence is palindromic to SEQ
      ID NO: 96)
```

```
<400> SEQUENCE: 95
uagcgaagcu cuuggaccua                                                    20

<210> SEQ ID NO 96
<211> LENGTH: 20
<212> TYPE: RNA
<213> ORGANISM: Artificial Sequence
<220> FEATURE:
<223> OTHER INFORMATION: Description of sequence: exemplary sequence of
      stem 2 of formula (IIIa) or (IIIb)(sequence is palindromic to SEQ
      ID NO: 95)

<400> SEQUENCE: 96
uagguccaag agcuucgcua                                                    20

<210> SEQ ID NO 97
<211> LENGTH: 11
<212> TYPE: RNA
<213> ORGANISM: Artificial Sequence
<220> FEATURE:
<223> OTHER INFORMATION: Description of sequence: exemplary sequence of
      stem 1 of formula (IIIa) or (IIIb)(sequence is palindromic to SEQ
      ID NO: 98)

<400> SEQUENCE: 97
gccgcgggcc g                                                             11

<210> SEQ ID NO 98
<211> LENGTH: 11
<212> TYPE: RNA
<213> ORGANISM: Artificial Sequence
<220> FEATURE:
<223> OTHER INFORMATION: Description of sequence: exemplary sequence of
      stem 2 of formula (IIIa) or (IIIb)(sequence is palindromic to SEQ
      ID NO: 97)

<400> SEQUENCE: 98
cggcccgcgg c                                                             11

<210> SEQ ID NO 99
<211> LENGTH: 10
<212> TYPE: RNA
<213> ORGANISM: Artificial Sequence
<220> FEATURE:
<223> OTHER INFORMATION: Description of sequence: exemplary sequence of
      stem 1 of formula (IIIa) or (IIIb)(sequence is palindromic to SEQ
      ID NO: 100)

<400> SEQUENCE: 99
gacacggugc                                                               10

<210> SEQ ID NO 100
<211> LENGTH: 10
<212> TYPE: RNA
<213> ORGANISM: Artificial Sequence
<220> FEATURE:
<223> OTHER INFORMATION: Description of sequence: exemplary sequence of
      stem 2 of formula (IIIa) or (IIIb)(sequence is palindromic to SEQ
      ID NO: 99)

<400> SEQUENCE: 100
gcaccgugca                                                               10

<210> SEQ ID NO 101
<211> LENGTH: 8
<212> TYPE: RNA
<213> ORGANISM: Artificial Sequence
```

```
<220> FEATURE:
<223> OTHER INFORMATION: Description of sequence: exemplary sequence of
      either stem 1/stem2 of formula (IIIa) or (IIIb)(sequence is
      intrinsic palindromic)

<400> SEQUENCE: 101 accuaggu                                                                    8

<210> SEQ ID NO 102
<211> LENGTH: 8
<212> TYPE: RNA
<213> ORGANISM: Artificial Sequence
<220> FEATURE:
<223> OTHER INFORMATION: Description of sequence: exemplary sequence of
      either stem 1/stem2 of formula (IIIa) or (IIIb)(sequence is
      intrinsic palindromic)

<400> SEQUENCE: 102 uggaucca                                                                    8

<210> SEQ ID NO 103
<211> LENGTH: 5
<212> TYPE: RNA
<213> ORGANISM: Artificial Sequence
<220> FEATURE:
<223> OTHER INFORMATION: Description of sequence: exemplary sequence of
      stem 1 of formula (IIIa) or (IIIb)(sequence is palindromic to SEQ
      ID NO: 104)

<400> SEQUENCE: 103 ccugc                                                                       5

<210> SEQ ID NO 104
<211> LENGTH: 5
<212> TYPE: RNA
<213> ORGANISM: Artificial Sequence
<220> FEATURE:
<223> OTHER INFORMATION: Description of sequence: exemplary sequence of
      stem 2 of formula (IIIa) or (IIIb)(sequence is palindromic to SEQ
      ID NO: 103)

<400> SEQUENCE: 104 gcagg                                                                       5

<210> SEQ ID NO 105
<211> LENGTH: 5
<212> TYPE: RNA
<213> ORGANISM: Artificial Sequence
<220> FEATURE:
<223> OTHER INFORMATION: Description of sequence: exemplary sequence of
      stem 1 of formula (IIIa) or (IIIb)(sequence is palindromic to SEQ
      ID NO: 106)

<400> SEQUENCE: 105 gcagg                                                                       5

<210> SEQ ID NO 106
<211> LENGTH: 5
<212> TYPE: RNA
<213> ORGANISM: Artificial Sequence
<220> FEATURE:
<223> OTHER INFORMATION: Description of sequence: exemplary sequence of
      stem 2 of formula (IIIa) or (IIIb)(sequence is palindromic to SEQ
      ID NO: 105)

<400> SEQUENCE: 106 ccugc                                                                       5
```

```
<210> SEQ ID NO 107
<211> LENGTH: 60
<212> TYPE: RNA
<213> ORGANISM: Artificial Sequence
<220> FEATURE:
<223> OTHER INFORMATION: Description of sequence: inventive nucleic acid
      according to either formula (IIIa) or (IIIb)

<400> SEQUENCE: 107
uagcgaagcu cuuggaccua gguuuuuuuu uuuuuuuggg uagguccaag agcuucgcua        60

<210> SEQ ID NO 108
<211> LENGTH: 122
<212> TYPE: RNA
<213> ORGANISM: Artificial Sequence
<220> FEATURE:
<223> OTHER INFORMATION: Description of sequence: inventive nucleic acid
      according to either formula (IIIa) or (IIIb)

<400> SEQUENCE: 108
uagcgaagcu cuuggaccua gguuuuuuuu uuuuuuuggg ugcguuccua gaaguacacg        60
gccgcgggcc gugcguuccu agaaguacac gcggcccgcg gcugcguucc uagaaguaca      120
cg                                                                    122

<210> SEQ ID NO 109
<211> LENGTH: 18
<212> TYPE: PRT
<213> ORGANISM: Unknown
<220> FEATURE:
<223> OTHER INFORMATION: Description of sequence: sequence of protamin
      P1

<400> SEQUENCE: 109

Ser Arg Ser Arg Tyr Tyr Arg Gln Arg Gln Arg Ser Arg Arg Arg
1               5                   10                  15

Arg Arg

<210> SEQ ID NO 110
<211> LENGTH: 21
<212> TYPE: PRT
<213> ORGANISM: Unknown
<220> FEATURE:
<223> OTHER INFORMATION: Description of sequence: sequence of protamin
      P2

<400> SEQUENCE: 110

Arg Arg Arg Leu His Arg Ile His Arg Arg Gln His Arg Ser Cys Arg
1               5                   10                  15

Arg Arg Lys Arg Arg
            20

<210> SEQ ID NO 111
<211> LENGTH: 13
<212> TYPE: RNA
<213> ORGANISM: Unknown
<220> FEATURE:
<223> OTHER INFORMATION: Description of sequence: Kozak sequence

<400> SEQUENCE: 111
gccgccacca ugg                                                         13

<210> SEQ ID NO 112
<211> LENGTH: 13
<212> TYPE: RNA
<213> ORGANISM: Artificial Sequence
```

```
<220> FEATURE:
<223> OTHER INFORMATION: Description of sequence: generic stabilizing
      sequence of the formula (C/U)CCANxCCC(U/A)PyxUC(C/U)CC
<220> FEATURE:
<223> OTHER INFORMATION: Any number of any ribonucleic acid can be
      inserted between positions 4 and 5
<220> FEATURE:
<223> OTHER INFORMATION: Any number of pyrimidines can be inserted
      between positions 8 and 9
<220> FEATURE:
<221> NAME/KEY: misc_feature
<222> LOCATION: (1)..(1)
<223> OTHER INFORMATION: n is c or u
<220> FEATURE:
<221> NAME/KEY: variation
<222> LOCATION: (1)..(1)
<223> OTHER INFORMATION: ribonucleic acid is cytidine (cytosine) or
      uridine (uracil)
<220> FEATURE:
<221> NAME/KEY: misc_feature
<222> LOCATION: (8)..(8)
<223> OTHER INFORMATION: n is u or a
<220> FEATURE:
<221> NAME/KEY: variation
<222> LOCATION: (8)..(8)
<223> OTHER INFORMATION: ribonucleic acid is uridine (uracil) or
      adenosine
<220> FEATURE:
<221> NAME/KEY: misc_feature
<222> LOCATION: (11)..(11)
<223> OTHER INFORMATION: n is c or u
<220> FEATURE:
<221> NAME/KEY: variation
<222> LOCATION: (11)..(11)
<223> OTHER INFORMATION: ribonucleic acid is cytidine (cytosine) or
      uridine (uracil)

<400> SEQUENCE: 112
nccacccnuc  ncc                                                         13

<210> SEQ ID NO 113
<211> LENGTH: 20
<212> TYPE: RNA
<213> ORGANISM: Artificial Sequence
<220> FEATURE:
<223> OTHER INFORMATION: Description of sequence:  immune-stimulating
      oligo RNA40

<400> SEQUENCE: 113
gcccgucugu ugugugacuc                                                   20

<210> SEQ ID NO 114
<211> LENGTH: 229
<212> TYPE: RNA
<213> ORGANISM: Artificial Sequence
<220> FEATURE:
<223> OTHER INFORMATION: Description of sequence:  Exemplary sequence
      according to formula (I)

<400> SEQUENCE: 114
gggagaaagc ucaagcuugg agcaaugccc gcacauugag gaaaccgagu ugcauaucuc        60
agaguauugg cccccgugua gguuauucuu gacagacagu ggagcuuauu cacucccagg       120
auccgagucg cauacuacgg uacuggugac agaccuaggu cgucaguuga ccaguccgcc       180
acuagacgug aguccgucaa agcaguuaga uguuacacuc uauuagauc                   229

<210> SEQ ID NO 115
<211> LENGTH: 547
<212> TYPE: RNA
<213> ORGANISM: Artificial Sequence
```

<220> FEATURE:
<223> OTHER INFORMATION: Description of sequence: Exemplary sequence
      according to formula (I)

<400> SEQUENCE: 115
gggagaaagc ucaagcuugg agcaaugccc gcacauugag gaaaccgagu ugcauaucuc      60
agaguauugg cccccgugua gguuauucuu gacagacagu ggagcuuauu cacucccagg     120
auccgagucg cauacuacgg uacuggugac agaccuaggu cgucaguuga ccaguccgcc     180
acuagacgug aguccgucaa agcaguuaga uguuacacuc uauuagaucu cggauuacag     240
cuggaaggag caggaguagu guucuugcuc uaaguaccga gugugcccaa uacccgauca     300
gcuuauuaac gaacggcucc uccucuuaga cugcagcgua agugcggaau cuggggauca     360
aauuacugac ugccuggauu acccucggac auauaaccuu guagcacgcu guugcuguau     420
aggugaccaa cgcccacucg aguagaccag cucucuuagu ccggacaaug auaggaggcg     480
cggucaaucu acuucuggcu aguuaagaau aggcugcacc gaccucuaua aguagcgugu     540
ccucuag                                                              547

<210> SEQ ID NO 116
<211> LENGTH: 1083
<212> TYPE: RNA
<213> ORGANISM: Artificial Sequence
<220> FEATURE:
<223> OTHER INFORMATION: Description of sequence: Exemplary sequence
      according to formula (I)

<400> SEQUENCE: 116
gggagaaagc ucaagcuugg agcaaugccc gcacauugag gaaaccgagu ugcauaucuc      60
agaguauugg cccccgugua gguuauucuu gacagacagu ggagcuuauu cacucccagg     120
auccgagucg cauacuacgg uacuggugac agaccuaggu cgucaguuga ccaguccgcc     180
acuagacgug aguccgucaa agcaguuaga uguuacacuc uauuagaucu cggauuacag     240
cuggaaggag caggaguagu guucuugcuc uaaguaccga gugugcccaa uacccgauca     300
gcuuauuaac gaacggcucc uccucuuaga cugcagcgua agugcggaau cuggggauca     360
aauuacugac ugccuggauu acccucggac auauaaccuu guagcacgcu guugcuguau     420
aggugaccaa cgcccacucg aguagaccag cucucuuagu ccggacaaug auaggaggcg     480
cggucaaucu acuucuggcu aguuaagaau aggcugcacc gaccucuaua aguagcgugu     540
ccucuagagc uacgcagguu cgcaauaaaa gcguugauua gugugcauag aacagaccuc     600
uuauucggug aaacgccaga augcuaaauu ccaauaacuc uucccaaaac gcguacggcc     660
gaagacgcgc gcuuaucuug uguacguucu cgcacaugga agaaucagcg ggcaugguuu     720
uagggcaaua ggggagcugg guagcagcga aaaagggccc cugcgcacgu agcuucgcug     780
uucgucugaa acaacccggc auccguugua gcgaucccgu uaucagguuu auucuugugc     840
gcacuaagau ucaugguguu gucgacaaua acagcgucuu ggcagauucu ggucacgugc     900
ccuaugcccg ggcuugugcc ucucaggugc acagcgauac uuaaagccuu caagguacuc     960
gacgugggua ccgauucgug acacuuccua agauuauucc acuguguuag ccccgcaccg    1020
ccgaccuaaa cugguccaau guauacgcau ucgcugagcg gaucgauaau aaaagcuuga    1080
auu                                                                 1083

```
<210> SEQ ID NO 117
<211> LENGTH: 229
<212> TYPE: RNA
<213> ORGANISM: Artificial Sequence
<220> FEATURE:
<223> OTHER INFORMATION: Description of sequence:  Exemplary sequence
      according to formula (I)

<400> SEQUENCE: 117
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu ccccuuuuuu uuuuuuuuuu     180
uuuuuaguaa augcgucuac ugaauccagc gaugaugcug gcccagauc                 229

<210> SEQ ID NO 118
<211> LENGTH: 546
<212> TYPE: RNA
<213> ORGANISM: Artificial Sequence
<220> FEATURE:
<223> OTHER INFORMATION: Description of sequence:  Exemplary sequence
      according to formula (I)

<400> SEQUENCE: 118
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu ccccuuuuuu uuuuuuuuuu     180
uuuuuaguaa augcgucuac ugaauccagc gaugaugcug gcccagaucu ucgaccacaa     240
gugcauauag uagucaucga ggucgccuu uuuuuuuuuu uuuuuuuuuu uggcccaguu      300
cugagacuuc gcuagagacu acaguuacag cugcaguagu aaccacugcg gcuauugcag     360
gaaaucccgu ucagguuuuu uuuuuuuuuu uuuuuccgc ucacuaugau uaagaaccag      420
gugagguguc acugcucucg aggucucacg agagcgcucg auacaguccu uggaagaauc     480
uuuuuuuuuu uuuuuuuuuu uugugcgacg aucacagaga acuucuauuc augcaggucu     540
gcucua                                                                546

<210> SEQ ID NO 119
<211> LENGTH: 1083
<212> TYPE: RNA
<213> ORGANISM: Artificial Sequence
<220> FEATURE:
<223> OTHER INFORMATION: Description of sequence:  Exemplary sequence
      according to formula (I)

<400> SEQUENCE: 119
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu ccccuuuuuu uuuuuuuuuu     180
uuuuuaguaa augcgucuac ugaauccagc gaugaugcug gcccagaucu ucgaccacaa     240
gugcauauag uagucaucga ggucgccuu uuuuuuuuuu uuuuuuuuuu uggcccaguu      300
cugagacuuc gcuagagacu acaguuacag cugcaguagu aaccacugcg gcuauugcag     360
gaaaucccgu ucagguuuuu uuuuuuuuuu uuuuuccgc ucacuaugau uaagaaccag      420
gugagguguc acugcucucg aggucucacg agagcgcucg auacaguccu uggaagaauc     480
uuuuuuuuuu uuuuuuuuuu uugugcgacg aucacagaga acuucuauuc augcaggucu     540
gcucuagaac gaacugaccu gacgccugaa cuuaugagcg ugcguauuuu uuuuuuuuuu     600
```

```
uuuuuuuuuc cucccaacaa augucgauca auagcugggc uguuggagac gcgucagcaa    660
augccgugcc uccauaggac guguagacuu cuauuuuuuu uuuuuuuuu uuucccggg      720 accacaaaua auauucuugc uugguugggc gcaagggccc cguaucaggu cauaaacggg    780
uacauguugc acaggcuccu uuuuuuuuuu uuuuuuuuuu uucgcugagu uauuccgguc    840
ucaaaagacg gcagacguca gucgacaaca cggucuaaag cagugcuaca aucgccgug     900 uucguguuuu uuuuuuuuuu uuuuuguga accacacgg cgugcacugu aguucgcaau     960
ucauagggua ccggcucaga guuaugccuu gguugaaaac ugcccagcau acuuuuuuuu   1020
uuuuuuuuuu uucauauucc caugcuaagc aagggaugcc gcgagucaug uuaagcuuga   1080
auu                                                                 1083
```

<210> SEQ ID NO 120
<211> LENGTH: 10
<212> TYPE: RNA
<213> ORGANISM: Artificial Sequence
<220> FEATURE:
<223> OTHER INFORMATION: Exemplary sequence of Xm of formula (I)

<400> SEQUENCE: 120
uuuaauuuuc                                                          10

<210> SEQ ID NO 121
<211> LENGTH: 10
<212> TYPE: RNA
<213> ORGANISM: Artificial sequence
<220> FEATURE:
<223> OTHER INFORMATION: Exemplary sequence of Xm of formula (I)

<400> SEQUENCE: 121
uuuuguuuua                                                          10

<210> SEQ ID NO 122
<211> LENGTH: 10
<212> TYPE: RNA
<213> ORGANISM: Artificial Sequence
<220> FEATURE:
<223> OTHER INFORMATION: Exemplary sequence of Xm of formula (I)

<400> SEQUENCE: 122
uuuguuuguu                                                          10

<210> SEQ ID NO 123
<211> LENGTH: 10
<212> TYPE: RNA
<213> ORGANISM: Artificial Sequence
<220> FEATURE:
<223> OTHER INFORMATION: Exemplary sequence of Xm of formula (I)

<400> SEQUENCE: 123
uuguuuuguu                                                          10

<210> SEQ ID NO 124
<211> LENGTH: 10
<212> TYPE: RNA
<213> ORGANISM: Artificial Sequence
<220> FEATURE:
<223> OTHER INFORMATION: Exemplary sequence of Xm of formula (I)

<400> SEQUENCE: 124
uuuuuuuuuu                                                          10

```
<210> SEQ ID NO 125
<211> LENGTH: 24
<212> TYPE: RNA
<213> ORGANISM: Artificial Sequence
<220> FEATURE:
<223> OTHER INFORMATION: synthetic oligo

<400> SEQUENCE: 125
gguuuuuuuu uuuuuuuuuu uugg                                         24

<210> SEQ ID NO 126
<211> LENGTH: 21
<212> TYPE: RNA
<213> ORGANISM: Artificial Sequence
<220> FEATURE:
<223> OTHER INFORMATION: synthetic oligo

<400> SEQUENCE: 126
uuuuuuuuuu uuuuuuuuu u                                             21
```